United States Patent
Zhou et al.

(10) Patent No.: US 10,196,606 B2
(45) Date of Patent: Feb. 5, 2019

(54) METHOD OF PRODUCING MULTIPOTENT STEM CELLS

(71) Applicant: FLINDERS UNIVERSITY OF SOUTH AUSTRALIA, Bedford Park (AU)

(72) Inventors: Xin-Fu Zhou, South Australia (AU); Yanchuang Han, Bedford Park (AU)

(73) Assignee: UNISA VENTURES PTY LTD (AU)

( * ) Notice: Subject to any disclaimer, the term of this patent is extended or adjusted under 35 U.S.C. 154(b) by 892 days.

(21) Appl. No.: 14/364,200

(22) PCT Filed: Dec. 13, 2012

(86) PCT No.: PCT/AU2012/001525
§ 371 (c)(1),
(2) Date: Nov. 7, 2014

(87) PCT Pub. No.: WO2013/086570
PCT Pub. Date: Jun. 20, 2013

(65) Prior Publication Data
US 2015/0322405 A1    Nov. 12, 2015

(30) Foreign Application Priority Data

Dec. 13, 2011  (AU) .............................. 2011905177
Mar. 29, 2012  (AU) .............................. 2012901259

(51) Int. Cl.
*C12N 5/0797* (2010.01)
*C12N 5/079* (2010.01)
*C12N 5/0793* (2010.01)
*G01N 33/50* (2006.01)

(52) U.S. Cl.
CPC ......... *C12N 5/0623* (2013.01); *C12N 5/0619* (2013.01); *C12N 5/0622* (2013.01); *G01N 33/5073* (2013.01); *C12N 2500/38* (2013.01); *C12N 2501/065* (2013.01); *C12N 2501/40* (2013.01); *C12N 2501/72* (2013.01); *C12N 2501/727* (2013.01); *C12N 2501/999* (2013.01); *C12N 2506/1307* (2013.01)

(58) Field of Classification Search
CPC .................................................. C12N 5/0623
See application file for complete search history.

(56) References Cited

U.S. PATENT DOCUMENTS

| 2010/0093090 A1 | 4/2010 | Deng et al. | |
| 2010/0319078 A1* | 12/2010 | McKnight | C12N 5/0018 800/14 |
| 2011/0275157 A1 | 4/2011 | You et al. | |
| 2012/0207744 A1* | 8/2012 | Mendlein | C12N 5/0696 424/130.1 |
| 2012/0214234 A1* | 8/2012 | Takamatsu | C12N 5/0696 435/375 |

FOREIGN PATENT DOCUMENTS

WO  WO 2011047300 A1  4/2011
WO  WO 2011050476 A1  5/2011

OTHER PUBLICATIONS

Park et al., Adv. Mater., 23:H263-H267 (2011).*
Shi et al., Cell Stem Cell, 3:568-574 (2008).*
International Search Report prepared by the Australian Patent Office dated Feb. 15, 2013, for International Application No. PCT/AU2012/001525.
Written Opinion prepared by the Australian Patent Office dated Feb. 15, 2013, for International Application No. PCT/AU2012/001525.
Zhu, S., et al. "Chemical strategies for stem cell biology and regenerative medicine", Annual Review of Biomedical Engineering, 2011, vol. 13, pp. 73-90.

* cited by examiner

*Primary Examiner* — Thomas J. Visone
(74) *Attorney, Agent, or Firm* — Sheridan Ross P.C.

(57) ABSTRACT

The present invention provides a method of producing a multipotent stem cell, said method comprising culturing at least one fibroblast cell in the presence of an effective amount of at least one small molecule reprogramming factor(s) that induces the cell to de-differentiate into a multipotent stem cell, wherein the method excludes the use of reprogramming factor(s) that are not small molecules. The small molecule reprogramming factor(s) may include a G9a HMTase inhibitor(s) and/or a MEK inhibitor(s) optionally in combination with other small molecule reprogramming factor(s). The invention also includes methods of differentiating the multipotent stem cells, cells produced by the methods, assays using the cells and kits for use in the methods.

12 Claims, 27 Drawing Sheets

Specification includes a Sequence Listing.

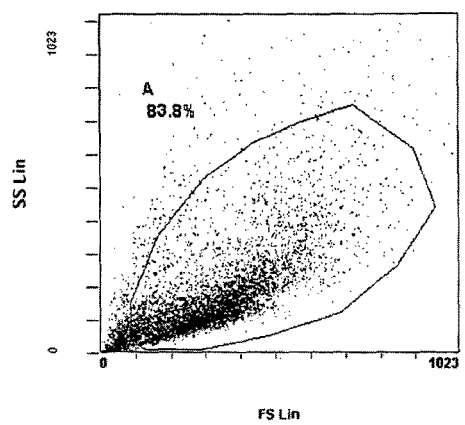 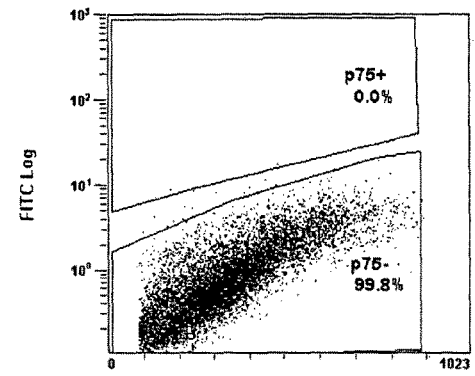
*Figure 8a*         *Figure 8b*
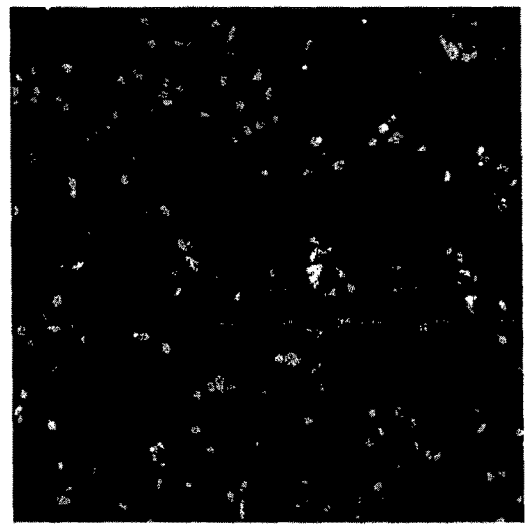
*Figure 8c*

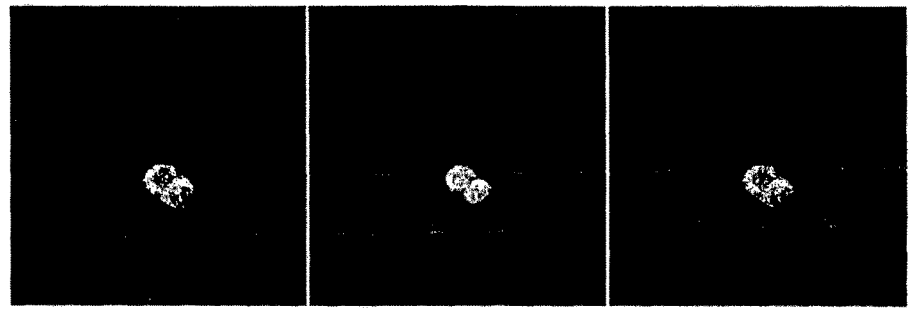
*Figure 13a*   *Figure 13b*   *Figure 13c*
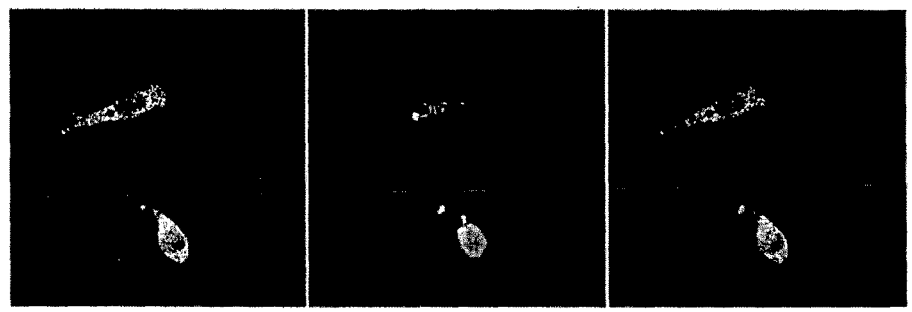
*Figure 14a*   *Figure 14b*   *Figure 14c*
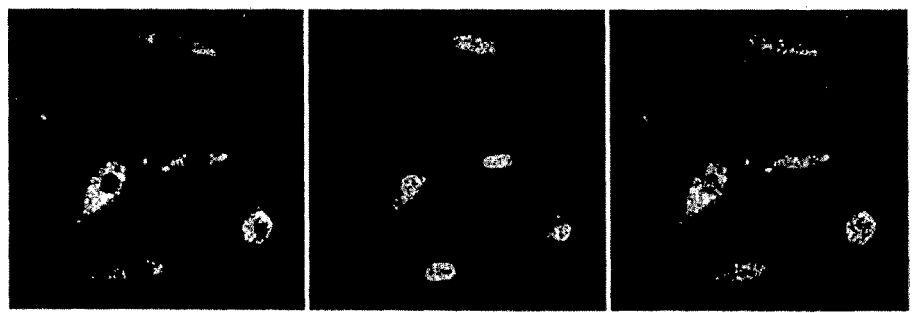
*Figure 15a*   *Figure 15b*   *Figure 15c*

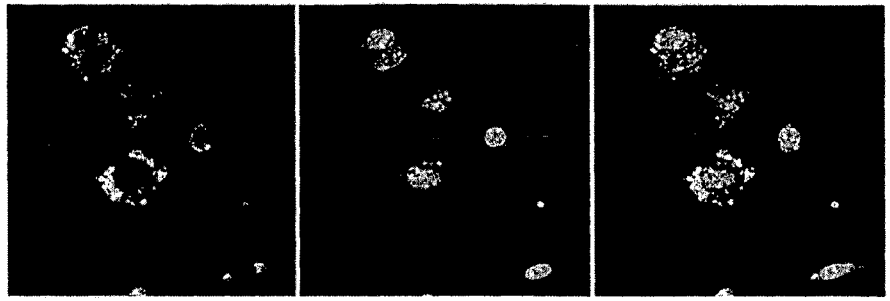
*Figure 16a*  *Figure 16b*  *Figure 16c*
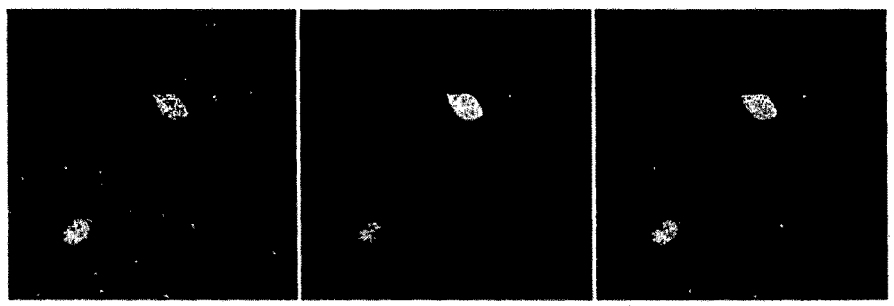
*Figure 17a*  *Figure 17b*  *Figure 17c*
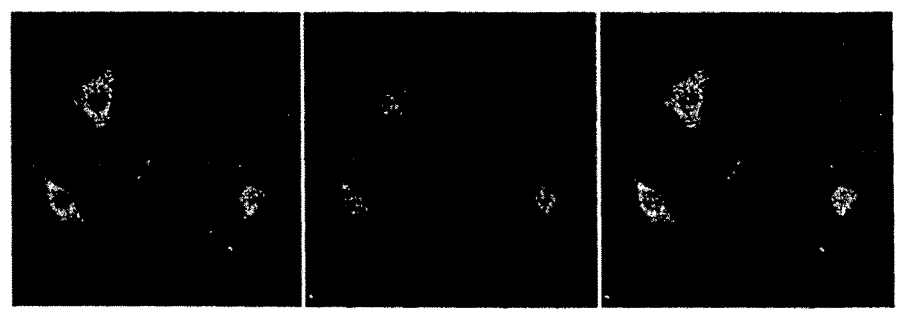
*Figure 18a*  *Figure 18b*  *Figure 18c*

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
tttaaccaag ggcggtgagc ag                                              22

<210> SEQ ID NO 2
<211> LENGTH: 24
<212> TYPE: DNA
<213> ORGANISM: Artificial Sequence

```
<220> FEATURE:
<223> OTHER INFORMATION: Synthetic primer

<400> SEQUENCE: 2
tctcggattt cccaagcaaa gatg                                              24

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tcatcttcct ccagcacctc                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ccgtagatct cgctcaccag                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gcctgagcct ttgccttcac                                                   20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
atgttgctga tgcccgcag                                                    19

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gctgctgcta ttcaggctca ctac                                              24

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
gttggacatt acctcgtggc tg                                                22
```

-continued

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
ccgggcaccg cttacaggac a                                              21

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
tcgataagcg gaatacccgc caa                                            23

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
accattcctg tacagacttt ctcc                                           24

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
agtctttacc acgatgttcc tctt                                           24

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tcaagcagac gagcacaagc                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tacagtccca aagccccagc                                                20

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 15
ggcgagaaac cttaccactg t                                              21

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
tactgaactc tctctcctgg ca                                             22

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
ccaacgagaa gagtatgagg c                                              21

<210> SEQ ID NO 18
<211> LENGTH: 23
<212> TYPE: DNA
<213> ORGANISM: Artificial Sequence
<220> FEATURE:
<223> OTHER INFORMATION: Synthetic primer

<400> SEQUENCE: 18
caaaatgatg agtgacagac agg                                            23

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tctgtggtca agtccgaggc                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ttctccagtt cgcagtccag                                                20

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
cctccagcag atgcaagaa                                                 19
```

```
<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gcttgcactt catcctttgg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
accacagtcc atgccatcac                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
tccaccaccc tgttgctgta                                              20
```

METHOD OF PRODUCING MULTIPOTENT STEM CELLS

CROSS REFERENCE TO RELATED APPLICATIONS

This application is a national stage application under 35 U.S.C. 371 and claims the benefit of PCT Application No. PCT/AU2012/001525 having an international filing date of Dec. 13, 2012, which designated the United States, which PCT application claimed the benefit of Australian Application No. 2012901259 filed Mar. 29, 2012, and Australian Application No. 2011905177 filed Dec. 13, 2011, the disclosures of each of which are incorporated herein by reference.

FIELD OF THE INVENTION

The present invention relates to induced multipotent stem cells, particularly neural stem cells, and a method of producing same.

PRIORITY DOCUMENTS

The present application claims priority from:

Australian Provisional Patent Application No. 2011905177 titled "METHOD OF PRODUCING STEM CELLS" and filed on 13 Dec. 2011; and Australian Provisional Patent Application No. 2012901259 titled "METHOD OF PRODUCING STEM CELLS" and filed on 29 Mar. 2012. The entire content of each of these applications is hereby incorporated by reference.

REFERENCE TO SEQUENCE LISTING

This application contains a Sequence Listing submitted as an electronic text file named "Sequence_Listing_ST25.txt", having a size in bytes of 4.82 KB, and created on Jun. 17, 2015. The information contained in this electronic file is hereby incorporated by reference in its entirety pursuant to 37 CFR § 1.52(e)(5).

BACKGROUND TO THE INVENTION

There is enormous interest in the development of stem cells for a wide variety of uses in research, veterinary science and medicine. Amongst the potential uses is their application in cell-based therapies for treating diseased or damaged tissues (ie so-called regenerative medicine). For example, stem cells can be used to produce neural stem cells that may be able to regenerate nerve tissue damaged by spinal injury.

Central to the further development and success of regenerative medicine is the identification of safe and cost-effective sources of suitable stem cells. Thus, considerable research has been directed at developing processes for producing autologous stem cells, such as patient-specific pluripotent stem (PS) cells. One highly significant development from this research has been the finding that fibroblasts (which can be readily and, in some cases, relatively non-invasively obtained from the patient) can be reprogrammed into induced pluripotent stem cells (iPS) and induced epiblast stem cells (IEpiS)[1-10], for example, by introducing polynucleotides encoding peptide reprogramming factors, or by directly introducing polypeptide reprogramming factors (eg transcription factors and other factors associated with reprogramming, such as Oct-3/4 (Pou5fl), Sox family (eg Sox1, Sox2, Sox3, Sox15, Sox18, etc), Myc family (eg c-Myc, N-mvc, L-myc), Klf family (eg Klf1, Klf2, Klf4, Kf15, etc), Nanog, Lin28 etc). Such polynucleotide or polypeptide reprogramming factors can be introduced into cells as genetic material using viral transfection vectors (eg retroviruses), or plasmids, or be introduced as mRNA or miRNAs, or as polypeptides (eg recombinant polypeptides). However, in despite of the remarkable progress that has been made in the last five years in iPS cell research, the hope of the clinical utilisation of pluripotent stem cells for the treatment of human diseases has remained elusive, mainly due to the risks (eg potential to induce cancer) associated with viral transfection vectors and/or exogenous and potentially oncogenic transcription factors and related factors associated with reprogramming that are presently used for the induction of the pluripotent stem cells.

Recently, research has elucidated a way by which various small molecules can be used to replace certain polypeptide or polynucleotide reprogramming factors (such that fewer transcription factors can be used in the induction) so as to improve the stem cell induction efficiency and diversity in the reprogramming process[11-21,49]. Intrigued by such research, the present applicant set out to determine whether it may be possible to produce iPS using only small molecules and, thereby, enable the development of new processes for stem cell induction offering improvements in safety and, possibly, efficiency. Using a selection of one or more small molecules, the present applicant was unable to produce iPS but has been able to induce somatic cells such as fibroblasts into multipotent cells such as neural stem cells without the use of any polynucleotide or polypeptide reprogramming factors such as viral transgenic vectors and/or oncogenic transcription factors. The resultant small molecule-induced neural stem (SMINS) cells closely resemble native neural stem (NS) cells in morphology, gene expression patterns, self-renewal and multipotency.

SUMMARY OF THE INVENTION

In a first aspect, the present invention provides a method of producing a multipotent stem cell, said method comprising culturing at least one fibroblast cell in the presence of an effective amount of at least one small molecule reprogramming factor(s) that induces the cell to de-differentiate into a multipotent stem cell, wherein the method excludes the use of reprogramming factor(s) that are not small molecules.

In embodiments, the small molecule reprogramming factor(s) is selected from the group consisting of a G9a HMTase inhibitor(s) and a MEK inhibitor(s).

In embodiments, the small molecule reprogramming factor(s) is a G9a HMTase inhibitor(s). In embodiments, the G9a HMTase inhibitor(s) is in combination with an effective amount of at least one further small molecule reprogramming factor (s) selected from the group consisting of a histone deacetylase (HDAC) inhibitor(s), a MEK inhibitor(s), a DNA methyltransferase inhibitor(s), a glycogen synthase kinase 3 (GSK3) inhibitor(s), Vitamin C, and a Activin receptor-like kinase (ALK) receptor inhibitor(s). In embodiments, the G9a HMTase inhibitor(s) is in combination with a DNA methyltransferase inhibitor(s). In embodiments, the G9a HMTase inhibitor(s) is in combination with a DNA methyltransferase inhibitor(s) and a MEK inhibitor(s).

In embodiments, the small molecule reprogramming factor(s) is a MEK inhibitor(s). In embodiments, the MEK inhibitor(s) is in combination with an effective amount of at least one further small molecule reprogramming factor(s)

selected from the group consisting of a HDAC inhibitor(s), a G9a HMTase inhibitor(s), a DNA methyltransferase inhibitor(s) a GSK3 inhibitor(s). Vitamin C, and an ALK receptor inhibitor(s).

In embodiments, the G9a HMTase inhibitor(s) is 2-(hexahydro-4-methyl-1H-1,4-diazepin-1-yl)-6,7-dimethoxy-N-[1-(phenylmethyl)-4-piperidinyl]-4-quinazolinamine trihydrochloride hydrate (BIX01294). In embodiments, the DNA methyltransferase inhibitor(s) is 1H-Indole-3-propanoic acid, α-(1,3-dihydro-1,3-dioxo-2H-isoindol-2-yl)-, (αS)— (RG108). In embodiments, the MEK inhibitor(s) is N-(2,3-dihydroxy-propoxy)-3,4-difluoro-2-(2-fluoro-4-iodo-phenylamino)-benzamide (PD325901).

In embodiments, the multipotent stem cell is a neural stem cell. In embodiments, the multipotent stem cell is a human cell.

In embodiments, the culturing comprises:

(a) performing an at least one induction cycle comprising culturing for approximately one day the at least one fibroblast cell in the presence of an effective amount of at least one small molecule reprogramming factor(s) that induces the cell to de-differentiate into a multipotent stem cell, and then culturing for approximately two days the at least one cell in the absence of said effective amount of at least one small molecule reprogramming factor(s), and optionally (b) culturing the at least one cell of step (a) in media adapted to support multipotent stem cell growth for a suitable period.

In a second aspect, the present invention provides a method for producing a differentiated cell, said method comprising culturing a multipotent stem cell produced by the method of the first aspect under conditions suitable for differentiation of said multipotent stem cell into a differentiated cell selected from the group consisting of an astrocyte, a neuron and an oligodendrocyte.

In a third aspect, the present invention provides a neural stem cell in a substantially isolated form, said cell characterised in that it expresses the neural stem cell markers ALP, Sox2 and SSEA1 and the neural stem cell marker genes Sox2, GFAP, Pax6 and Olig2, but does not express the pluripotent genes Oct4 and Nanog.

In a fourth aspect, the present invention provides a neural stem cell in a substantially isolated form, said cell characterised in that it expresses the neural stem cell markers ALP, Sox2 and SSEA1 and the neural stem cell marker genes Sox2, GFAP, Nestin and Olig2, but does not express the pluripotent genes Oct4 and Nanog.

In a fifth aspect, the present invention provides a differentiated cell in accordance with the present invention.

In a sixth aspect, the present invention provides an assay for determining the effect of a drug candidate on a cell, said method comprising culturing a differentiated cell produced by the method the first or second aspect in the presence of said drug candidate.

In a seventh aspect, the present invention provides a kit for use in the method of the first aspect, said kit comprising a G9a HMTase inhibitor(s) and, optionally, one or more small molecule reprogramming factor(s) selected from the group consisting of a DNA methyltransferase inhibitor(s), a MEK inhibitor(s), a HDAC inhibitor(s), a GSK3 inhibitor(s), Vitamin C; and a ALK receptor inhibitor(s); together with a suitable culture medium.

In an eight aspect, the present invention provides a kit for use in the method of the first aspect, said kit comprising a MEK inhibitor(s) and, optionally, one or more small molecule reprogramming factor(s) selected from the group consisting of a DNA methyltransferase inhibitor(s), a G9a HMTase inhibitor(s), a HDAC inhibitor(s), a GSK3 inhibitor(s), Vitamin C; and a ALK receptor inhibitor(s); together with a suitable culture medium.

In a ninth aspect, the present invention provides a kit for use in the second aspect, said kit comprising the small molecule reprogramming factor(s) in combination with other factors required for the differentiation of the cells together with a suitable culture medium and, optionally, instructions for said use.

In a tenth aspect, the present invention provides a kit for use in the assay of the fifth aspect, said kit comprising a suitable culture medium together with reagents for assessing an effect of a drug candidate upon the cells and, optionally, instructions for said use.

BRIEF DESCRIPTION OF THE FIGURES

FIG. 8 provides graphical results of human umbilical cord fibroblast (HUCF) cells during p75-NTR FACS sorting (a) forward and side scatter plot of cells showing populations positive and negative for p75NTR, and (b) plot showing purity of p75-NTR⁻ sorted cells; and (c) immunofluorescence micrograph image of p75-NTR⁻ sorted cells following staining with anti-p75-NTR and DAPI;

FIG. 13 provides immunofluorescence micrographs of cells induced from HUCF using BIX01294 and RG108 in HIPS media for one day and HIPS media (no small molecules) for two days (in the absence of culture in NSC media), stained for (a) Sox 2, (b) DAPI, and (c) Sox2 and DAPI combined image;

FIG. 14 provides immunofluorescence micrographs of cells induced from HUCF using BIX01294 and RG108 in HIPS media for one day and HIPS media (no small molecules) for two days (in the absence of culture in NSC media), stained for (a) SSEA-1, (b) DAPI, and (c) SSEA-1 and DAPI combined image;

FIG. 15 provides immunofluorescence micrographs of cells induced from HUCF using BIX01294 alone in HIPS media for one day and HIPS media (no small molecules) for two days followed by culturing in NSC media, stained for (a) Sox 2, (b) DAPI and (c) Sox2 and DAPI combined image;

FIG. 16 provides immunofluorescence micrographs of cells induced from HUCF using BIX01294 alone in HIPS media for one day and HIPS media (no small molecules) for two days followed by culturing in NSC media, stained for (a) SSEA-1, (b) DAPI, and (c) SSEA-1 and DAPI combined image;

FIG. 17 provides immunofluorescence micrographs of cells induced from HUCF using BIX01294 alone in HIPS media for one day and HIPS media (no small molecules) for two days (in the absence of culture in NSC media), stained for (a) Sox 2, (b) DAPI, and (c) Sox2 and DAPI combined image;

FIG. 18 provides immunofluorescence micrographs of cells induced from HUCF using BIX01294 alone in HIPS media for one day and HIPS media (no small molecules) for two days (in the absence of culture in NSC media), stained for (a) SSEA-1, (b) DAPI, and (c) SSEA-1 and DAPI combined image;

DETAILED DESCRIPTION OF THE INVENTION

Figure 1A:
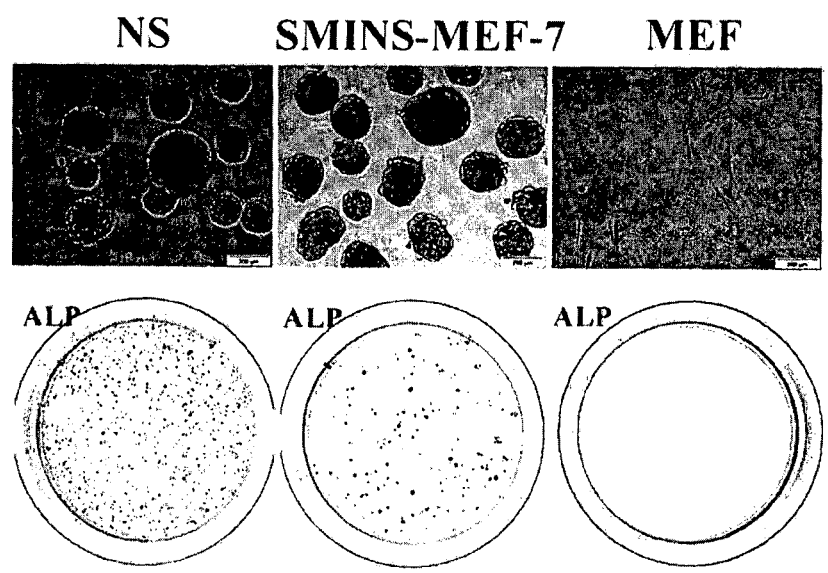
FIG. 1 provides (a) images showing the morphology of native neural stem cells (NS), "small molecule-induced neural stem cells from mouse embryonic fibroblasts (MEF) with seven small molecules" cells (SMINS-MEF-7) and mouse embryonic fibroblasts (MEF) under bright field microscopy following alkaline phosphatase (ALP) staining, scale bar: 200 μm; and (b) a schematic representation of the protocol for the production of small molecule-induced neural stem (SMINS) cells using six induction cycles.

The present applicant has identified a novel and safe method to efficiently induce neural stem cells from somatic cells such as fibroblasts using only one or more selected small molecules for the induction. By eliminating the concerns of integrating potentially harmful viral transfection vectors and/or the introduction of polynucleotide or polypeptide reprogramming factors such as oncogenic transcription factors, this method may represent an important step forward towards the tailoring of individualised cell-based therapies for subjects with neurodegenerative diseases and other nerve damage.

Accordingly, in a first aspect, the present invention provides a method of producing a multipotent stem cell, said method comprising culturing at least one fibroblast cell in the presence of an effective amount of at least one small molecule reprogramming factor that induces the cell to de-differentiate into a multipotent stem cell, wherein the method excludes the use of reprogramming factor(s) that are not small molecules.

As used herein, the term "reprogramming factor" is intended to refer to a molecule that is associated with cell differentiation or de-differentiation into a different cell type, for example, from a somatic cell to a stem cell. Reprogramming factors generally affect expression of genes associated with cell differentiation or de-differentiation. Transcription factors are examples of reprogramming factors.

The person skilled in the art will appreciate that "differentiation" in the context of the present invention refers to the process by which a less specialised cell (ie a more naïve cell) becomes a more specialised cell type, and that the term "de-differentiation" refers to the process by which a more specialised cell becomes a less specialised cell type (ie a more naïve cell).

As used herein, the term "small molecule" is to be understood as referring to a low molecular weight, organic compound that has a biological function, as would be understood by the person skilled in the art. By definition, a small molecule is not a polymer, unless it is a very small oligomer (eg consisting of two or possibly three monomers). Accordingly, a small molecule is not a polynucleotide or polypeptide such as a gene, a primer, transposon, or other DNA polynucleotide molecule, an RNA polynucleotide molecule that encodes a protein or polypeptide (eg double-stranded RNA, mRNA (ie sense RNA), or the complement to mRNA (ie antisense strand of a RNA duplex)), a micro-RNA (miRNA) molecule or interfering RNA (RNAi) molecule, or other RNA polynucleotide molecule, or a polypeptide, or a fragment of any of these polynucleotide or polypeptide molecules, unless said fragment is a monomer or a very small oligomer such as a dinucleotide, dipeptide or tripeptide. The upper molecular weight limit for a small molecule is generally considered to be approximately 800 g/mol (ie approximately 800 Daltons). However, the person skilled in the art will appreciate that a small molecule could have an upper molecular weight limit of approximately 900 g/mol. A small molecule generally binds in a specific manner to a biopolymer such as a polypeptide or polynucleotide molecule, etc, and alters the activity or function of that polypeptide or polynucleotide molecule (eg activates or inhibits the function of a particular enzyme, etc). In the method of the present invention, all of the reprogramming factors used to induce multipotent cells from somatic cells are small molecules. In embodiments, the small molecule reprogramming factor(s) of the present invention may be selected from the group consisting of include G9a histone methyltransferase (G9a HMTase) inhibitor(s), DNA methyltransferase inhibitor(s), MEK inhibitor(s), histone deacetylase (HDAC) inhibitor(s), glycogen synthase kinase 3 (GSK3) inhibitor(s), Vitamin C and Activin receptor-like kinase (ALK) receptor inhibitor(s), wherein the small molecule reprogramming factor(s) has a molecular weight of less than 800 g/mol. In embodiments, the small molecule reprogramming factor(s) has a molecular weight of less than 900 g/mol. In embodiments, the small molecule reprogramming factor(s) has a molecular weight of less than 800 g/mol. In embodiments, the small molecule reprogramming factor(s) has a molecular weight of less than 700 g/mol. In embodiments, the small molecule reprogramming factor(s) has a molecular weight of 600 g/mol or less.

A "polynucleotide or polypeptide reprogramming factor" as used herein is to be understood as referring to a polynucleotide or polypeptide molecule that is associated with reprogramming cells (eg somatic cells) to be more naïve, for example, to induce somatic cells to be multipotent or pluripotent cells. It is to be understood that the polynucleotide or polypeptide reprogramming factor could, for example be a gene, a primer, transposon, or other DNA polynucleotide molecule, an RNA polynucleotide molecule that encodes a protein or peptide (eg double-stranded. RNA, mRNA (ie sense RNA), or the complement to mRNA (ie antisense strand of a RNA duplex)), a microRNA (miRNA) molecule or interfering RNA (RNAi) molecule, or other RNA polynucleotide molecule, or a polypeptide, or a fragment of any of these polynucleotide or polypeptide molecules, providing said fragment is not a monomer or a very small oligomer such as a dinucleotide, dipeptide or tripeptide.

Methods of inducing somatic cells to be induced pluripotent stem cells (eg iPSC) or other more naïve cell types (eg induced multipotent stem cells) using one or more exogenous polynucleotide or polypeptide reprogramming factors are known to the person skilled in the art. Such methods may rely members on the introduction of genetic material encoding one or more transcription factor(s) or other polypeptide(s) associated with cell reprogramming (eg inducing pluripotency), such as Oct-3/4 (Pou5fl), Sox family members (eg Sox1, Sox2, Sox3, Sox15, Sox18, etc), Myc family members (eg c-Myc, N-myc, L-myc), Klf family members (eg Klf1, Klf2, Klf4, Kf15, etc), Nanog, Lin28, etc, or functional fragments thereof. In some methods, exogenous polypeptides (eg recombinant polypeptides) encoded by the reprogramming genes (eg the above genes) are contacted with the cells to induce pluripotent stem cells. The person skilled in the art will appreciate that other genes may be associated with reprogramming of cells, and exogenous molecules encoding such genes (or functional fragments thereof) and the encoded polypeptides are also considered to be polynucleotide or polypeptide reprogramming factors (eg polynucleotides or polypeptides that in turn affect expression levels of another gene associated with cell reprogramming). For example, it has been shown that the introduction of exogenous polynucleotide or polypeptide epigenetic gene silencers that decrease p53 inactivation increase the efficiency of inducing iPSC. Accordingly, exogenous polynucleotides or polypeptides encoding epigenetic silencers and other genes or proteins that may be directly or indirectly involved in cell reprogramming or increasing cell programming efficiency would be considered to constitute an exogenous polynucleotide or polypeptide reprogramming factor. The person skilled in the art will appreciate that other methods of influencing cell reprogramming exist, such as introducing RNAi molecules (or genetic material encoding RNAi molecules) that can knock down expression of genes involved in inhibiting cell reprogramming. Accordingly, any exogenous polynucleotide molecule or polypeptide molecule that is associated with cell reprogramming, or enhances cell reprogramming, is to be understood to be an exogenous polynucleotide or polypeptide reprogramming factor as described herein.

The method of the present invention does not involve a culturing step of the cell(s) with one or more exogenous polynucleotide or polypeptide reprogramming factor(s). Accordingly, the method of the present invention does not involve the introduction of one or more exogenous polynucleotide or polypeptide reprogramming factor(s), eg by introducing transposons, viral transgenic vectors (such as retroviral vectors), plasmids, mRNA, miRNA, peptides, or fragments of any of these molecules), that are involved in producing iPS or, otherwise, inducing multipotent stem cells such as neural stem cells from somatic cells such as fibroblast cells[48]. In fact, the method of the present invention does not involve contacting cells with any exogenous polynucleotide or polypeptide molecule, other than those that are routinely found in tissue culture media or stem cell media (eg foetal bovine serum (FBS), leukaemia inhibitory factor (LIF), epidermal growth factor (EGF), basic fibroblast growth factor (bFGF), etc).

Instead, the method utilises an effective amount of at least one small molecule reprogramming factor(s) to induce reprogramming of a somatic cell into a multipotent stem cell, in the absence of one or more exogenous polynucleotide or polypeptide reprogramming factor(s). Accordingly, it is to be understood that the method of the present invention utilises only small molecules to reprogram somatic cells into induced multipotent stem cells, without the addition of polypeptide transcription factors, other polypeptide factors specifically associated with inducing pluripotency, polynucleotide sequences encoding polypeptide transcription factors, polynucleotide sequences encoding other polypeptide factors specifically associated with inducing pluripotency, mRNA, interference RNA, microRNA and fragments thereof. Notably, the method of the present invention does not include the addition of one or more polynucleotides or polypeptides selected from the group consisting of such as Oct-3/4 (Pou5fl), Sox family members (eg Sox1, Sox2, Sox3, Sox15, Sox18, etc), Myc family members (eg c-Myc, N-myc, L-myc), Klf family members (eg Klf1, Klf2, Klf4, Kf15, etc), Nanog, Lin28, etc, and functional fragments thereof.

As used herein, the term "multipotent" is to be understood as referring to a cell (eg a stem cell or an induced stem cell) that has the ability to give rise to cells from a multiple, but limited, number of lineages, such as haematopoietic stem cells, cardiac cells, or neural stem cells. For example, a haematopoietic stem cell has the ability to differentiate into a number of different types of blood cells, but cannot develop into cells of other tissue types; whereas a cardiac stem cell has the ability to differentiate into a number of different cells of the cardiac system, such as myocytes, smooth muscle cells and endothelial cells. In another example, a neural stem cell has the ability to differentiate into a number of cells of the nervous system, such as neurons, astrocytes, and oligodendrocytes. It is to be understood that multipotent cells are entirely distinct from pluripotent cells. As used herein, the term "pluripotent" is to be understood as referring to a cell (eg a stem cell) that has the potential to differentiate into cells of any of the three germ layers, that is, endoderm (interior stomach lining, gastrointestinal tract, the lungs), mesoderm (muscle, bone, blood, urogenital), or ectoderm (epidermal tissues and nervous system). Accordingly, the induced multipotent cells of the present invention are distinct from induced pluripotent stem cells (iPS).

The fibroblast cell(s) may be of human or other animal origin (eg mouse, rat, rabbit, cat, dog, horse and non-human primates), and may be selected from fibroblasts derived from, for example, the dermis[2], oral gingiva, umbilical cord and connective tissue (eg from cartilage, adipose, haematopoietic tissue and lymphatic tissue). Alternatively, the fibroblast cell(s) may be derived through de-differentiation of epithelial cells by a process known as epithelial-to-mesenchymal transition (EMT), as well as bone marrow- and tissue-derived mesenchymal stem cells. In some embodiments, the fibroblast cell(s) will be isolated from a subject and utilised in the method of the first aspect of the invention so as to produce autologous multipotent stem cells for use in said subject. However, the produced multipotent stem cell may be used in other applications, such as stem cell implantation, gene therapy or other "off-the-shelf" applications, wherein heterologous stem cells are produced for use in said subject.

In embodiments, the method of the first aspect comprises culturing at least one fibroblast cell in the presence of a small molecule reprogramming factor(s) consisting of a histone methyltransferase (HMTase) inhibitor(s). HMTases, are histone-modifying enzymes, (including histone-lysine N-methyltransferase and histone-arginine N-methyltransferase), that catalyse the transfer of one, two, or three methyl groups to lysine and arginine residues of histone proteins. Two major types of HMTases exist, lysine-specific (which can be SET (Su(var)3-9, Enhancer of Zeste, Trithorax) domain containing or non-SET domain containing) and arginine-specific. HMTase inhibitors are known to target the function of G9a HMTase (eg Bix-01294, UNC0638, BRD4770), Dot1L HMTase (eg EPZ004777), SMYD2 HMTase (eg AZ505), EZH2 HMTase, Set7/9 HMTase (eg PDB4e47). Accordingly, the person skilled in the art will appreciate that the above list of HMTase inhibitors is not exhaustive and that other small molecule HMTase inhibitors may be suitable for use in the present invention. In embodiments, the histone methyltransferase (HMTase) inhibitor(s) is a G9aHMTase inhibitor(s).

In embodiments, the method of the first aspect comprises culturing at least one fibroblast cell in the presence of a small molecule reprogramming factor(s) selected from the group consisting of G9a HMTase inhibitor(s) and a MEK inhibitor(s). In embodiments, the small molecule reprogramming factor(s) is a G9a HMTase inhibitor(s). In embodiments, the small molecule reprogramming factor(s) is a MEK inhibitor(s).

G9a HMTase inhibitors impair G9a HMTase and the generation of H3K9me2 in vitro[39]. G9a HMTase regulates gene expression including one of the pluripotency genes, Oct4[40]. Suitable G9a HMTase inhibitors for use in the present invention include UNC0224 (7-[3-(dimethylamino)propoxy]-2-(hexahydro-4-methyl-1H-1,4-diazepin-1-yl)-6-methoxy-N-(1-methyl-4-piperidinyl)-4-quinazolinamine: molecular weight=485.7 g/mol) and Chaetocin (2,2',3S,3'S,5aR,5'aR,6,6'-octahydro-3,3'-bis(hydroxymethyl)-2,2'-dimethyl-[10bR,10'bR(11aS,11'aS)-bi-3,11a-epidithio-11aH-pyrazino[1',2':1,5]pyrrolo[2,3-b]indole]-1,1',4,4'-tetrone; molecular weight=696.8 g/mol). However, preferably, the G9a HMTase inhibitor known as BIX01294 (also known as 2-(hexahydro-4-methyl-1H-1,4-diazepin-1-yl)-6,7-dimethoxy-N-[1-(phenylmethyl)-4-piperidinyl]-4-quinazolinamine trihydrochloride hydrate; molecular weight=600.02 g/mol) is used. BIX01294 has previously been found to improve the efficiency of cell reprogramming by some induction processes to a level substantially equivalent to processes involving the use of the four transcription factors Oct4, Klf4, Sox2 and c-Myc[40]. Other suitable G9a HMTase inhibitors may include those shown in Table 1. However, the person skilled in the art will appreciate that the list in Table 1 is not exhaustive and that other small molecule G9a HMTase inhibitors may be suitable for use in the present invention.

TABLE 1

Small molecule G9a HMTase inhibitors

| Chemical name | Synonyms | Molecular weight (g/mol) |
|---|---|---|
| 2-(hexahydro-4-methyl-1H-1,4-diazepin-1-yl)-6,7-dimethoxy-N-[1-(phenylmethyl)-4-piperidinyl]-4-quinazolinamine trihydrochloride hydrate | BIX01294 | 600.0 |
| 7-[3-(dimethylamino)propoxy]-2-(hexahydro-4-methyl-1H-1,4-diazepin-1-yl)-6-methoxy-N-(1-methyl-4-piperidinyl)-4-quinazolinamine | UNC0224 | 485.7 |
| 2,2',3S,3'S,5aR,5'aR,6,6'-octahydro-3,3'-bis(hydroxymethyl)-2,2'-dimethyl-[10bR,10'bR(11aS,11'aS)-bi-3,11a-epidithio-11aH-pyrazino[1',2':1,5]pyrrolo[2,3-b]indole]-1,1',4,4'-tetrone | Chaetocin | 696.8 |
| 2-Cyclohexyl-N-(1-isopropylpiperidin-4-yl)-6-methoxy-7-(3-(pyrrolidin-1-yl)propoxy) quinazolin-4-amine | UNC0638 | 509.73 |
| Methyl-2-benzamido-1-(3-phenylpropyl)-1H-benzo[d]imidazole-5-carboxylate | BRD4770 | 413.5 |
| 1-(4-(4-methoxybenzoyloxy)phenethyl)-2-(4-(trifluoromethyl)benzamido)-1H-benzo[d]imidazole-5-carboxylic acid, Hydrate, 1-(2-(4-(4-Methoxybenzoyloxy)phenyl)ethyl)-2-(4-trifluoromethylbenzoylamino)-1H-benzoimidazole-5-carboxylic acid, Hydrate | BIX-01338 | 621.6 |

In embodiments, the G9a HMTase inhibitor may be represented by formula I:

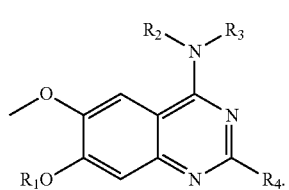

wherein:

$R_1$ is selected from the group consisting of: optionally substituted $C_1$-$C_{12}$alkyl, optionally substituted $C_2$-$C_{12}$heteroalkyl, optionally substituted $C_2$-$C_{12}$heterocycloalkyl;

$R_2$ and $R_3$ are each independently selected from the group consisting of: H, optionally substituted $C_3$-$C_{12}$cycloalkyl, and optionally substituted $C_2$-$C_{12}$heterocycloalkyl; and $R_4$ is selected from the group consisting of: optionally substituted $C_3$-$C_{12}$cycloalkyl, and optionally substituted $C_2$-$C_{12}$heterocycloalkyl.

In embodiments, $R_1$ is optionally substituted $C_1$-$C_3$alkyl. In specific embodiments, $R_1$ is methyl. In other specific embodiments, $R_1$ is amino substituted $C_3$alkyl, wherein the amino group is an alkylamino group or an aminocycloalkyl.

The alkylamino may be dimethylamino. The aminocycloalkyl group may be pyrrolidine.

In embodiments, $R_2$ is H and $R_3$ is optionally substituted $C_2$-$C_{12}$heterocycloalkyl. In specific embodiments, $R_3$ is optionally substituted $C_2$-$C_{12}$heterocycloalkyl. The $C_2$-$C_{12}$heterocycloalkyl group may be an N-substituted morpholin-4-yl group wherein the N substitutent is selected from methyl, prop-2-yl, and benzyl.

In embodiments, $R_4$ is selected from the group consisting of cyclohexyl and 4-substituted azepan-1-yl. The 4-substituted azepan-1-yl may be 4-methylazepan-1-yl.

Examples of G9aHMTase inhibitors represented by Formula I include BIX01294, UNC0224, and UNC0638.

In embodiments, the G9a HMTase inhibitor may be represented by formula II:

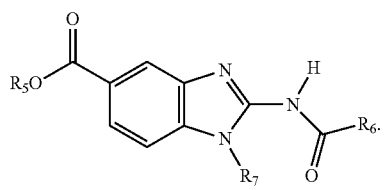

wherein:
$R_5$ is selected from the group consisting of: H and optionally substituted $C_1$-$C_{12}$alkyl;
$R_6$ is selected from the group consisting of: optionally substituted $C_1$-$C_{12}$alkyl and optionally substituted $C_6$-$C_{18}$aryl; and
$R_7$ is optionally substituted $C_1$-$C_{12}$alkyl.

In specific embodiments, $R_5$ is methyl. In other specific embodiments, $R_5$ is H.

In embodiments, $R_6$ is optionally substituted phenyl. The optional substituent may be methyl or trifluoromethyl. The optional substituent may be in the para position.

In embodiments, $R_7$ is optionally substituted ethyl or optionally substituted n-propyl. The substituent may be a phenyl or substituted phenyl. The substituent may be a p-methoxybenzoyl group. The substituent may be in the para position.

Examples of G9aHMTase inhibitors represented by Formula II include Bix01338 and BRD4770.

The person skilled in the art will understand that an effective amount of a G9a HMTase inhibitor may vary depending upon, for example, the particular selected G9a HMTase inhibitor or combination of G9a HMTase inhibitors employed, and the particular fibroblast cell(s). However, generally, the G9a HMTase inhibitor(s) will be provided for the culturing of the fibroblast cell(s) at a concentration in the range of 0.001 to 10 µM, preferably 0.01 to 2.0 µM. The preferred concentration of the G9a HMTase inhibitor may vary depending on which G9a HMTAse inhibitor is used. For example, for chaetocin, the preferred concentration may be in the range of 0.001 to 1.0 µM, more preferably 0.009 to 0.5 µM, more preferably approximately 0.01 to 0.2 µM. In another example, for BIX01294, the preferred concentration is approximately 1 µM. Typically, the effective amount of the G9a HMTase inhibitor(s) will be provided in a culture medium suitable for the culture of fibroblast cells.

In some embodiments of the present invention, the method may comprise culturing the fibroblast cell(s) with a combination of two or more different G9a HMTase inhibitors.

The G9a HMTase inhibitor(s) may also be used in combination with one or more small molecule reprogramming factor(s) selected from:
(i) HDAC inhibitors;
(ii) MEK inhibitors;
(iii) DNA methyltransferase inhibitors;
(iv) GSK3 inhibitors;
(v) Vitamin C; and
(vi) ALK receptor inhibitors.

In embodiments, the G9a HMTase inhibitor(s) is in combination with a DNA methyltransferase inhibitor(s). In embodiments, the G9a HMTase inhibitor(s) is in combination with a DNA methyltransferase inhibitor(s) and a MEK inhibitor(s). In embodiments, the method comprises culturing at least one fibroblast cell in the presence of an effective amount of BIX01294, wherein the method excludes the use of reprogramming factor(s) that are not small molecules. In another embodiment, the method comprises culturing at least one fibroblast cell in the presence of an effective amount of BIX01294 and RG108, wherein the method excludes the use of reprogramming factor(s) that are not small molecules. In a further embodiment, the method comprises culturing at least one fibroblast cell in the presence of an effective amount of BIX01294, RG108 and PD325901, wherein the method excludes the use of reprogramming factor(s) that are not small molecules.

MEK inhibitors are compounds that target mitogen-activated protein kinase (MAPK/ERK kinase or MEK) so as to block the MEK (ERK1/2) signalling pathway. Suitable MEK inhibitors for use in the method of the first aspect of the invention include the benzohydroxamate MEK inhibitors such as 2-(2-chloro-4-iodo-phenylamino)-N-cyclopropylmethoxy-3,4-difluoro-benzamide (also known as CI-1040 or PD184352; molecular weight=478.67 g/mol), N-(2,3-dihydroxy-propoxy)-3,4-difluoro-2-(2-fluoro-4-iodo-phenylamino)-benzamide (which selectively binds and inhibits MEK and, in turn, is believed to inhibit the phosphorylation and activation of MAPK/ERK)[34-36] (also known as PD325901 or PD0325901; molecular weight=482.19 g/mol), and related compounds as described in, for example, U.S. Pat. No. 6,960,614, the contents of which are herein incorporated by reference. Other suitable MEK inhibitors may include those shown in Table 2. However, the person skilled in the art will appreciate that the list in Table 2 is not exhaustive and that other small molecule MEK inhibitors may be suitable for use in the present invention.

TABLE 2

| Small molecule MEK inhibitors | | |
|---|---|---|
| Chemical name | Synonyms | Molecular weight (g/mol) |
| 2-(2-chloro-4-iodo-phenylamino)-N-cyclopropylmethoxy-3,4-difluoro-benzamide | CI-1040, PD184352 | 478.67 |

TABLE 2-continued

Small molecule MEK inhibitors

| Chemical name | Synonyms | Molecular weight (g/mol) |
|---|---|---|
| N-(2,3-dihydroxy-propoxy)-3,4-difluoro-2-(2-fluoro-4-iodo-phenylamino)-benzamide | PD325901, PD0325901 | 482.19 |
| [3,4-difluoro-2-[(2-fluoro-4-iodophenyl)amino]phenyl][3-hydroxy-3-[(2S)-2-piperidinyl]-1-azetidinyl]methanone | GDC 0973, XL 518 | 531.31 |
| 6-(4-bromo-2-chlorophenylamino)-7-fluoro-N-(2-hydroxyethoxy)-3-methyl-3H-benzo[d]imidazole-5-carboxamide | AZD6244, Selumetinib, ARRY-142886 | 457.68 |
| (2Z,3Z)-2,3-bis(amino(2-aminophenylthio)methylene)succinonitrile,ethanol | U0126-EtOH, UO126 EtOH, | 426.56 |
| N-(3-(3-cyclopropyl-5-(2-fluoro-4-iodophenylamino)-6,8-dimethyl-2,4,7-trioxo-3,4,6,7-tetrahydropyrido[4,3-d]pyrimidin-1(2H)-yl)phenyl)acetamide | GSK1120212, Trametinib | 615.39 |
| (R)-N-(3,4-difluoro-2-(2-fluoro-4-iodophenylamino)-6-methoxyphenyl)-1-(2,3-dihydroxypropyl)cyclopropane-1-sulfonamide | RDEA119, Refametinib, BAY 869766 | 572.33 |
| 5-bromo-N-(2,3-dihydroxypropoxy)-3,4-difluoro-2-(2-fluoro-4-iodophenylamino)benzamide | PD318088 | 561.09 |
| (S)-N-(2,3-dihydroxypropyl)-3-(2-fluoro-4-iodophenylamino)isonicotinamide | AS703026 | 431.20 |
| 2-(2-fluoro-4-iodophenylamino)-N-(2-hydroxyethoxy)-1,5-dimethyl-6-oxo-1,6-dihydropyridine-3-carboxamide | AZD8330 | 461.23 |
| (R)-3-(2,3-dihydroxypropyl)-6-fluoro-5-(2-fluoro-4-iodophenylamino)-8-methylpyrido[2,3-d]pyrimidine-4,7(3H,8H)-dione | TAK-733 | 504.23 |
| 3,4-difluoro-2-((2-fluoro-4-iodophenyl)amino)-N-(2-hydroxyethoxy)-5-((3-oxo-1,2-oxazinan-2-yl)methyl)benzamide | CH4987655, RO4987655 | 565.28 |
| 5-[(4-Bromo-2-fluorophenyl)amino]-4-fluoro-N-(2-hydroxyethoxy)-1-methyl-1H-benzimidazole-6-carboxamide | ARRY-162, MEK-162, ARRY-438162 | 441.23 |
| 2-(2-amino-3-methoxyphenyl)-4H-chromen-4-one; or 2'-Amino-3'-methoxyflavone | PD98059, CAS 167869-21-8 | 267.28 |
| (Z)-3-amino-3-(2-aminophenyl)sulfanyl-2-[3-[hydroxy(pyridin-4-yl)methyl]phenyl]prop-2-enenitrile | CHEMBL37493, CHEBI:151234, HMS3229K14, CAS 297744-42-4 | 374.45 |
| 2-Chloro-3-(N-succinimidyl)-1,4-naphthoquinone | CAS 623163-52-0 | 289.67 |
| N-Cyclopropylmethoxy-3,4,5-trifluoro-2-(4-iodo-2-methylphenylamino)benzamide | CAS 212631-61-3 | 476.2 |
| 2-(2-Chloro-4-iodo-phenylamino)-N-cyclopropylmethoxy-3,4-difluoro-5-bromo-benzamide | CAS 212631-67-9 | 557.6 |
| 1,4-Diamino-2,3-dicyano-1,4-bis(2-aminophenylthio)butadiene | U0126, CAS 109511-58-2 | 403.5 |
| E-α-(Amino-((4-aminophenyl)thio)methylene)-2-(trifluoromethyl)benzeneacetonitrile | CAS 305350-87-2 | 335.4 |

In some embodiments of the present invention, the method may comprise culturing the fibroblast cell(s) with a combination of two or more different MEK inhibitors.

The person skilled in the art will understand that an effective amount of a MEK inhibitor may vary depending upon, for example, the particular selected MEK inhibitor or combination of MEK inhibitors employed, and the particular fibroblast cell(s). However, generally, the MEK inhibitor(s) will be provided for the culturing of the fibroblast cell(s) at a concentration in the range of 0.1 to 10 µM, preferably 0.2 to 2.0 µM, most preferably about 0.5 µM to 1 µM. Typically, the effective amount of the MEK inhibitor(s) will be provided in a culture medium suitable for the culture of fibroblast cells.

The MEK inhibitor(s) may also be used in combination with one or more small molecule reprogramming factor(s) selected from:
 (i) Histone deacetylase (HDAC) inhibitors;
 (ii) G9a HMTase inhibitors;
 (iii) DNA methyltransferase inhibitors;
 (iv) Glycogen synthase kinase 3 (GSK3) inhibitors;
 (v) Vitamin C; and
 (vi) Activin receptor-like kinase (ALK) receptor inhibitors.

In embodiments, the MEK inhibitor(s) is in combination with a G9a HMTase inhibitor(s). In embodiments, the MEK inhibitor(s) is in combination with a DNA methyltransferase inhibitor(s). In embodiments, the MEK inhibitor(s) is in combination with a DNA methyltransferase inhibitor(s) and a G9a HMTase inhibitor(s). In embodiments, the method comprises culturing at least one fibroblast cell in the presence of an effective amount of PD325901, wherein the method excludes the use of reprogramming factor(s) that are not small molecules. In another embodiment, the method comprises culturing at least one fibroblast cell in the presence of an effective amount of PD325901 and BIX01294, wherein the method excludes the use of reprogramming factor(s) that are not small molecules. In a further embodiment, the method comprises culturing at least one fibroblast cell in the presence of an effective amount of PD325901 and RG108, wherein the method excludes the use of reprogramming factor(s) that are not small molecules. In still a further embodiment, the method comprises culturing at least one fibroblast cell in the presence of an effective amount of BIX01294, RG108 and PD325901, wherein the method excludes the use of reprogramming factor(s) that are not small molecules.

Suitable DNA methyltransferase inhibitors for use in the present invention include zebularine (1H-β-D-ribofuranosyl-2-pyrimidinone; molecular weight=228.20 g/mol), decitabine(4-amino-1-(2-deoxy-b-D-erythro-pentofuranosyl)-1,3,5-triazin-2(1H)-one (or 2'-Deoxy-5-azacytidine, 4-Amino-1-(2-deoxy-β-D-ribofuranosyl)-1,3,5-triazin-2 (1H)-one; also known as 5-aza-2'-deoxycytidine or dacogen; molecular weight=228.21 g/mol), and 2',3',5'-triacetyl-5-azacytidine (4-amino-1-(2,3,5-tri-O-acetyl-β-D-ribofuranosyl)-1,3,5-triazin-2(1H)-one (or 4-Amino-1-(β-D-ribofuranosyl)-1,3,5-triazin-2(1H)-one; also known as 5-azacytidine; 5-azacitidine, Azacitidine, Vidaza, Mylosar or Ladakamycin; molecular weight=244.2 g/mol). However, preferably, the present invention utilises N-phthalyl-L-tryptophan (1H-Indole-3-propanoic acid, α-(1,3-dihydro-1,3-dioxo-2H-isoindol-2-yl)-, (αS)—; also known as RG108; molecular weight=334.33 g/mol) or a related compound. RG108 is a cell-permeable molecule that specifically inhibits DNA methyltransferases[41], and has been shown to improve the induction reprogramming of MEFs induced by ectopic expression of Oct4 and Klf4 (but without Sox2)[42]. While not wishing to be bound by theory, it is considered that the method of the first aspect may benefit from the use of a DNA methylase inhibitor such as RG108 by maintaining induced stem cells in an undifferentiated state, as well as allowing for the replacement of transcription factors typically used in present induction processes in both mouse and human cell reprogramming. Other suitable DNA methyltransferase inhibitors may include those shown in Table 3. However, the person skilled in the art will appreciate that the list in Table 3 is not exhaustive and that other small molecule DNA methyltransferase inhibitors may be suitable for use in the present invention.

methyltransferase inhibitors employed, and the particular fibroblast cell(s). However, generally, the DNA methyltransferase inhibitor(s) will be provided for the culturing of the fibroblast cell(s) at a concentration in the range of 0.01 to 10 μM, preferably 0.1 to 2.0 μM, most preferably about 0.4 μM. Typically, the effective amount of the DNA methyltransferase inhibitor(s) will be provided in a culture medium suitable for the culture of fibroblast cells.

In some embodiments of the present invention, the method may comprise culturing the fibroblast cell(s) with a combination of two or more different DNA methyltransferase inhibitors.

The DNA methyltransferase inhibitor(s) may also be used in combination with one or more small molecule reprogramming factor(s) selected from:
 (i) HDAC inhibitors;
 (ii) MEK inhibitors;
 (iii) G9a HMTase inhibitors;
 (iv) GSK3 inhibitors;
 (v) Vitamin C; and
 (vi) ALK receptor inhibitors.

In embodiments, the DNA methyltransferase inhibitor(s) is in combination with a G9a HMTase inhibitor(s). In embodiments, the DNA methyltransferase inhibitor(s) is in combination with a MEK inhibitor(s). In another embodiment, the DNA methyltransferase-inhibitor(s) is in combination with a MEK inhibitor(s) and a G9a HMTase inhibitor(s). In a further embodiment, the method comprises culturing at least one fibroblast cell in the presence of an effective amount of RG108, wherein the method excludes the use of reprogramming factor(s) that are not small molecules. In a still further embodiment, the method comprises culturing at least one fibroblast cell in the presence of an effective amount of RG108 and BIX01294, wherein the method excludes the use of reprogramming factor(s) that are not small molecules. In yet still a further embodiment, the

TABLE 3

Small molecule DNA methylase inhibitors

| Chemical name | Synonyms | Molecular weight (g/mol) |
|---|---|---|
| 1H-β-D-ribofuranosyl-2-pyrimidinone | Zebularine | 228.2 |
| 4-amino-1-(2-deoxy-b-D-erythro-pentofuranosyl)-1,3,5-triazin-2(1H)-one (or 2'-Deoxy-5-azacytidine, 4-Amino-1-(2-deoxy-β-D-ribofuranosyl)-1,3,5-triazin-2(1H)-one) | decitabine, 5-aza-2'-deoxycytidine, dacogen | 228.2 |
| 2',3',5'-triacetyl-5-azacytidine (4-amino-1-(2,3,5-tri-O-acetyl-β-D-ribofuranosyl)-1,3,5-triazin-2(1H)-one (or 4-Amino-1-(β-D-ribofuranosyl)-1,3,5-triazin-2(1H)-one | 5-azacytidine, 5-azacitidine, Azacitidine, Vidaza, Mylosar, Ladakamycin | 244.2 |
| 1H-Indole-3-propanoic acid, α-(1,3-dihydro-1,3-dioxo-2H-isoindol-2-yl)-, (αS)- | N-phthalyl-L-tryptophan, RG108 | 334.3 |
| (−)-cis-3,3',4',5,5',7-Hexahydroxy-flavane-3-gallate; (−)-cis-2-(3,4,5-Trihydroxyphenyl)-3,4-dihydro-1(2H)-benzopyran-3,5,7-triol 3-gallate | (−)-Epigallocatechin gallate, EGCG | 458.4 |
| 1-Hydrazinophthalazine hydrochloride | Hydralazine hydrochloride | 196.6 |
| 4-Amino-N-(2-diethylaminoethyl)benzamide hydrochloride; 4-Aminobenzoic acid 2-diethylaminoethylamide | Procainamide hydrochloride | 271.8 |

The person skilled in the art will understand that an effective amount of a DNA methyltransferase inhibitor may vary depending upon, for example, the particular selected DNA methyltransferase inhibitor or combination of DNA methyltransferase inhibitors.

method comprises culturing at least one fibroblast cell in the presence of an effective amount of RG108, BIX01294 and PD325901, wherein the method excludes the use of reprogramming factor(s) that are not small molecules.

Suitable HDAC inhibitors for use in the present invention include butyrate/sodium butyrate, phenyl butyrate, AN-9, pivaloyloxymethyl butyrate, m-carboxycinnamic acid, bis-hydroxamic acid (CBHA), azeleic bishydroxamic acid (ABHA), oxamflatin, HDAC-42, SK-7041, DAC60, UHBAs, tubacin, trapoxin B, A-161906, R306465/JNJ16241199, suberic bishydroxamate (SBHA), 3-CI-UCHA ITF2357, PDX-101 pyroxamide, scriptaid, suberoylanilide hydroxamic acid/vorinostat/zolinza, trichostatin A (TSA), LBH-589 (panobinostat), NVP-LAQ824, apicidin depsipeptide/FK-228/romidepsin/FR901228 TPX-HA analogue (CHAP); CHAP1, CHAP31, CHAP50, CI-994 (N-acetyl dinaline), MS-275, PCK-101, MGCD0103, diallyl disulphide (DADS), disulphide sulphoraphane (SFN), sulphoraphene (SFN with a double bond), erucin phenylbutyl isothiocynanate, retinoids, SFN-N-acetylcysteine (SFN-NAC), SFN-cysteine (SFN-Cys), biotin, alpha-lipoic acid, vitamin E metabolites, trifluoromethyl ketones, alpha-ketoamides, splitomicin, LAQ824 SK-7068, panobinostat, and belinostat. However, preferably, the present invention utilises valproic acid (VPA; molecular weight=144.2 g/mol), which is a small cell-permeable molecule that has been shown to affect several pathways[37] and can improve the efficiency of cell reprogramming by some induction processes by at least 100-fold[38].

The person skilled in the art will understand that an effective amount of a HDAC inhibitor may vary depending upon, for example, the particular selected HDAC inhibitor or combination of HDAC inhibitors employed, and the particular fibroblast cell(s). However, generally, the HDAC inhibitor(s) will be provided for the culturing of the fibroblast cell(s) at a concentration in the range of 0.01 to 10 preferably 0.1 to 2.0 µM, most preferably about 1 µM. Typically, the effective amount of the HDAC inhibitor(s) will be provided in a culture medium suitable for the culture of fibroblast cells.

Suitable GSK3 inhibitors for use in the present invention include CHIR98014 (2,6-pyridinediamine, N6-[2-[[4-(2,4-dichlorophenyl)-5-(1H-imidazol-1-yl)-2-pyrimidinyl]amino]ethyl]-3-nitro-; molecular weight=486.31 g/mol), SB216763 (3-(2,4-dichlorophenyl)-4-(1-methyl-1H-indol-3-yl)-1H-pyrrole-2,5-dione; molecular weight=371.22 g/mol), TWS 119 (3-[6-(3-aminophenyl)-7H-pyrrolo[2,3-d]pyrimidin-4-yloxy]phenol; molecular weight=318.33 g/mol) and bisindolylmaleimide I (BIM). An example of one preferred GSK3 inhibitor is 6-{2-[4-(2,4-dichloro-phenyl)-5-(4-methyl-1H-imidazol-2-yl)-pyrimidin-2-ylamino]-ethylamino}-nicotinonitrile (also known as CHIR99021; molecular weight=465.3 g/mol). CHIR99021 has been found to enhance the survival of mouse embryonic stem (ES) cells at low cell density and can also suppress neural differentiation while promoting non-neural differentiation[43]. Moreover, it has previously been observed that CHIR99021 can enable reprogramming of mouse embryonic fibroblasts induced by Oct4 and Klf4. Other suitable GSK3 inhibitors may include those shown in Table 4. However, the person skilled in the art will appreciate that the list in Table 4 is not exhaustive and that other small molecule GSK3 inhibitors may be suitable for use in the present invention.

TABLE 4

Small molecule GSK3 inhibitors

| Chemical name | Synonyms | Molecular weight (g/mol) |
|---|---|---|
| 2,6-pyridinediamine, N6-[2-[[4-(2,4-dichlorophenyl)-5-(1H-imidazol-1-yl)-2-pyrimidinyl]amino]ethyl]-3-nitro- | CHIR98014 | 486.3 |
| 3-(2,4-dichlorophenyl)-4-(1-methyl-1H-indol-3-yl)-1H-pyrrole-2,5-dione | SB216763 | 371.2 |
| (3-[6-(3-aminophenyl)-7H-pyrrolo[2,3-d]pyrimidin-4-yloxy]phenol | TWS 119 | 318.3 |
| 6-{2-[4-(2,4-dichloro-phenyl)-5-(4-methyl-1H-imidazol-2-yl)-pyrimidin-2-ylamino]-ethylamino}-nicotinonitrile | CHIR99021, CT99021 | 465.3 |
| 3-(3-chloro-4-hydroxyphenylamino)-4-(2-nitrophenyl)-1H-pyrrole-2,5-dione | SB 415286 | 359.72 |
| 1,2,4-Thiadiazolidine-3,5-dione, 2-(1-naphthalenyl)-4-(phenylmethyl)- | Tideglusib NP031112, NP-12 | 334.39 |

The person skilled in the art will understand that an effective amount of a GSK3 inhibitor may vary depending upon, for example, the particular selected GSK3 inhibitor or combination of GSK3 inhibitors employed, and the particular fibroblast cell(s). However, generally, the GSK3 inhibitor(s) will be provided for the culturing of the fibroblast cell(s) at a concentration in the range of 0.01 to 10 µM, preferably 0.0.05 to 2.0 µM, most preferably about 0.3 µM. Typically, the effective amount of the GSK3 inhibitor(s) will be provided in a culture medium suitable for the culture of fibroblast cells.

Vitamin C (Vc; (R)-5-(S)-1,2-dihydroxyethyl)-3,4-dihydroxyfuran-2(5H)-one; also known as ascorbic acid; molecular weight=176.12 g/mol) has been found to enhance the generation of mouse and human iPS[44]. Vc is a cofactor in reactions driven by dioxygenases including collagen prolyl hydroxylases, hypoxia-inducible factor (HIF), prolyl hydroxylases and histone demethylases[45]. The person skilled in the art will understand that an effective amount of Vc may vary depending upon, for example, the particular combination of small molecule reprogramming factor(s) inhibitors employed, and the particular fibroblast cell(s). However, generally, Vc will be provided for the culturing of the fibroblast cell(s) at a concentration in the range of 1 to 100 µM, preferably 10 to 40 µM, most preferably about 25 µM. Typically, the effective amount of Vc will be provided in a culture medium suitable for the culture of fibroblast cells.

Suitable ALK receptor inhibitors include those that inhibit, predominantly, the TGF-β type I receptor ALK5, the Activin/Nodal receptor ALK4 and the nodal receptor ALK7. Examples of preferred inhibitors of this type are 3-(6-Methyl-2-pyridinyl)-N-phenyl-4-(4-quinolinyl)-1H-pyrazole-1-carbothioamide (also known as A83-01; molecular weight=421.52 g/mol) and 4-(5-benzol[1,3]dioxol-5-yl-4-pyridin-2-yl-1H-imidazol-2-yl)-benzamide hydrate, 4-[4-(1, 3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl)]-benzamide hydrate (also known as SB431542; molecular weight=384.4 g/mol). A83-01 strongly inhibits ALK4, 5 and 7 (IC50 values are 12, 45 and 7.5 nM respectively) and only weakly inhibits ALK1, 2, 3 and 6, and appears to inhibit TGF-β-induced EMT via the inhibition of Smad2 phosphorylation[46]. This small molecule has also been used to generate rat and human iPS cells towards a mouse ES cell like self-renewal state[47]. Other suitable ALK receptor inhibitors may include those shown in Table 5. However, the person skilled in the art will appreciate that the list in Table 5 is not exhaustive and that other small molecule ALK receptor inhibitors may be suitable for use in the present invention.

TABLE 5

Small molecule ALK receptor inhibitors

| Chemical name | Synonyms | Molecular weight (g/mol) |
| --- | --- | --- |
| 3-(6-Methyl-2-pyridinyl)-N-phenyl-4-(4-quinolinyl)-1H-pyrazole-1-carbothioamide | A83-01 | 421.5 |
| 4-(5-benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate | SB431542 | 384.4 |
| 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamin | TAE684; NVP-TAE684 | 614.2 |
| 2-(2-(1-(2-(dimethylamino)acetyl)-5-methoxyindolin-6-ylamino)-7H-pyrrolo[2,3-d]pyrimidin-4-ylamino)-6-fluoro-N-methylbenzamide | GSK1838705A | 532.57 |
| 9-ethyl-6,6-dimethyl-8-(4-morpholinopiperidin-1-yl)-11-oxo-6,11-dihydro-5H-benzo[b]carbazole-3-carbonitrile | CH5424802 | 482.62 |

The person skilled in the art will understand that an effective amount of an ALK receptor inhibitor(s) may vary depending upon, for example, the particular selected ALK receptor inhibitor(s) or combination of ALK receptor inhibitor(s) employed, and the particular fibroblast cell(s). However, generally, the ALK receptor inhibitor(s) will be provided for the culturing of the fibroblast cell(s) at a concentration in the range of 0.1 to 100 μM, preferably, 1 to 10 μM, most preferably about 2.5 μM. Typically, the effective amount of the ALK receptor inhibitor(s) will be provided in a culture medium suitable for the culture of fibroblast cells.

The culturing of the fibroblast cell(s) in the presence of small molecule reprogramming factor(s) will, in some embodiments, be conducted in a single induction culture cycle, comprising, for example, a first culture of the fibroblast cell(s) in a culture medium comprising the small molecule reprogramming factor(s) or combination thereof, followed by at least a second culture in the culture medium lacking the small molecule reprogramming factor(s) or combination thereof. In embodiments, the induction cycle comprises a first culture in the presence of small molecule reprogramming factor(s) as mentioned above, followed by second and third cultures in the culture medium lacking the small molecule reprogramming factor(s) or combination thereof.

In other embodiments, the culturing of the fibroblast cell(s) in the presence of small molecule reprogramming factor(s) will be conducted by multiple induction culture cycles, wherein one cycle may comprise, for example, a first culture of the fibroblast cell(s) in a culture medium comprising the small molecule reprogramming factor(s) or combination thereof, followed by at least a second culture in the culture medium lacking the small molecule reprogramming factor(s) or combination thereof. In some embodiments, the cycle will be repeated at least once. In some embodiments, the cycle may be repeated two, three, four, five or six times. In embodiments, the cycle will be repeated 5 times for a total of 6 cycles. However, the person skilled in the art will appreciate that the induction cycle could be repeated 10 times, or 20 times, or 30 times, etc, within the context of the present invention.

Optionally, following the induction culture cycle(s), the cells may be passaged in suspension in the culture medium lacking the small molecule reprogramming factor(s) or combination thereof, before a further culture stage in the same or different culture medium (again, lacking the small molecule reprogramming factor(s) or combination thereof). For example, the further culturing may occur in a media that is adapted to maintain neural stem cells.

Accordingly, in embodiments, the culturing of the at least one fibroblast cell comprises at least one induction cycle comprising the following steps:

(a) performing an at least one induction cycle comprising culturing for approximately one day the at least one fibroblast cell in the presence of an effective amount of at least one small molecule reprogramming factor(s) that induces the cell to de-differentiate into a multipotent stem cell, and then culturing for approximately two days the at least one cell in the absence of said effective amount of at least one small molecule reprogramming factor(s), and optionally (b) culturing the at least one cell of step (a) in media adapted to support multipotent stem cell growth for a suitable period.

In other embodiments, the culturing, of step (b) in media adapted to support multipotent stem cell growth is not optional. Accordingly, the culturing of the at least one fibroblast cell may comprise at least one induction cycle comprising the following steps:

(a) performing an at least one induction cycle comprising culturing for approximately one day the at least one fibroblast cell in the presence of an effective amount of at least one small molecule reprogramming factor(s) that induces the cell to de-differentiate into a multipotent stem cell, and then culturing for approximately two days the at least one cell in the absence of said effective amount of at least one small molecule reprogramming factor(s), and (b) culturing the at least one cell of step (a) in media adapted to support multipotent stem cell growth for a suitable period.

The culture medium used in the induction cycle(s) and the passaging in suspension may be any suitable medium for stem cells (eg embryonic stem cells) such as those that will be well known to the person skilled in the art. For the further culture stage, preferably a different culture medium will be used such as any of the suitable neural stem cell media well known to the person skilled in the art. In embodiments, the first culture of the fibroblast cell(s) in a culture medium comprising the small molecule reprogramming factor(s) or combination thereof is conducted using a culture medium composition (which may be in, for example, a gel or liquid form) comprising said small molecule reprogramming factor(s) or combination thereof optionally in combination with a nutrient source (ie providing a carbon and nitrogen source; eg yeast extract, or glucose/glycerol with ammonium salts or nitrates) and trace elements and vitamins as may be required for the culture of the cell(s).

In one preferred culture medium composition, the composition comprises BIX01294 (0.1 to 5 µM); optionally in combination with a nutrient source and trace elements and vitamins as may be required for the culture of the cell(s). In another preferred culture medium composition, the composition comprises PD325901 (0.1 to 5 µM); optionally in combination with a nutrient source and trace elements and vitamins as may be required for the culture of the cell(s). In another preferred culture medium composition, the composition comprises BIX01294 (0.1 to 5 µM) and PD325901 (0.1 to 5 µM); optionally in combination with a nutrient source and trace elements and vitamins as may be required for the culture of the cell(s). In another preferred culture medium composition, the composition comprises BIX01294 (0.1 to 5 µM) and RG108 (0.01 to 0.1 µM); optionally in combination with a nutrient source and trace elements and vitamins as may be required for the culture of the cell(s). In another preferred culture medium composition, the composition comprises PD325901 (0.1 to 5 µM) and RG108 (0.01 to 0.1 µM); optionally in combination with a nutrient source and trace elements and vitamins as may be required for the culture of the cell(s).

In another preferred culture medium composition, the composition comprises:
PD325901 0.1 to 5 µM;
RG108 0.01 to 0.1 µM; and
BIX01294 0.1 to 5 µM;
optionally in combination with a nutrient source and trace elements and vitamins as may be required for the culture of the cell(s).

In another preferred culture composition, the composition comprises:
PD325901 0.1 to 5 µM:
valproic acid 0.1 to 5 µM:
BIX01294 0.1 to 5 µM;
RG108 0.01 to 0.1 µM;
CHIR9901 1 to 5 µM;
vitamin C 10 to 50 µM; and
A83-01 1 to 5 µM;
optionally in combination with a nutrient source and trace elements and vitamins as may be required for the culture of the cell(s).

The media adapted to support multipotent stem cell growth may be any media known to the person skilled in the art that can readily meet the needs of neural stem cells, such as stem cell media or embryonic stem cell media (eg media containing DMEM supplemented with 15% PBS, 1% non-essential amino acids (Invitrogen), 1% L-glutamine (Invitrogen), 50 units ml$^{-1}$ penicillin, 50 µg ml$^{-1}$ streptomycin, 0.1 mM β-mercaptoethanol (Invitrogen), and 1000 Units ml$^{-1}$ leukaemia inhibitory factor (LIF), or suitable alternatives thereto as would be well known to the person skilled in the art.

The suitable period for which the cells obtained from the induction cycle(s) may be cultured in the media adapted to support multipotent stem cell growth may vary as would be understood by the person skilled in the art. For example, the cells may be cultured for 2 days, 6 days or 7 days. In some embodiments, the cells may be cultured in the media adapted to support multipotent stem cell growth media adapted to support multipotent stem cell growth for longer periods such as two weeks or longer. For example, cells may be cultured for four weeks or longer, for example, 8 weeks, to generate mature cell types such as neurons. The person skilled in the art will appreciate that other time periods may be suitable. The person skilled in the art will also understand that the cells may be passaged as required.

In embodiments, the media adapted to support multipotent stem cell growth is selected from the group consisting of a media to support neural stem cell growth, a media to support cardiac stem cell growth and a media to support haematopoetic stem cell growth. Suitable media will be known to the person skilled in the art. For example, media to support haematopoetic stem cells may include Sigma Aldric Stemline Hematopoietic Stem Cell Expansion Medium plus cytokines and antibiotics and glutamine. Media to support cardiac stem cells may include Sigma Aldric Stemline® Mesenchymal Stem Cell Expansion Medium plus L-glutamine fetal bovine serum and Millipore Mesenchymal Stem Cell Expansion Medium plus Accutase solution. The media adapted to support neural stem cell growth may be any media known to the person skilled in the art that can readily meet the needs of neural stem cells, such as neural stem cell (NSC) media (DMEM/F12 supplemented with B-27, HEPES buffer, epidermal growth factor (EGF), 10 ng ml$^{-1}$ basic fibroblast growth factor (bFGF); or Neurobasal Medium supplemented with bFGF, EGF), StemPro® NSC SFM, etc.

In some embodiments, prior to induction, the fibroblast cell(s) may be passaged two or more times in a culture medium (eg any suitable medium for embryonic stem cells such as those that will be well known to the person skilled in the art) to eliminate any neural crest stem cells. In other embodiments, any neural crest cells may be removed by other means, for example, using FACS sorting with a neural crest stem cell marker such as p75-NTR.

In some embodiments, the initial induction cycle may be preceded by a pre-induction culture step. In embodiments, the pre-induction culture step may comprise culturing the at least one fibroblast cell with feeder cells in a suitable culture medium. The concept of culturing cells with feeder cells is well known in the art. The feeder cell can be any suitable cell known to the person skilled in the art, for example, embryonic fibroblasts. In embodiments, the pre-induction culture step may comprise culturing the at least one fibroblast cell on a substrate (eg a tissue culture dish well known to the person skilled in the art) coated with poly-D-lysine or laminin in a suitable culture medium. The person skilled in the art will appreciate that other substrate coatings may be suitable for the pre-induction culture step.

In embodiments, the multipotent stem cell produced by the method of the first aspect is an induced multipotent stem cell. In embodiments, the multipotent stem cell is a cardiac stem cell. In other embodiments, the multipotent stem cell is a haematopoetic stem cell. In embodiments, the multipotent stem cell is a neural stem cell. In embodiments, the multipotent stem cell is an induced neural stem cell. Neural stem cells induced by the method of the first aspect may be referred to as small molecule induced neural stem cells (SMINS) herein. In embodiments, the multipotent stem cell is a human cell.

The product of the method of the first aspect of the invention will be a multipotent stem cell which may, for example, be used for therapeutic, diagnostic and/or research (including drug development and screening, or disease modelling) purposes.

In at least some instances, multipotent stem cells produced in accordance with the method of the first aspect will be novel, as evidenced by novel patterns of gene expression. It is to be understood that the present invention extends to those novel multipotent stem cells, particularly where provided in a substantially isolated form.

In embodiments of the first aspect, the method produces a multipotent stem cell which expresses the neural stem cell markers ALP, Sox2 and SSEA1. Preferably, the multipotent stem cell also expresses the neural stem cell marker genes Sox2, GFAP, Pax6 and Olig2, but does not express the pluripotent genes Oct4 and Nanog. Alternatively, the multipotent stem cell also expresses the neural stem cell marker genes Sox2, GFAP and Pax6 and, like native neural stem cells, the Gli2 gene (which encodes a transcription factor thought to be involved in embryogenesis), but does not express the pluripotent genes Oct4 and Nanog. In another embodiment, the multipotent stem cell expresses ALP, Sox2 and SSEA1 and the neural stem cell marker genes Sox2, GFAP, Nestin and Olig2, but does not express the pluripotent genes Oct4 and Nanog In an embodiment, the multipotent stem cell expresses neural stem cell markers selected from the group consisting of ALP, Sox2, SSEA1, GFAP, Nestin and Olig2.

The cells described in the preceding paragraph may be regarded as neural stem cells. Accordingly, they are referred to herein as small molecule-induced neural stem (SMINS) cells. Preferred SMINS exhibit up-regulated expression of at least the following genes relative to native neural stem cells: Notch2, Shh and Fgf2. Since neural stem (NS) cells are widely recognised as having a strong potential to repair neurodegenerative diseases and enhance the regeneration of damaged nervous system[22,23], the SMINS of the present invention are likely to be of considerable value in the development of new therapeutic methods. The SMINS of the present invention may be useful in treating diseases such as Parkinson's disease, Huntington's disease, multiple sclerosis, or damage to nerve tissue such as a spinal injury etc.

The SMINS produced in accordance with the method of the first aspect may comprise a neurosphere (ie a nonadherent cluster of cells including neural stem cells). Thus, in some embodiments, the method may further comprise isolating one or more individual SMINS cells from a neurosphere. This may be achieved by any of the methods well known to the person skilled in the art such as the simple method of gently pipetting the neurospheres "up and down" until separated into single cells.

The present applicant has found that the SMINS may differentiate into, at least, astrocytes, neurons and oligodendrocytes.

Accordingly, in a second aspect, the present invention provides a method for producing a differentiated cell, said method comprising culturing a multipotent stem cell produced by the method of the first aspect under conditions suitable for differentiation of said multipotent stem cell into a differentiated cell selected from the group consisting of an astrocyte, a neuron and an oligodendrocyte For astrocyte differentiation, the cells may, for example, be cultured in a neural stem cell medium plus 1% foetal bovine serum (FBS) for 7 days.

For neuron differentiation, the cells may, for example, be cultured in DMEM/F12 medium supplemented with B27 plus 10 ng/ml bovine fibroblast growth factor (bFGF) for 5 days and then DMEM/F12: Neurobasal media (1:1) supplemented with B27, 0.5×N2 for 2 days.

For oligodendrocyte differentiation, the cells may, for example, be cultured in a neural stem cell medium (without epidermal growth factor (EGF)) plus 10 ng/ml platelet-derived growth factor (PDGF) for 4 days, and then 3,3,5-tri-iodothyronine (T3) and ascorbic acid for 2 days.

However, the person skilled in the art will be aware that there are other suitable methods for differentiating neural stem cells, such as those disclosed in References 50-54. The entire content of each of these publications is hereby incorporated by reference. Such methods may be used to differentiate cells in accordance with the second aspect of the present invention.

In a third aspect, the present invention provides a neural stem cell in a substantially isolated form, said cell characterised in that it expresses the neural stem cell markers ALP, Sox2 and SSEA1 and the neural stem cell marker genes Sox2, GFAP, Pax6 and Olig2, but does not express the pluripotent genes Oct4 and Nanog. In embodiments, the neural stem cell is produced using the method of the first aspect of the invention.

In a fourth aspect, the present invention may provide a neural stem cell in a substantially isolated form, said cell characterised in that it expresses the neural stem cell markers ALP, Sox2 and SSEA1 and the neural stem cell marker genes Sox2, GFAP, Nestin and Olig2, but does not express the pluripotent genes Oct4 and Nanog. In embodiments, the neural stem cell is produced using the method of the first aspect of the invention.

In a fifth aspect, the present invention provides a differentiated cell in accordance with the present invention. In embodiments, the differentiated cell may be differentiated from the cell of the third or fourth aspects, or alternatively, from a cell produced by the method of the first aspect, or in yet another alternative, be a cell produced by the method of the second aspect.

The SMINS, or cells differentiated from SMINS, will be useful in assays for the development and screening of drug candidates. For example, the SMINS may be directed to differentiate into the cell type(s) that are important for screening a particular drug candidate. These cells may be more likely to mimic the response of human tissue to the drug being tested than animal models do. In turn, this may make drug testing safer, cheaper and more ethically acceptable to those who oppose the use of animals in pharmaceutical testing. Importantly, the use of SMINS, or cells differentiated from SMINS, may increase the relevance of disease modelling. For example, studying SMINS induced from human fibroblasts isolated from a patient with a neurological condition may provide a more convenient and more relevant disease model compared to studying a non-human animal model of the disease, or alternatively, obtaining diseased neural stem cells from a human subject with certain neurological conditions, in situations where such cells can only be derived from brain tissue, as it is generally necessary to obtain such cells from cadaveric subject, Accordingly, in a sixth aspect, the present invention provides an assay for determining the effect of a drug candidate on a cell, said assay comprising culturing a differentiated cell produced by the method of the second aspect in the presence of said drug candidate.

The drug candidate may be a compound or other agent under investigation as a potential new drug for a therapeutic treatment. The drug candidate may also be a compound or other agent selected from known drugs for a therapeutic treatment, that are under investigation for suitability and/or efficacy for use in a particular individual (ie in a "personalised medicine" approach), in which case, the differentiated cell is preferably produced from an autologous multipotent stem cell.

In a seventh aspect, the present invention provides a kit for use in the method of the first aspect, said kit comprising a G9a HMTase inhibitor(s) and, optionally, one or more small molecule reprogramming factor (s) selected from the group consisting of a DNA methyltransferase inhibitor(s), a MEK inhibitor(s), a HDAC inhibitor(s), a GSK3 inhibitor(s), Vitamin C; and a ALK receptor inhibitor(s); together with a suitable culture medium.

In an eighth aspect, the present invention provides a kit for use in the method of the first aspect, said kit comprising a MEK inhibitor(s) and, optionally, one or more small molecule reprogramming factor(s) selected from the group consisting of a DNA methyltransferase inhibitor(s), a G9a HMTase inhibitor(s), a HDAC inhibitor(s), a GSK3 inhibitor(s), Vitamin C; and a ALK receptor inhibitor(s); together with a suitable culture medium.

In a ninth aspect, the present invention provides a kit for use in the second aspect, said kit comprising a small molecule reprogramming factor(s) required for the differentiation of the cells together with a suitable culture medium and, optionally, instructions for said use.

In a tenth aspect, the present invention provides a kit for use in the assay of the sixth aspect, said kit comprising a suitable culture medium together with reagents for assessing an effect of a drug candidate upon the cells and, optionally, instructions for said use.

Accordingly, the present invention may provide a kit for use in the method of the first aspect (eg a kit comprising, for example, the small molecule reprogramming factor(s) of combinations thereof mentioned above together with a suitable culture medium and, optionally, instructions for use), a kit for use in the method of the second aspect (eg a kit comprising an agent required for the differentiation of the cells together with a suitable culture medium and, optionally, instructions for use), and a kit for use in the assay of the sixth aspect (eg a kit comprising a suitable culture medium together with reagents (such as antibodies against cell markers) for assessing an effect of a drug candidate upon the cells and, optionally, instructions for use). Moreover, the present invention also extends to formulations of, and kits for formulating, cells produced by the method of the first or second aspects, for therapeutic purposes. In embodiments, said kit comprises a G9a HMTase inhibitor(s) and, optionally, one or more small molecule reprogramming factor (s) selected from the group consisting of a DNA methyltransferase inhibitor(s), a MEK inhibitor(s), a HDAC inhibitor(s), a GSK3 inhibitor(s), Vitamin C; and a ALK receptor inhibitor(s); together with a suitable culture medium. In other embodiments, said kit comprises a MEK inhibitor(s) and, optionally, one or more small molecule reprogramming factor (s) selected from the group consisting of a DNA methyltransferase inhibitor(s), a G9a HMTase inhibitor(s), a HDAC inhibitor(s), a GSK3 inhibitor(s), Vitamin C; and a ALK receptor inhibitor(s); together with a suitable culture medium. In embodiments, said kit comprises a small molecule reprogramming factor(s) required for the differentiation of the cells together with a suitable culture medium and, optionally, instructions for said use. In embodiments, said kit comprises a suitable culture medium together with reagents (for example, antibodies or other binding partners) for assessing an effect of a drug candidate upon the cells and, optionally, instructions for said use.

In an eleventh aspect, the present invention provides a method of treating a subject in need of same with a therapeutically effective amount of cells obtained from the method of the first or second aspects. In embodiments, the present invention provides a method of treating a subject in need of same with a therapeutically effective amount of cells of the third, fourth of fifth aspects. Accordingly, the cells to be used in the method of treating may be SMINS or cells differentiated therefrom, for example, astrocytes, neurons or oligodendrocytes. In an embodiment, the method of treating may be a therapy for treating diseased or damaged tissue. For example, the SMINS of the present invention or cells differentiated therefrom may be used to treat neurodegenerative diseases such as Parkinson's disease, Huntington's disease, multiple sclerosis, etc, or may be used to regenerate nerve tissue damaged by neural injury such as spinal injury. In some embodiments, the present invention provides a use of a therapeutically effective amount of cells obtained from the first or second aspects in treating a subject in need of same. In some embodiments, the present invention provides a use of the cells obtained from the method of the first or second aspects in the manufacture of a medicament for the treatment of a subject in need of same.

Methods for treating the subject are well known to those skilled in the art. The mode of administration of the cells may be by way of systemic transfusion, implantation or, for damaged neural tissue, injection directly at the damaged site. The term "therapeutically effective amount" is to be understood as referring to an amount of the cells (ie a cell number) that will, at least, arrest the disease or injury being treated. Such an amount may vary considerably depending upon a range of factors such as the mode of administration, the age and/or body weight of the subject, and the severity of the disease or injury to be treated.

In a twelfth aspect, the present invention provides a method of modelling disease or tissue damage using cells obtained from the method of the first or second aspects. In embodiments, the present invention provides a method of modelling disease using cells of the third, fourth of fifth aspects. Accordingly, the cells to be used in the method of modelling disease may be SMINS or cells differentiated therefrom, for example, astrocytes, neurons or oligodendrocytes. In embodiments, the disease may be a neurodegenerative disease such as Parkinson's disease, Huntington's disease, multiple sclerosis, etc. In embodiments, the tissue damage may be nerve tissue damage, including neural injury such as spinal injury.

In some embodiments, cells obtained from the method of the first, second, third, fourth of fifth aspects replace the use of cadaveric cells, cell lines or animal models for disease modeling and other research applications. In some embodiments, the cells used in disease modelling are autologous cells and derived from a diseased patient to assess and diagnose disease and identify therapeutic options for said patient. In other embodiments, the cells used in modelling are heterologous cells. In some embodiments, the cells are used to identify or direct treatment decisions.

The present invention is hereinafter further described by way of the following, non-limiting examples.

EXAMPLES

Example 1 Induction of Neural Stem Cells from Mouse Fibroblasts Using Different Combinations of Small Molecules Methods and Materials Cell Culture Mouse embryonic fibroblasts (MEF) and mouse adult tail-tip fibroblasts (TTF) were isolated from C57/BL6 mice as described previously[2]. Both cell types (ie MEF and TTF) were cultured in MEF medium (Dulbecco's Modified Eagle Medium (DMEM; Invitrogen Corporation, Carlsbad, Calif., United States of America) containing 10% Fetal Bovine Serum (FBS; Thermo Fisher Scientific, Waltham, Mass., United. States of America), 50 units/ml penicillin and 50 µg/ml streptomycin (Invitrogen)). Native NS cells were cultured from mouse brain at E12-E14 as positive controls in neural stem (NS) cell media.

Induction of SMINS Cells 35 mm tissue culture dishes were coated with feeder cells (fibroblasts cultured from mouse embryo and seeded at $1.4 \times 10^5$ cells per 35 mm tissue culture dish) before induction. The MEF (passage 3) or TTF were seeded at $1.4 \times 10^5$ per 35 mm feeder cell-coated dish. The cells were induced in 6 cycles. On the first day, the cells were induced in stem cell culture medium (SCM; DMEM supplemented with 15% FBS, 1% non-essential amino acids (Invitrogen), 1% L-glutamine (Invitrogen), 50 units $ml^{-1}$ penicillin, 50 µg $ml^{-1}$ streptomycin, 0.1 mM β-mercaptoethanol (Invitrogen), and 1000 Units $ml^{-1}$ leukaemia inhibitory factor (LIF) (Millipore Corporation, Billerica, Mass., United States of America); this media is also referred to as ES media herein) containing various small molecules (valproic acid, 1 µM (Stemgent Inc, San Diego, Calif., United States of America); BIX01294, 1 µM (Stemgent); RG108, 0.04 µM (Stemgent); PD325901, 1 (Stemgent); CHIR9901, 3 µM (Stemgent); vitamin C, 25 µM (Sigma-Aldrich); A83-01, 2.5 µM (Stemgent)) as detailed below. The cells were then cultured in SCM in the absence of the small molecules for the next two days. Then, the cycle was repeated 5 times. Next, the cells were passaged and suspended in a drop of 20 µM containing at least 50 cells for two days. Finally, the cells were cultured in the neural stem (NS) cell medium (DMEM/F12 (Invitrogen) supplemented with B-27 (1:50; Gibco Inc, Billings, Mont., United States of America), 50 units $ml^{-1}$ penicillin, 50 µg $ml^{-1}$ streptomycin, 8 mM HEPES buffer, 20 ng $ml^{-1}$ epidermal growth factor (EGF), 10 ng $ml^{-1}$ basic fibroblast growth factor (bFGF) for two weeks.

Reverse Transcription-Polymerase Chain Reaction (RT-PCR) and Real Time (RT) Profiler PCR Array Total RNA was extracted by RNeasy Mini Kit (Qiagen NV, Venlo, The Netherlands) with on-column DNA digestion in accordance with the manufacturer's instructions. Total RNA (500 ng) was converted to cDNA by Superscript III cellsDirect cDNA Synthesis System (Invitrogen) in accordance with the manufacturer's instructions. PCR was performed using the primers shown in Table 6 using a standard protocol.

TABLE 6

| Gene | Forward | Reverse |
|---|---|---|
| Pax6 | TTTAACCAAGGGCGGTGAGCAG [SEQ ID NO: 1] | TCTCGGATTTCCCAAGCAA AGATG [SEQ ID NO: 2] |
| Olig2 | TCATCTTCCTCCAGCACCTC [SEQ ID NO: 3] | CCGTAGATCTCGCTCACCA G [SEQ ID NO: 4] |
| Gli2 | GCCTGAGCCTTTGCCTTCAC [SEQ ID NO: 5] | ATGTTGCTGATGCCCGCAG [SEQ ID NO: 6] |
| Sox10 | GCTGCTGCTATTCAGGCTCACTAC [SEQ ID NO: 7] | GTTGGACATTACCTCGTGG CTG [SEQ ID NO: 8] |
| Emx2 | CCGGGCACCGCTTACAGGACA [SEQ ID NO: 9] | TCGATAAGCGGAATACCCG CCAA [SEQ ID NO: 10] |
| GFAP | ACCATTCCTGTACAGACTTTCTCC [SEQ ID NO: 11] | AGTCTTTACCACGATGTTC CTCTT [SEQ ID NO: 12] |
| c-Myc | TCAAGCAGACGAGCACAAGC [SEQ ID NO: 13] | TACAGTCCCAAAGCCCCAG C [SEQ ID NO: 14] |
| Klf4 | GGCGAGAAACCTTACCACTGT [SEQ ID NO: 15] | TACTGAACTCTCTCTCCTG GCA [SEQ ID NO: 16] |
| Oct4 | CCAACGAGAAGAGTATGAGGC [SEQ ID NO: 17] | CAAAATGATGAGTGACAGA CAGG [SEQ ID NO: 18] |
| Sox2 | TCTGTGGTCAAGTCCGAGGC [SEQ ID NO: 19] | TTCTCCAGTTCGCAGTCCA G [SEQ ID NO: 20] |
| Nanog | CCTCCAGCAGATGCAAGAA [SEQ ID NO: 21] | GCTTGCACTTCATCCTTTG G [SEQ ID NO: 22] |
| Gapdh | ACCACAGTCCATGCCATCAC [SEQ ID NO: 23] | TCCACCACCCTGTTGCTGT A [SEQ ID NO: 24] |

For RT profiler PCR array, the total RNA removed total genome DNA was analysed using Mouse Neurogenesis and Neural Stem Cells PCR Array (Qiagen) in accordance with the manufacturer's instructions.

Alkaline Phosphatase and Immunofluorescence Staining

ES culture medium (also referred to as SCM herein) was added to NS and SMINS cells overnight. Alkaline phosphatase staining was carried out according to the manufacturer's protocol (Hoffman-La Roche, Basel, Switzerland). For the immunofluorescence staining, cells were washed with phosphate buffered saline (PBS) and then fixed with 4% paraformaldehyde for 10 min. After washing twice with PBS, the cells were permeabilised with 0.1% Triton X-100 for 20 min. Cells were then washed twice and blocked in blocking buffer (a solution of PBS containing 1% FBS and 4% bovine serum albumin (BSA)) for 1 hour. Primary antibodies were diluted in blocking buffer and applied for 1 hour at room temperature or overnight at 4° C. Primary antibodies were used at the following dilution: Sox2 (1:200, mouse; Millipore), SSEA-1 (1:200, mouse; Santa Cruz Biotechnology Inc, Santa Cruz, Calif., United States of America), GFAP (1:1000, rabbit; Dako Denmark A/S, Glostrup, Denmark), nestin (1:200, rabbit; DSHB), MAP2 (1:5000, rabbit, Osenses Pty Ltd, Keswick, SA, Australia), βIII-tubulin (1:5000, mouse; Sigma-Aldrich) and P25 (1:1000, rabbit; Gai, W-P, Flinders University of South Australia). Cells were washed three times with PBS and then applied with secondary fluorescent antibodies (1:1000, Cy3 or Alexa-488) and 10 µg/ml 4',6-diamidino-2-phenylindole (DAPI, a nuclear fluorescent stain, Invitrogen) for 1 hour at room temperature.

In Vitro Differentiation of SMINS Cells

SMINS cells were seeded at $0.5 \times 10^4$ per well on a PDL/laminin coated 4-well plate. For spontaneous differentiation, cells were cultured in NSC culture medium without EGF or bFGF for about 3 weeks. For astrocyte differentiation, cells were cultured in neural stem cell medium plus 1% FBS for 7 days. For neural differentiation, cells were exposed to DMEM/F12 medium supplemented with B27 plus 10 ng/ml bFGF for 5 days and then switched to DMEM/F12: Neurobasal media (1:1) supplemented with B27, 0.5×N2 for 2 days. For oligodendrocyte differentiation, cells were treated with neural stem cell medium (without EGF) plus 10 ng/ml platelet-derived growth factor (PDGF) for 4 days, and then 3,3,5-tri-iodothyronine (T3, 30 ng/ml, Sigma-Aldrich) and ascorbic acid (20 ng/ml, Sigma-Aldrich) were added into the medium for 2 days. For differentiation into mature neurons, single SMINS cells were cultured in neurobasal medium (Invitrogen) containing B27 (2%) (Invitrogen) and Gluta MAX (2 mM) (Invitrogen) for about four weeks. The dish was divided 1:3 when the cells achieved confluence. Expression of mature neuron markers Synatophysin (Green) and Vamp2 (Green) was examined by immunofluorescence, with DAPI used for nuclei counterstaining (blue).

Electrophysiology Methods

Patch clamping in the whole cell configuration was performed on differentiated cells using a HEKA EPCIO patch clamp amplifier and PatchMaster software (HEKA Elektronik, Lambrecht/Pfalz, Germany). Patch pipettes were pulled from borosilicate glass and fire polished, with resistance of 3-5 MΩ. Internal solution contained (mM): NaCl, 10; KCl, 145; HEPES, 10; MgCl2, 1; EGTA, 1; adjusted to pH 7.3. External solution contained (mM): NaCl, 135; KCl, 2.8; HEPES, 10; MgCl$_2$, 1; CaCl$_2$, 2; Glucose, 10; adjusted to pH 7.4 with NaOH. Measurement of Na+ and K+ currents was performed in voltage-clamp mode, utilising a protocol with voltage steps of −70 to +70 mV (10 mV increments), for 20 ms or 100 ms, from a holding potential of −80 mV. Series resistance was compensated at least 70%. Action potentials were recorded in current-clamp mode, with injection of 20-50 pA of current. Voltages shown are not adjusted for liquid junction potential.

Results and Discussion

Experimentation was undertaken to determine whether only small molecules, in place of potentially hazardous reprogramming factors such as transfection vectors or transcription factors, could be used to induce mouse fibroblasts into neural stem cells. To this end, a number of candidate small molecules were selected to attempt to reprogram fibroblasts into neural stem cells. It was found that the combination of the following small molecules:

PD325901 1 µM
valproic acid 1 µM
BIX01294 1 µM
RG108 0.04 µM
CHIR9901 3 µM
vitamin C 25 µM
A83-01 2.5 µM;

is able to induce mouse embryonic fibroblasts (MEF) and adult tail-tip fibroblasts (TTF) into NS cells (ie small molecule induced neural stem cells, termed SMINS-MEF-7 and SMINS-TTF-7, respectively, herein).

Figure 1B:
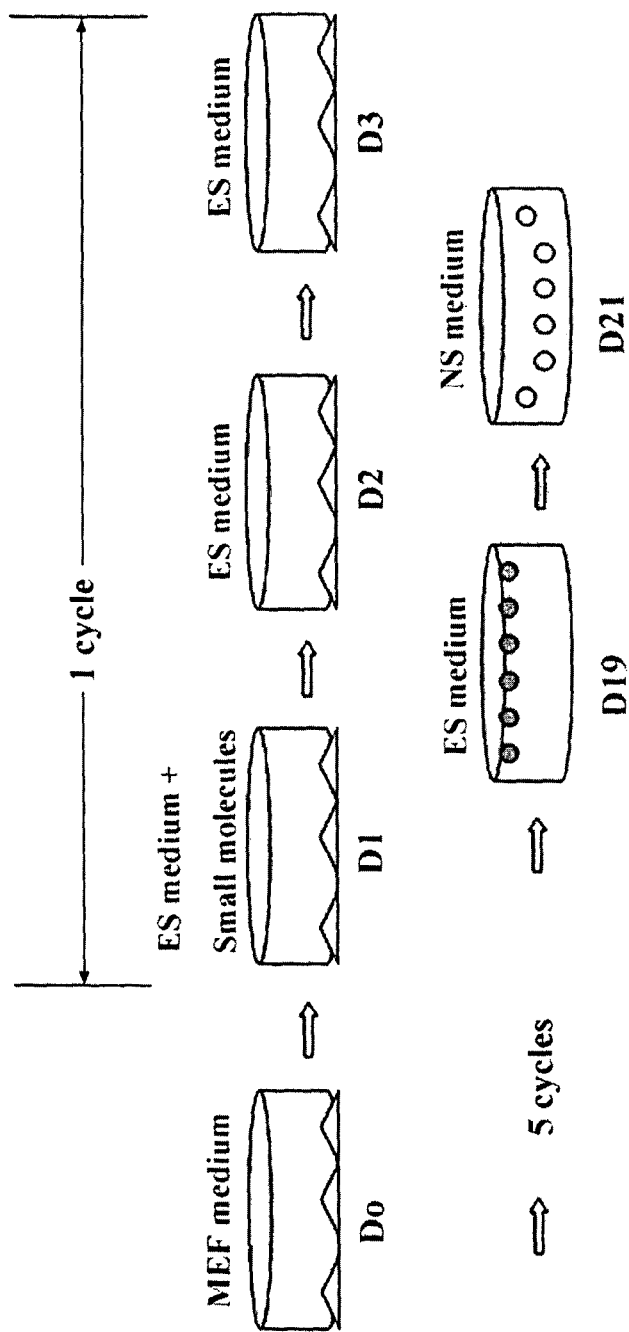

It was found that the isolated MEF (ie prior to induction) were negative to the neural stem cell markers alkaline phosphatase (ALP) (FIG. 1a), Sox2 and SSEA-1 (immunofluorescence results not shown) after two passages. In order to eliminate neural crest stem cells from mouse skin[24], only passage 2 MEF cells were used for induction. Also, in view of findings that over-expression of transcription factors may be detrimental to the self-renewal of pluripotent cells[2], a 6-cycle protocol (FIG. 1b) for the induction was designed, wherein fibroblasts were cultured alternatively in small molecule-containing stem cell culture medium (SMSCM) for 1 day and in stem cell culture medium (SCM) without small molecules for 2 days as cycle 1, and then the cycle was repeated an additional 5 times. After the 6th cycle, the cells were cultured in suspension for 2 days and then in NS cell culture medium for 2 weeks.

The resulting SMINS (SMINS-MEF-7) cells were able to be stably and homogenously expanded over 10 passages without a significant reduction in the self-renewal capacity. They were also found to be morphologically indistinguishable from native neural stem cells (FIG. 1a), and expressed the neural stem cell markers ALP (FIG. 1a), Sox2 and SSEA1 (as determined by immunofluorescence; results not shown). The induction efficiency of SMINS cells from fibroblasts was very high and consistent; with up to 2% of the fibroblasts being induced to SMINS cells.

Figure 2A:
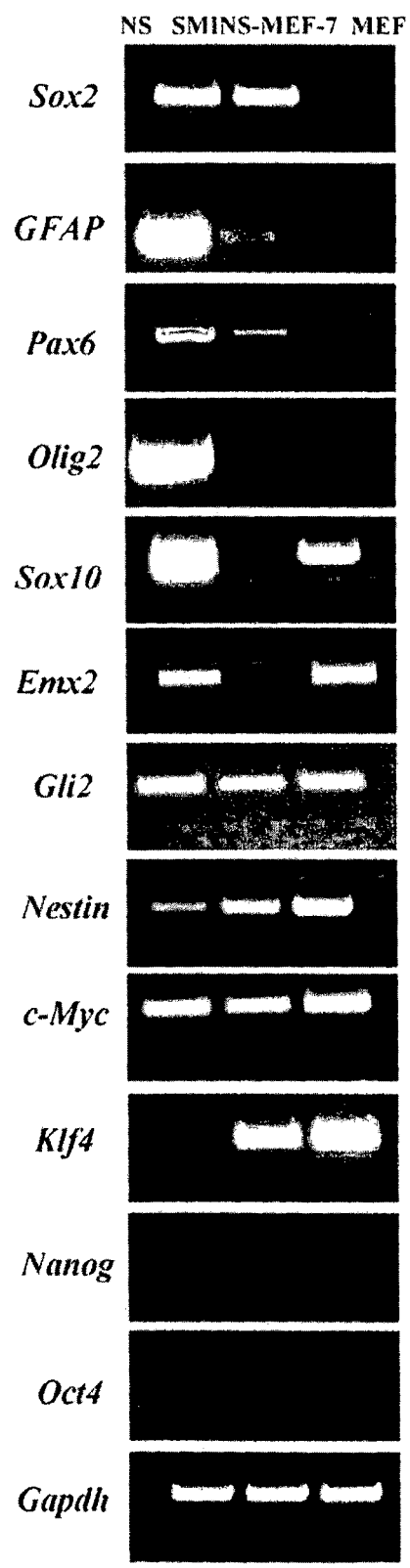
FIG. 2 provides images showing (a) RT-PCR analysis of expression of typical neural stem cell genes from NS. SMINS-MEF-7 and MEF; and (b and c) quantitative analysis of 84 neural stem cell genes by RT profiler PCR arrays. The black line depicts the regression of absolute correlation between two different cell types; the dashed lines depict the scoring border lines with a two-fold change in standard deviation from the absolute correlation line, NS=native neural stem cells.
Figure 2B:
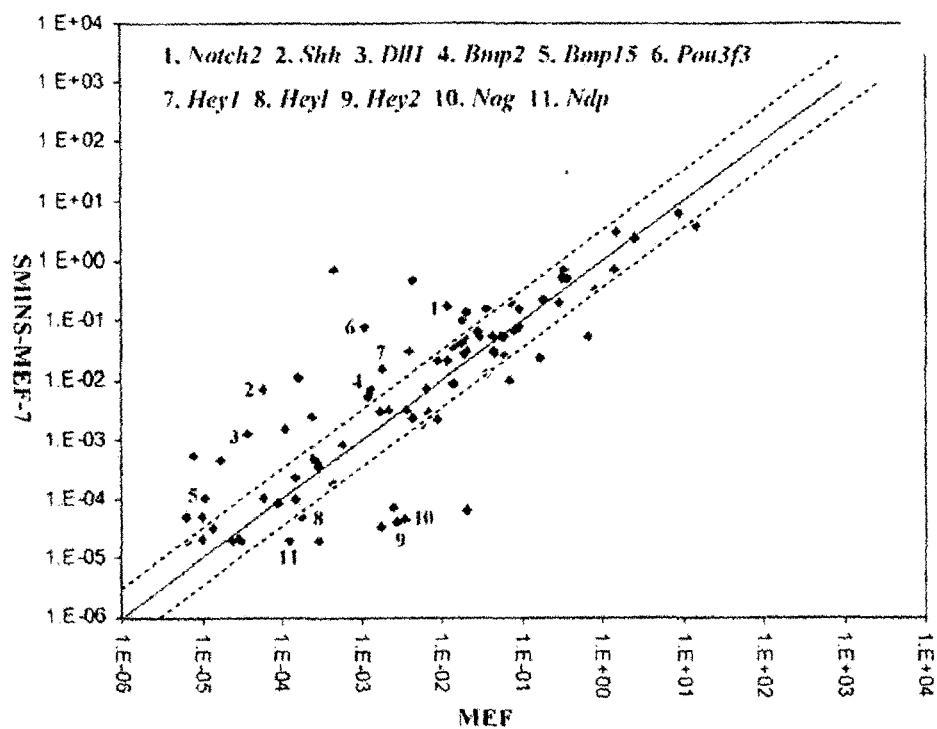
Figure 2C:
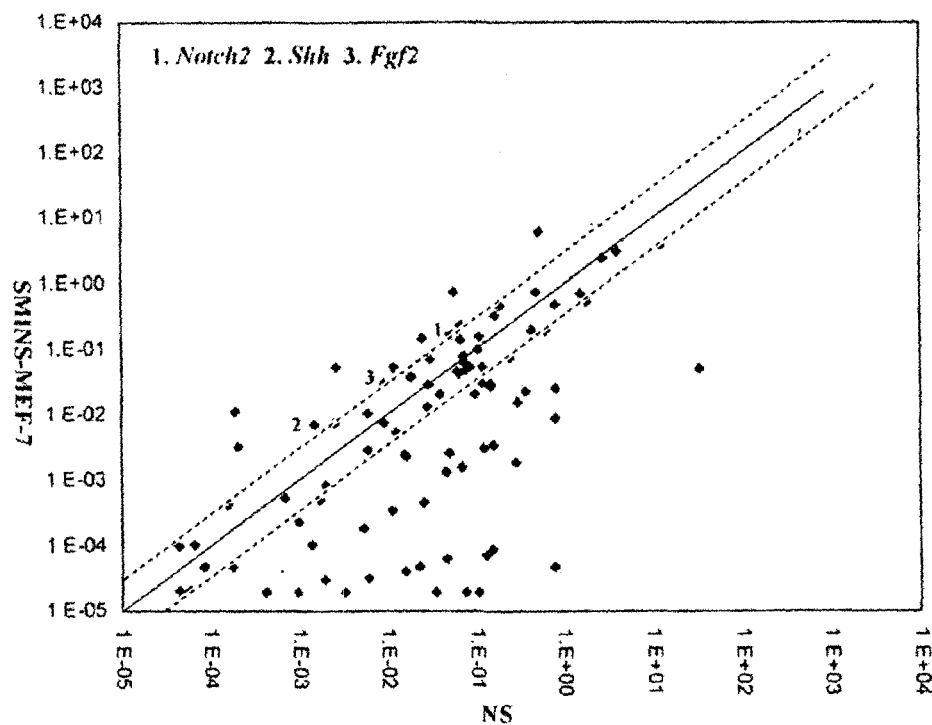

The expression of neural stem cell marker genes was also investigated by reverse transcription PCR (RT-PCR). Compared to fibroblasts, SMINS-MEF-7 cells expressed neural stem cell marker genes including Sox2, GFAP, Pax6 and Olig2 (FIG. 2a). Just like neural stem cells, SMINS-MEF-7 cells did not express the pluripotent genes Oct4 and Nanog (FIG. 2a). In order to further assess the expression profiles of genes relevant to NS cells, an analysis of another 84 genes related to mouse neurogenesis and NS cells was conducted utilising RT profiler PCR arrays, Compared with MEF, 23 genes were found to be up-regulated 3- to 1543-fold and 13 genes were down-regulated at least 3-fold in SMINS-MEF-7 cells (FIGS. 2b and c, and Table 7). Notch[25-27], Wnt[28,29], BMP[30,31] and Shh signalling pathways are known to regulate NS cell properties. Among the up-regulated genes, Dll1, Notch2, Hey1 and Pou3f3 are involved in the Notch signalling pathway, Shh in the Shh signalling pathway and Bmp2 and Bmp15 in the BMP signalling pathway. Among the down-regulated genes, Hey2 and Hey1 are involved in the Notch signalling pathway, Nog in the BMP signalling pathway and Ndp in the Wnt signalling pathway. Ten genes including Notch2, Shh and Fgf2 were up-regulated in SMINS-MEF-7 in comparison with native NS cells (FIGS. 2b and c, and Table 8). A number of genes related to neuronal differentiation, axonal guidance and glial differentiation, such as Cdk5rap2, Pou4fl, S100b, Sema4d, Tnr and Vegfa, appeared to be up-regulated in SMINS-MEF-7 cells, indicating that these cells express even higher levels of neural-related genes than native NS cells (Table 8).

TABLE 7

| Up-regulated Genes | Up-regulated fold | Down-regulated Genes | Down-regulated fold |
|---|---|---|---|
| Apbb1 | 7.8 | Fgf13 | 329.19 |
| Bmp15 | 9.29 | Hey2 | 67.38 |
| Bmp2 | 5.62 | Heyl | 3.58 |
| Cdk5rap2 | 4.40 | Inhba | 12.75 |
| Cxcl1 | 67.46 | Ndn | 7.14 |
| Dll1 | 34.20 | Nog | 75.12 |
| Drd2 | 3.01 | Nrcam | 35.50 |
| Hdac4 | 5.30 | Pard6b | 3.80 |
| Hey1 | 8.66 | Pax3 | 53.13 |
| Il3 | 7.50 | Arnt2 | 3.13 |
| Neurod1 | 3.01 | Ascl1 | 15.35 |
| Notch2 | 14.11 | Bdnf | 6.94 |
| Ntn1 | 107.11 | Ndp | 6.44 |
| Pax6 | 13.88 | | |
| Pou3f3 | 68.02 | | |
| Pou4fl | 65.98 | | |
| Robo1 | 6.79 | | |

TABLE 7-continued

| Up-regulated Genes | Up-regulated fold | Down-regulated Genes | Down-regulated fold |
|---|---|---|---|
| S100a6 | 1543.93 | | |
| Sema4d | 10.06 | | |
| Shh | 123.47 | | |
| Sox3 | 26.94 | | |
| Tnr | 4.74 | | |
| Vegfa | 4.19 | | |

TABLE 8

| Up-regulated Genes | Up-regulated fold |
|---|---|
| Cxcl1 | 57.20 |
| Fgf2 | 3.43 |
| Gdnf | 15.62 |
| Inhba | 19.22 |
| Notch2 | 3.23 |
| Nrp1 | 13.23 |
| S100a6 | 11.58 |
| Shh | 4.90 |
| Slit2 | 4.52 |
| Vegfa | 6.51 |

To confirm the multipotency of the SMINS cells, in vitro differentiation assays were performed and assessed by immunofluorescence (results not show). SMINS-MEF-7 cells were found to be able to spontaneously differentiate into astrocytes (GFAP+), neurons (MAP2+) or oligodendrocytes (P25+). In directed differentiation assays, it was demonstrated that SMINS-MEF-7 cells could be induced to preferentially differentiate into either astrocytes (GFAP+), neurons (MAP2+ and βIII-tubulin+) or oligodendrocytes (P25+). These results indicate that, like native NS cells, SMINS cells are multipotent in vitro.

Next, experiments were conducted to determine which small molecules are essential for the generation of SMINS-MEF cells from fibroblasts by withdrawal of individual small molecules from the combination (Table 4). It was found that the small molecules BIX01294, RG108 and PD325901 were required for the induction.

Figure 3A:
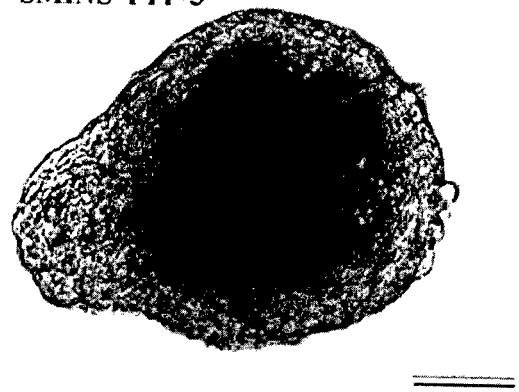
FIG. 3 provides images showing (a) a neurosphere of SMINS-TTF cells induced from adult mouse tail-tip fibroblasts (TTF) using three small "core" molecules (BIX01294, RG108 and PD325901) (ie SMINS-TTF-3) under bright field microscopy, scale bar: 100 μm; (b) ALP staining of SMINS-TTF-3 cells; and (c) RT-PCR analysis of typical neural stem cell gene expression from NS, SMINS-TTF-3 and MEF.
Figure 3B:
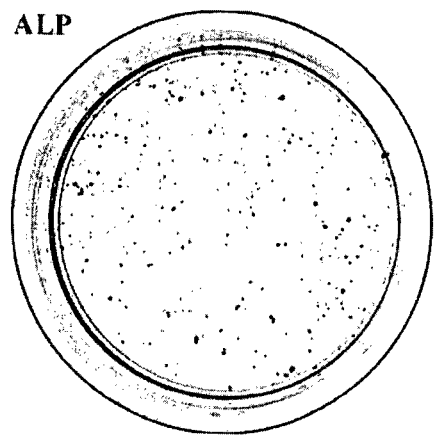

To confirm the efficacy of the protocol to obtain SMINS cells from fibroblasts and to eliminate a potential contamination from skin-derived neural crest stem cells, the protocol was applied to TTF cells isolated from adult mouse tails which had been stripped of skin. It was found that, just like MEF, TTF could also robustly form neurospheres after the 6 cycles of induction with the "core" combination of small molecules, BIX01294, RG108 and PD325901 (Table 9). These SMINS (SMINS-TTF-3) cells also resemble the native NS cells in morphology, gene expression patterns and multipotency (FIGS. 3a, b and c). In particular, ALP, Sox2 and SSEA-1 were assayed as described and all found to be expressed by the SMINS-TTF-3 cells. Moreover, SMINS-TTF-3 cells were found to express neural stem cell marker genes including Sox2, GFAP and Pax6 (FIG. 3a), but did not express the pluripotent genes Oct4 and Nanog (FIG. 3a). In addition, like NS cells, the SMINS-TTF-3 cells also expressed Gli2, which encodes a transcription factor thought to be involved in embryogenesis.

Figure 4A:
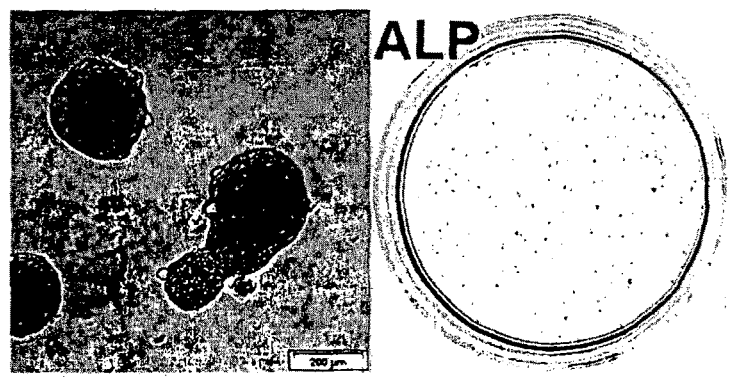
FIG. 4 provides images showing (a) the morphology and ALP staining of neurospheres of SMINS-TTF cells induced using a single small molecule (PD325901) (ie SMINS-TTF-1), scale bar: 200 μm; and (b) RT-PCR analysis of typical neural stem cell gene expression from NS, SMINS-TTF-1 and MEF.
Figure 4B:
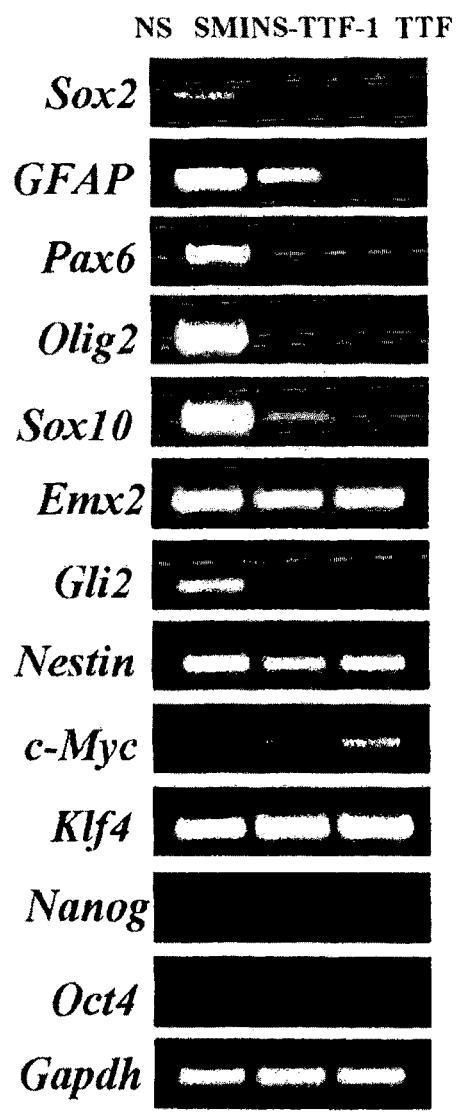
Figure 5A:
FIG. 5 provides images showing different morphologies of long-term differentiated SMINS-TTF-3 cells induced using three small molecules (BIX01294, RG108 and PD325901) obtained under phase contrast, Scale bar: 200 μm.
Figure 5B:
Figure 5C:
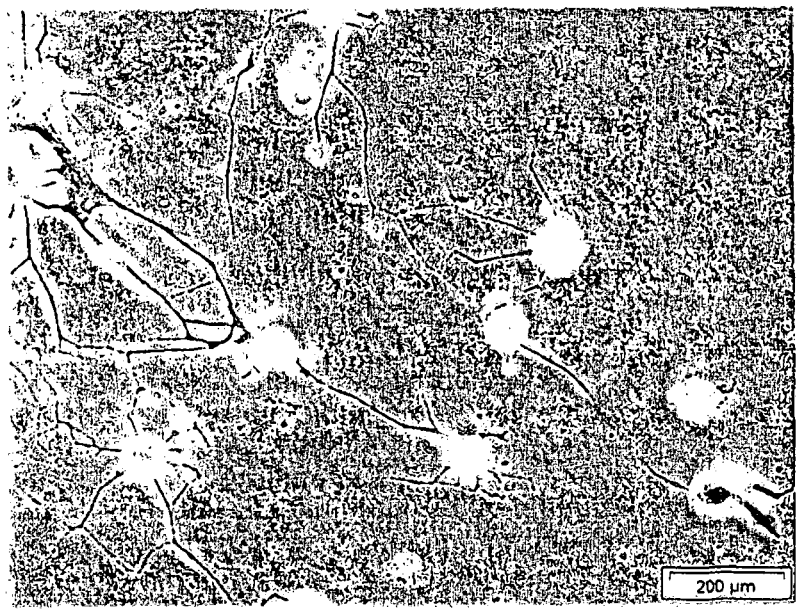
Figure 5D:
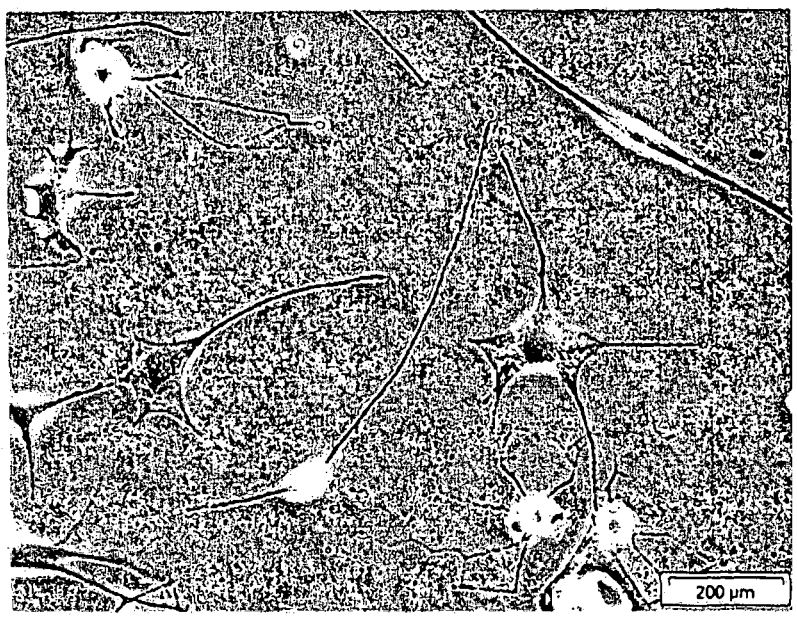

Surprisingly, it was also found that TTF could be induced to SMINS (SMINS-TTF-1) cells with a single small molecule, namely PD325901, after 5 induction cycles. These SMINS-TTF-1 cells are very similar to the native NS cells in morphology, gene expression patterns and multipotency (FIGS. 4a and b). In particular, ALP, Sox2 and SSEA-1 were assayed as described and all found to be expressed by the SMINS-TTF-1 cells. Further, the SMINS-TTF-1 cells were found to express neural stem cell marker genes including Sox2, GFAP and Pax6 (FIG. 4b), but did not express the pluripotent genes Oct4 and Nanog (FIG. 4b). Moreover, like NS cells and the SMINS-TTF-3 cells, the SMINS-TTF-1 cells also expressed the Gli2 gene. There were, however, a few neurosphere-like cells that emerged from TTF with SCM, but these cells were found to be ALP-negative. This indicates that the small molecules play key roles in the reprogramming process. This clearly demonstrates that the protocol is reliable, reproducible and practical to induce the formation of neurospheres from mouse fibroblasts and the resulting SMINS cells are unlikely to have been derived from skin neural crest stem cells.

TABLE 9

| Combination of small molecules | ALP-positive neurosphere produced from MEF | ALP-positive neurosphere produced from TTF |
|---|---|---|
| valproic acid; BIX01294; RG108; PD325901; CHIR99021; vitamin C; A83-01 | Yes | nd[#] |
| BIX01294; RG108; PD325901; CHIR99021; vitamin C; A83-01 | Yes | nd[#] |
| valproic acid; RG108; PD325901; CHIR99021; vitamin C; A83-01 | No* | nd[#] |
| valproic acid; BIX01294; PD325901; CHIR99021; vitamin C; A83-01 | No* | nd[#] |
| valproic acid; BIX01294; RG108; CHIR99021; vitamin C; A83-01 | No* | nd[#] |
| valproic acid; BIX01294; RG108; PD325901; vitamin C; A83-01 | Yes | nd[#] |
| valproic acid; BIX01294; RG108; PD325901; CHIR99021; A83-01 | Yes | nd[#] |
| valproic acid; BIX01294; RG108; PD325901; CHIR99021; vitamin C | Yes | nd[#] |
| BIX01294; RG108; PD325901 | Yes | Yes |
| PD325901 | nd[#] | Yes |
| BIX01294 | nd[#] | No |
| RG108 | nd[#] | No |

*The cells were observed to dissociate from the cell culture dish during induction.
[#]Not determined.

Figure 6A:
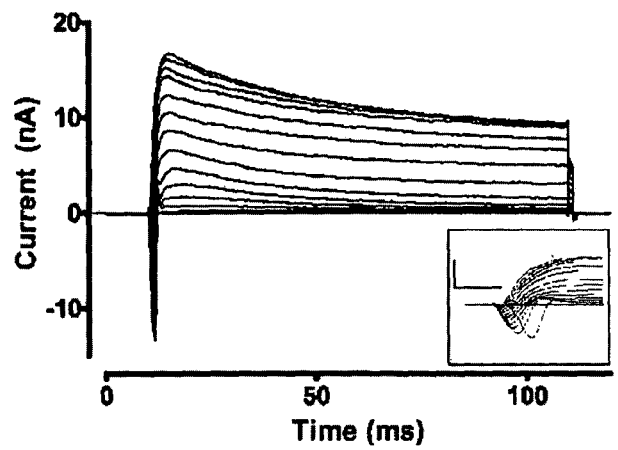
FIG. 6 provides graphical results of electrophysiology analysis of a subset of long-term differentiated cells (SMINS-TTF-3) showing; (a) the presence of both inward Na+ currents and outward K+ currents in response to electrical stimulation with steps from −70 to +70 mV (10 mV increments) from a holding potential of −80 mV. Representative trace with 100 ms steps, inset with 20 ms steps (inset scale bars represent 5 ms on x-axis, 10 nA on y-axis), (b) the mean maximal Na+ (closed circles) and K+ currents (open circles) (±SEM)(n=4), and (c) action potential firing in response to a current injection ((i) 20 pA for 5 s, (ii) & (iii) 50 pA for 5 s), or spontaneously (iv)
Figure 6B:
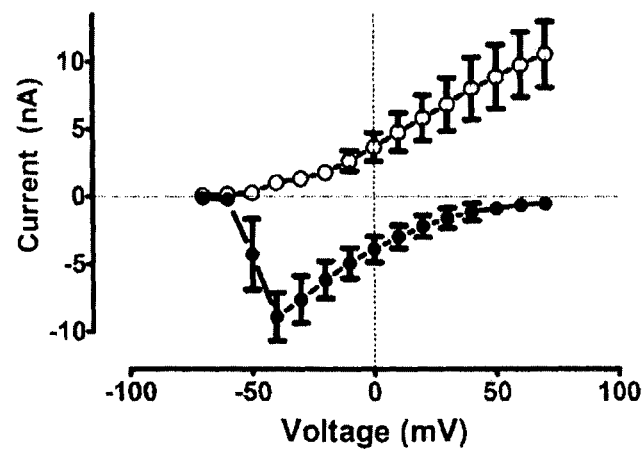
Figure 6C:
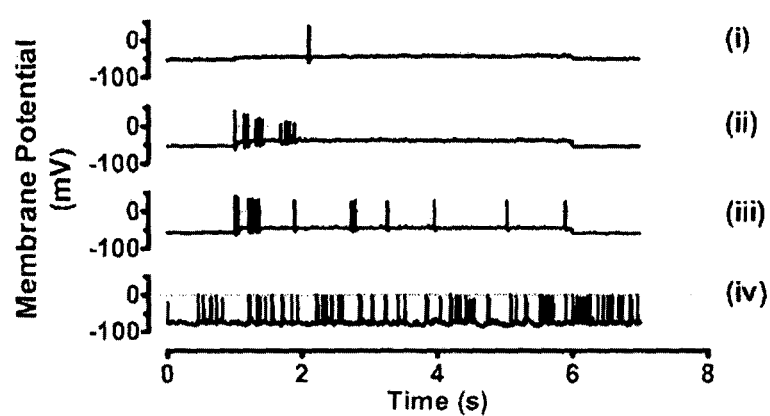
Figure 7A:
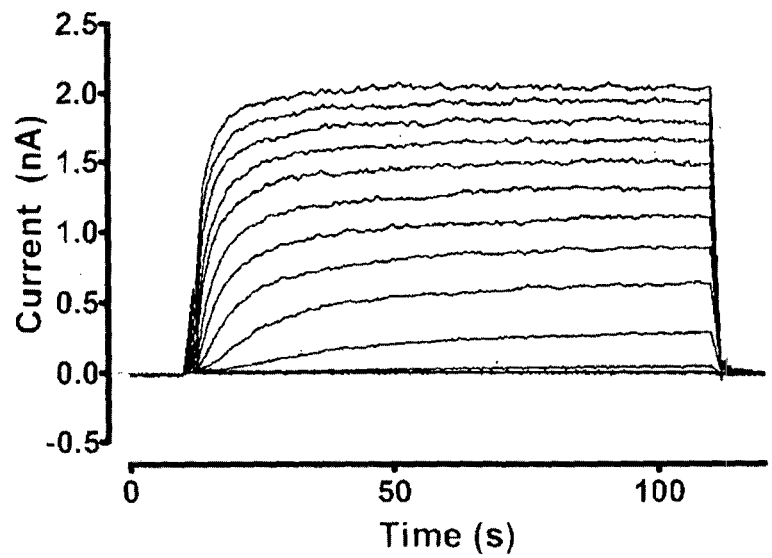
FIG. 7 provides graphical results of electrophysiology analysis of the majority of long-term differentiated SMINS-TTF-3 showing; (a) that for most of the long-term differentiated cells, there was only outward currents present in response to electrical stimulation with steps from −70 to +70 mV (10 mV increments) from a holding potential of −80 mV. Representative trace with 100 ms steps, and (b) the mean maximal K+ currents (±SEM)(n=a representative sample of 11 cells)
Figure 7B:
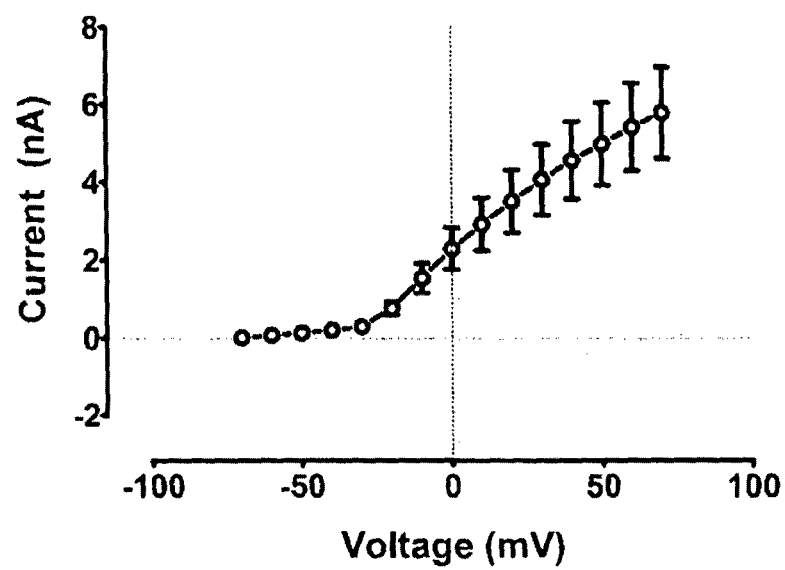
Figure 9A:
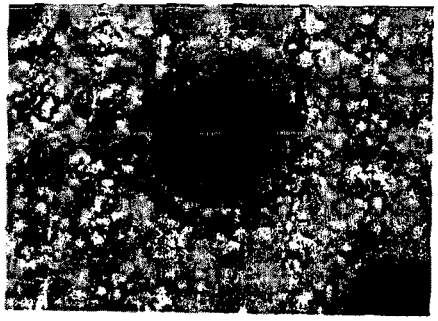
FIG. 9 provides micrograph images of colonies induced from HUCF cells using small molecules and stained with alkaline phosphatase (ALP), (a) induced with MEK inhibitor PD184352, (b) induced with MEK inhibitor PD0325901, (c) induced with a combination of PD184352, G9a HMTase inhibitor BIX01294, and DNA methylase inhibitor RG108. (d) induced with a combination of PD0325901, BIX01294 and RG108, (e) induced with a combination of PD0325901, BIX01294 and 5-aza-2'-deoxycytidine, and (f) induced with a combination of PD0325901, BIX01294 and 5-aza-2'-deoxycytidine.
Figure 9B:
Figure 9C:
Figure 9D:
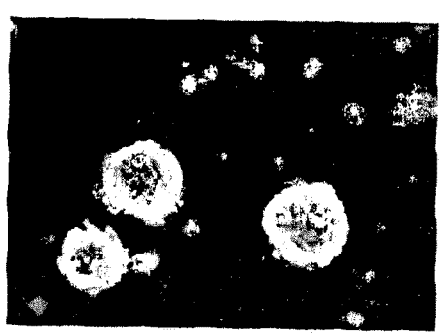
Figure 9E:
Figure 9F:
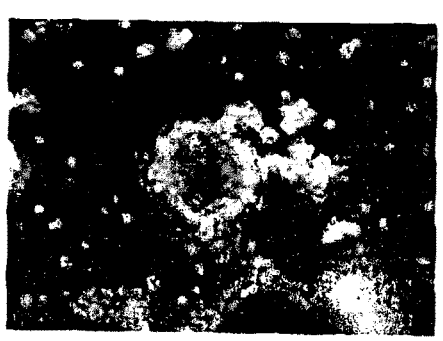
Figure 10A:
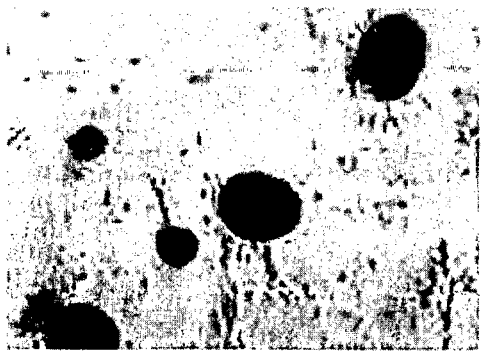
FIG. 10 provides phase contrast micrograph images of colonies induced from HUCF cells using small molecules and stained with alkaline phosphatase (ALP), (a) induced with MEK inhibitor U0216, (b) induced with a combination of U0216, BIX01294 and RG108, (c) induced with a combination of U0216, BIX01294, and 5-aza-2'-deoxycytidine.
Figure 10B:
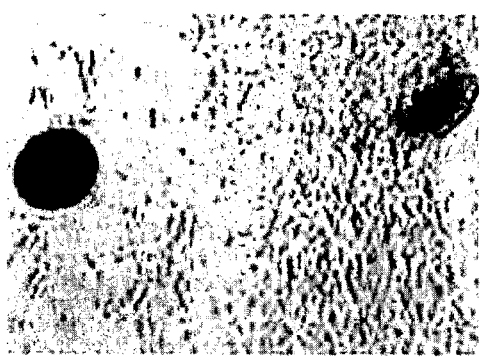
Figure 10C:
Figure 11A:
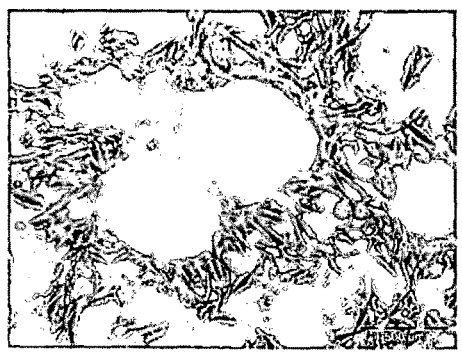
FIG. 11 provides micrograph images of colonies induced from HUCF cells using small molecules BIX01294 and RG108 and (a) 0 or (b-d) 7 days culturing in NSC media stained with alkaline phosphatase (ALP), with (b) showing numerous clones with variable sizes in 35 mm dish, (c) 4× magnification, (d) 10× magnification.
Figure 11B:
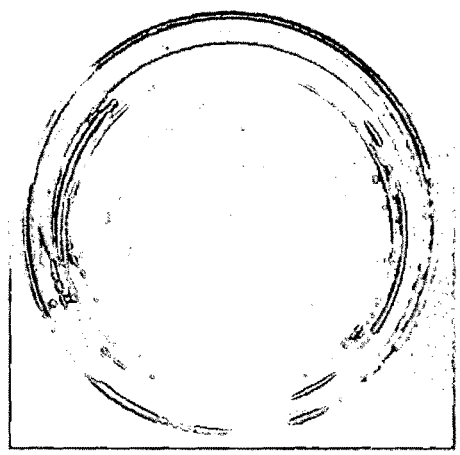
Figure 11C:
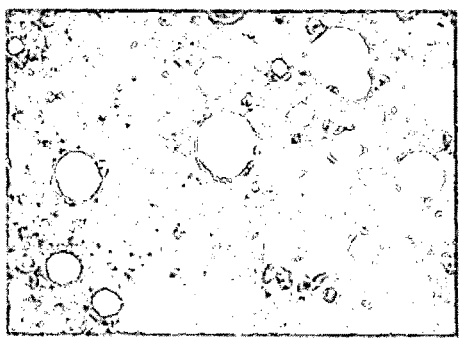
Figure 11D:
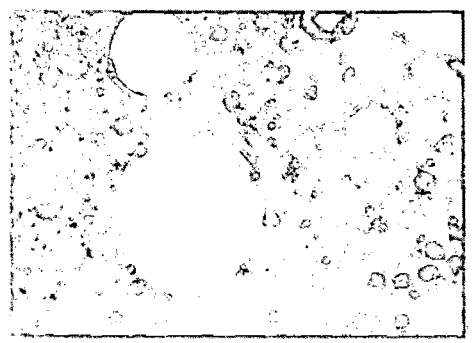
Figure 12A:
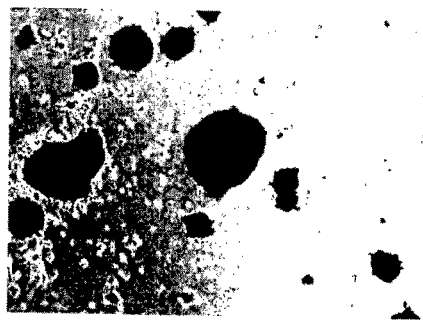
FIG. 12 provides micrograph images of colonies induced from HUCF cells using small molecules and stained with alkaline phosphatase (ALP), (a) induced with PD184352, (b) induced with U0216, (c) induced with a combination of PD184352, BIX01294 and RG108, (d) induced with a combination of U0216, BIX01294, and RG108, (e) induced with a combination of PD0325901, BIX01294 and 5-aza-2'-deoxycytidine, and (f) induced with a combination of PD0325901, BIX01294 and 5-aza-2'-deoxycytidine.
Figure 12B:
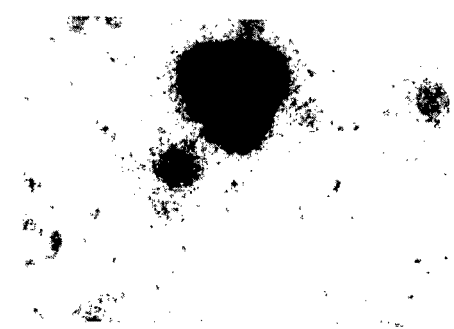
Figure 12C:
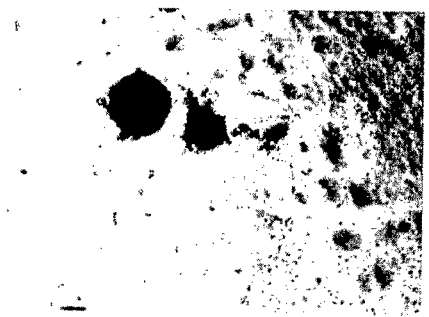
Figure 12D:
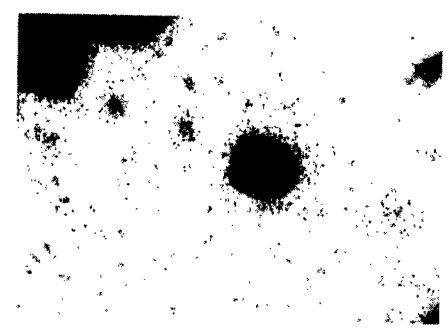
Figure 12E:
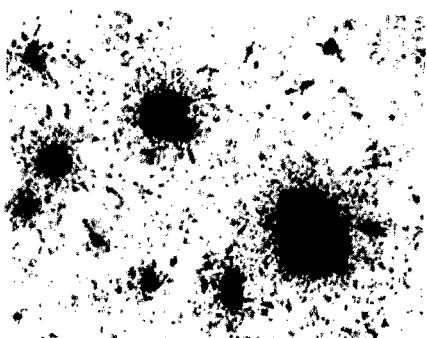
Figure 12F:
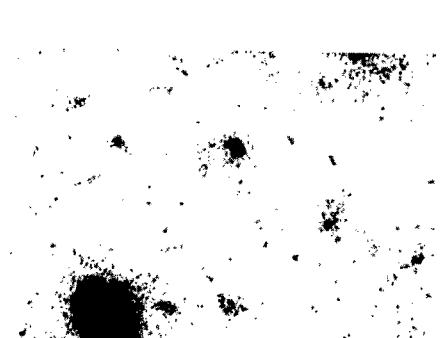

Experimentation was also conducted to assess whether the SMINS cells can differentiate into mature neurons. It was found that long-term differentiated SMINS-TTF-3 cells showed positive mature neuron markers, namely Synaptophysin and Vamp2 (results not shown). In addition, it was found that a small subset of long-term differentiated SMINS-TTF-3 cells displayed morphologies and unique phenotype similar to that of mature neurons (FIG. 5); in particular, electrophysiological analysis demonstrated a resting membrane potential of −57.7 mV±5.2 (n=5) in these cells which contained fast-inactivating inward Na+ currents in addition to slowly inactivating outward K+ currents (FIGS. 6a and b), and action potentials were either spontaneous or were able to be evoked in these cells by injecting current pulses (FIG. 6c). In contrast, the majority of neural-like differentiated cells displayed a different phenotype, with a more positive resting membrane potential, only K+-like outward currents with no inward Na+ currents or evoked action potentials (FIGS. 7a and b). This indicates that the SMINS cells are able to differentiate into functional neurons. In further experimentation with long-term differentiated SMINS-TTF-3 cells, it was found that these cells may also spontaneously differentiate into dopaminergic neurons (marked by green tyrosine hydroxylase (TH) immunofluorescence), cholinergic neurons (red choline acetyltransferase (ChAT) immunostaining) and peptidergic neurons (red vasoactive intestinal peptide (VIP) immunostaining) (results not shown).

Conclusion

The experimentation described in this Example demonstrates that mouse fibroblasts can be efficiently induced into NS cells using only small molecules (ie without using any exogenous transcription factors), and thereby avoiding integrating potentially harmful viral transfection vectors or the introduction of oncogenic transcription factors. These SMINS cells ought to be useful for research, disease modelling, drug development and drug screening as well as for clinical applications, such as treating neurological diseases and nerve damage. Moreover, as it is difficult to produce pluripotent stem cells and direct iPS cell differentiation into specific cell lineages[34], the SMINS cells described herein may have an advantage over iPS due to their high reprogramming efficiency and simple differentiation into astrocytes, neurons or oligodendrocytes in vitro, which also benefits the clinical applications of SMINS cells.

Example 2 Induction of Neural Stem Cells from Human Fibroblasts by Small Molecules Methods and Materials
Cells Human umbilical cord fibroblast (HUCF) cells were isolated directly from fresh human umbilical cord samples using a standard protocol and maintained in MEF medium (DMEM containing 10% FBS).

Induction of SMINS Cells

At passage 17, HUCF cells were labelled with an anti-p75NTR antibody and underwent cell sorting for p75-NTR expression as described below, p75NTR-negative cells were used for all experiments of the induction by small molecules described below. Two hours before induction, p75-NTR⁻ HUCF were seeded at 1.4×10$^5$ per 35 mm tissue culture dishes coated with poly-D-lysine. On Day 1, the cells were induced in human induced pluripotent stem cell culture medium (HIPS) (DMEM/F12 supplemented with 25% KSR (Invitrogen), 1% non-essential amino acids (Invitrogen), 1% L-glutamine (Invitrogen), 50 units ml-1 penicillin, 50 µg ml-1 streptomycin, 10 ng ml-1 bFGF, and 0.1 mM β-mercaptoethanol (Invitrogen)) containing various combinations of small molecules as described below. The small molecules were used at the following concentrations: 0.5 µM PD0325901, 0.5 µM PD184352 (Millipore Merck), 72 nM U0216 (Millipore Merck), 0.4 µM RG108. 10 mM 5-aza-2'-deoxycytidine (Millipore Merck) and 1 µM BIX01294. On day 2, the media was replaced with stem cell media (SCM) in the absence of small molecules as described in Example 1, except where indicated, the media was HIPS media in the absence of small molecules. On day 4, the cells were dissociated using 1 ml (1×) Tryple-E enzyme (Invitrogen) and seeded on 35 mm Petri dish with Neural Stem Cell (NSC) media (Neurobasal Medium (Invitrogen) supplemented with 10 ng/m bFGF and EGF with 50 units/ml penicillin, 50 µg/ml streptomycin). Colonies were maintained in NSC media for 7 days to induce neural stem cells unless stated otherwise. The small molecules and combinations thereof tested are shown in Table 10.

TABLE 10

Small molecule combinations tested

| FIGS. | MEK inhibitor | G9a HMTase inhibitor | DNA methylase inhibitor |
|---|---|---|---|
| 9, 12 | PD184352 | | |
| 9 | PD0325901 | | |
| 10, 12 | U0216 | | |
| 9, 12 | PD184352 | BIX01294 | RG108 |
| 9 | PD184352 | BIX01294 | 5-aza-2'-deoxycytidine |
| 9 | PD0325901 | BIX01294 | RG108 |
| 9, 12 | PD0325901 | BIX01294 | 5-aza-2'-deoxycytidine |
| 10, 12 | U0216 | BIX01294 | RG108 |
| 10, 12 | U0216 | BIX01294 | 5-aza-2'-deoxycytidine |
| 15, 16, 17, 18, 19, 20, 21, 22, 24 | | BIX01294 | |
| 11, 13, 14, 23, 24 | | BIX01294 | RG108 |

For some experiments (where indicated below including in Table 11), cells were incubated with small molecules in HIPS media for one day and SCM or HIPS media (in the absence of small molecules) for two days, and did not undergo the NSC culture step.

FACS Sorting and FACS Analysis

Fibroblast cells or SMINS were dissociated and incubated in 2% FBS-PBS solution with anti-P75-NTR antibody conjugated with FITC (Biosensis, 1:6, mouse) on ice for half hour. The cells were washed three times with ice-cold 2% FBS-PBS before running FACS sorting. P75-NTR negative fibroblasts were used in induction experiments. After induction, the p75-NTR positive SMINS cells were evaluated by FACS (Beckman Coulter Epics Altra HyperSort, using Expo MultiComp Software version 1.2B (Beckman Coulter, Miami, Fla., USA) compared with a blank control.

ALP Staining

Cells were induced with a combination of small molecules as described above and stained with ALP as described in Example 1, and examined using phase contrast microscopy. The experiments conducted are shown in Table 11.

TABLE 11

ALP experiments

| FIG. | MEK inhibitor | G9a HMTase inhibitor | DNA methylase inhibitor | Media at Day 2 and 3 | Days in NSC media |
|---|---|---|---|---|---|
| 9 | PD184352 | | | SCM | 7 |
| 9 | PD0325901 | | | SCM | 7 |
| 9 | PD184352 | BIX01294 | RG108 | SCM | 7 |
| 9 | PD184352 | BIX01294 | 5-aza-2'-deoxycytidine | SCM | 7 |
| 9 | PD0325901 | BIX01294 | RG108 | SCM | 7 |
| 9 | PD0325901 | BIX01294 | 5-aza-2'-deoxycytidine | SCM | 7 |
| 10 | U0216 | BIX01294 | | SCM | 7 |
| 10 | U0216 | BIX01294 | RG108 | SCM | 7 |
| 10 | U0216 | BIX01294 | 5-aza-2'-deoxycytidine | SCM | 7 |
| 11A | | BIX01294 | RG108 | HIPS | 0 |
| 11B-C | | BIX01294 | RG108 | HIPS | 7 |

Determining Efficiency of Neural Stem Cell Colony Induction

HUCF were induced with a combination of BIX01294 and RG108 as described above. Colony-containing media was made up to 3 ml with the culture media and divided into three 1 ml aliquots. Each 1 ml aliquot of colony-containing media was plated into one well of a poly-D-lysine and lamina coated 4 well plate for 2 hours. After attachment of the colonies, ALP staining was performed as follows. Colonies were washed with PBS twice and fixed in 4% paraformaldehyde solution for 20 minutes. Then ALP staining (1:50) was performed as described in Example 1. The efficiency of colony induction was determined by averaging the number of darkly stained colonies in the 3 wells divided by the number of cells seeded for induction (ie $1.4 \times 10^5$). Note that each colony contains many SMINS cells.

RT-PCR mRNA was extracted from cells induced using BIX01294 and RG108 in combination or BIX01294 alone. A cell lysate from SKSY5Y cells (a neuroblastoma cell line) was used as a positive control, and HUCF cells at passage 17 following p75-NTR negative selection was used as a negative control. RT-PCR was performed as described in Example 1 for expression of typical neural stem cell genes GFAP, Sox2, Olig2, Nestin, and pluripotent stem cell genes Oct4 and Nanog, and loading control gene GAPDH using the primers described in Example 1.

Immunocytochemistry Staining

Cells were induced with small molecules (BIX0124 alone or BIX0125 and RG108 in combination) as described above, with cells cultured in HIPS media at Days 2 and 3. Cells were cultured in NSC media for 0, 2 or 6 days as detailed below. Prior to immunofluorescence staining, cells were dissociated with Tryple-E enzyme as described above, and then incubated overnight at low density on poly-D-lysine coated coverslips in HIPS media prior to immunofluorescence staining.

Cells were then washed with PBS and then fixed with 4% paraformaldehyde for 10 min. After washing twice with PBS, cells were permeabilised with 0.1% Triton X-100 for 20 min. Cells were then washed twice and blocked in blocking buffer (a solution of PBS containing 1% FBS and 4% BSA) for 1 hour. Primary antibodies were diluted in blocking buffer in the following dilutions: anti-Sox2 (Millipore, 1:200, mouse), anti-SSEA-1 (Santa Cruz Biotechnology, 1:200, mouse), anti-glial fibrillary acidic protein (GFAP; Dako, 1:400, rabbit), anti-Map2 (Osenses, 1:1000, rabbit), anti-Olig2 (Osenses, 1:1000, rabbit), anti-Alpha-tubulin (Sigma, 1:1000, mouse), anti-neural/glial 2 (Abeam, 1:200), anti-nestin (DHSB, 1:1000), anti-Tuj1 Sigma, 1:300 and applied to the cells for 1 hour at room temperature or overnight at 4° C. Cells were washed three times with PBS and then secondary fluorescent antibodies (1:1000, Cy3 or Alexa-488) and counterstain with 10 μg/ml DAPI were applied for 1 hour at room temperature.

In one experiment, HUCF cells were induced as follows: At passage 17, HUCF cells were negatively selected for p75-NTR and then induced using BIX01294 alone in HIPS media for one day and HIPS media (no small molecules) for two days followed by culture in NSC media for 6 days. Meanwhile control HUCF cells at passage 17 were negatively selected for p75-NTR cells, and then passaged another 5 times. Cells were then stained with mouse anti-p75-NTR-FITC (Biosensis, 1:6, mouse) and counterstained with DAPI as described above.

Mouse neural stem cells were used as positive controls for immunocytochemistry experiments (data not shown). Images were captured using confocal microscopy.

The experiments conducted were as shown in Table 12.

TABLE 12

Immunocytochemistry experiments

| FIG. | G9a HMTase inhibitor | DNA methylase inhibitor | No of days in NSC media | Stained for |
|---|---|---|---|---|
| 13 | BIX01294 | RG108 | 0 | Sox2, DAPI |
| 14 | BIX01294 | RG108 | 0 | SSEA-1, DAPI |
| 15 | BIX01294 | | 6 | Sox2, DAPI |
| 16 | BIX01294 | | 6 | SSEA-1, DAPI |
| 17 | BIX01294 | | 0 | Sox2, DAPI |
| 18 | BIX01294 | | 0 | SSEA-1, DAPI |
| 19 | BIX01294 | | 6 | P75-NTR, DAPI |
| 20 | BIX01294 | | 6 | Nestin, DAPI |
| 21 | BIX01294 | | 6 | NG2, DAPI |
| 22 | BIX01294 | | 6 | GFAP, DAPI |
| 23 | BIX01294 | RG108 | 2 | Oli2, Tuj1, DAPI |

Results

Selection of p75-NTR Negative Cells for Induction

As p75-NTR is a neural crest stem cell marker, to eliminate any potential contamination of p75-NTR$^+$ cells in the preparation, FITC-labelled p75-NTR monoclonal antibodies were utilised for FACS sorting. As shown in FIG. 8B, p75-NTR sorting resulted in a p75-NTR$^-$ population with 99.8% purity. These p75-NTR$^-$ cells were used for induction. Immunocytochemistry confirmed that the p75-NTR$^-$ sorted cells were predominantly negative for p75-NTR (FIG. 8C).

Small Molecules can Induce Colonies of Neural Stem Cells

MEK inhibitors (PD0325901, PD18352, or U0216) alone or in combination with G9a HMTase inhibitors (BIX01294) and/or DNA methyltransferase inhibitors (RG108, or 5-aza-2'-deoxycytidine), and G9a HMTase inhibitors alone (BIX01294) were used in induction protocols. After day 3 of the induction protocol, colonies had started to aggregate and float. As shown in FIGS. 9 to 12, all MEK inhibitors alone or in combination with G9a HMTase inhibitors and DNA methylase inhibitors induced ALP positive colonies. ALP colony size varied considerably (see for example, FIG. 11 or 12). The ALP staining of colonies shows that various combinations of small molecules can reprogram fibroblast cells to be positive for ALP (which is a characteristic of neural stem cells), including a MEK inhibitor alone; a combination of a MEK inhibitor, a G9a HMTase inhibitor and a DNA methyltransferase inhibitor; or a combination of a G9a HMTase inhibitor and a DNA methyltransferase inhibitor. Additionally, the same results were produced when three different MEK inhibitor analogues were used (ie PD184352, PD0325901 or U0216), or when two different DNA methylase inhibitors were used (ie RG108 or 5-aza-2'-deoxycytidine). Accordingly, this experiment suggests that the induction method using small molecules in the absence of polynucleotide or polypeptide reprogramming factors induces neural stem cell colonies (neurospheres).

ALP+ Colony Induction Efficiency

Cells were induced with a combination of BIX01294 and RG108 as described above and stained with ALP. Following ALP staining, darkly stained colonies were present, some of which were large, and some of which were small. Large, darkly stained colonies were counted. On average, 131 large, darkly stained colonies were present per $1.4 \times 10^5$ fibroblast cells seeded, resulting in a colony induction efficiency of 0.09%. Note that many neural stem cells may be present in each colony.

However, it is worth noting that the cloning efficiency is approximately 100%. That is, $1.4 \times 10^5$ fibroblast cells were seeded, and approximately $7 \times 10^6$ cells are present after the induction cycle (prior to culture in NS medium). After 7 days of culture in NS media, approximately $1.4 \times 10^5$ NSC clones are present.

Small Molecule Induced Colonies Express Neural Stem Cell Genes

Given the success in reprogramming HUCF to have characteristics of neural stem cell colonies, an induction protocol using a combination of a G9a HMTase inhibitor and a DNA methyltransferase inhibitor or a G9aHMTase inhibitor alone was examined in further detail. HUCF were induced to produce neural stem cell colonies as outlined above using the G9a HMTase inhibitor BIX01294 alone or in combination with the DNA methylase inhibitor RG108. Cells were then cultured in NSC media for 0, 2 or 6 days. Following induction, cells were examined for expression of neural stem cell genes including Sox2 (a neural stem cell transcription factor that regulates neural stem cell lineages), SSEA-1 (a marker for embryonic stem cells and neural stem cells), p75-NTR (a neural crest stem cell marker), nestin (a neural stem cell marker), NG2 (oligodendrocyte progenitor marker) and GFAP (an astrocyte lineage marker).

As shown in FIGS. 13 and 14, following induction with BIX01294 and RG-108 (in the absence of incubation in NSC media), cells were present that clearly expressed Sox2 and SSEA-1 (fibroblasts were negatively stained). Similarly, induction with BIX01294 alone followed by culture in NSC media for 0 or 6 days resulting in a number of cells that clearly expressed Sox2 and SSEA-1 (6 days: FIGS. 15 and 16; 0 days: FIGS. 17 and 18). Accordingly, the reprogramming protocol using a G9a HMTase inhibitor alone, or a G9a HMTase inhibitor and a DNA methyltransferase inhibitor in combination, induce HUCF to express the neural stem cells genes Sox2 and SSEA-1, with or without the second step of culturing in NSC media, indicating that the induction protocol can reprogram HUCF to potential neural stem cells.

Small Molecules Induced Colonies Express Neural Lineage Markers

Figures 19A, 19B, 19C:
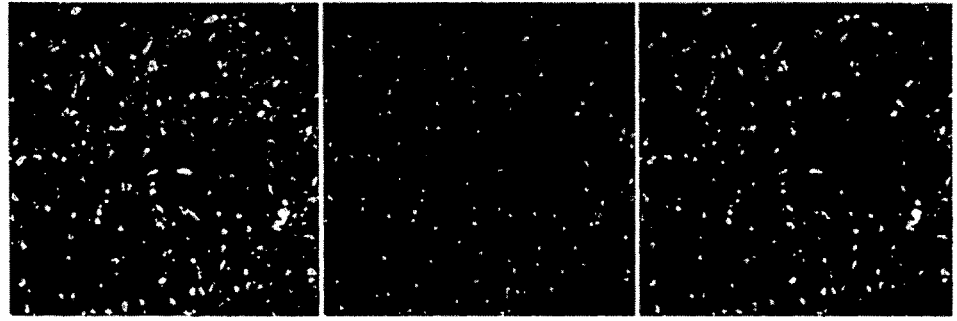
FIG. 19 provides immunofluorescence micrographs of (a-c) cells induced from HUCF, which at passage 17, were negatively selected for p75-NTR and then induced using BIX01294 alone in HIPS media for one day and HIPS media (no small molecules) for two days followed by culture in NSC media for 6 days, and (d-f) HUCF cells, which at passage 17, were negatively selected for p75-NTR cells, and then passaged another 5 times, stained for (a, d) p75-NTR, (b, e) DAPI, and (c, f) N75-NTR and DAPI combined image.
Figures 19D, 19E, 19F:
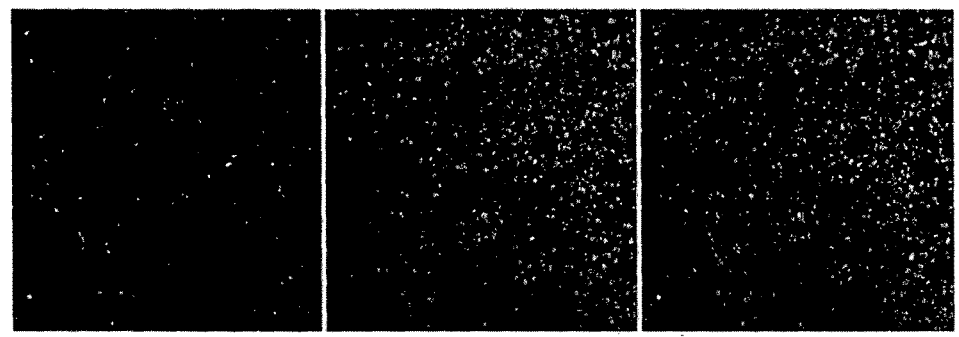
Figures 20A, 20B, 20C:
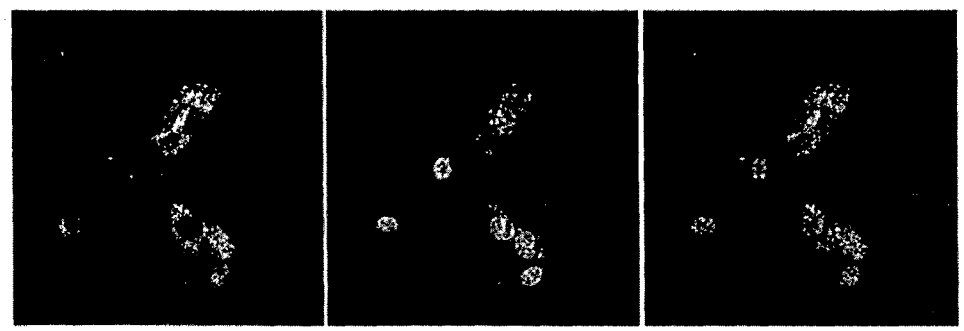
FIG. 20 provides immunofluorescence micrographs of cells induced from HUCF using BIX01294 alone in HIPS media for one day and HIPS media (no small molecules) for two days followed by culturing for 6 days in NSC media, stained for (a) nestin, (b) DAPI, and (c) nestin and DAPI combined image.
Figures 21A, 21B, 21C:
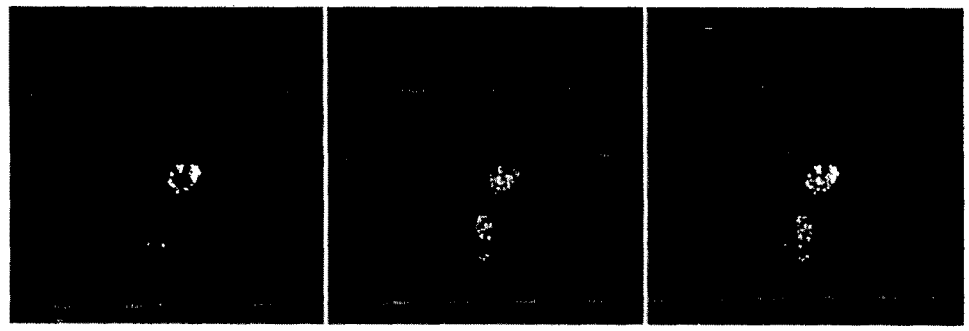
FIG. 21 provides immunofluorescence micrographs of cells induced from HUCF using BIX01294 alone in HIPS media for one day and HIPS media (no small molecules) for two days followed by culturing for 6 days in NSC media, stained for (a) NG2, (b) DAPI, and (c) NG2 and DAPI combined image.
Figures 22A, 22B, 22C:
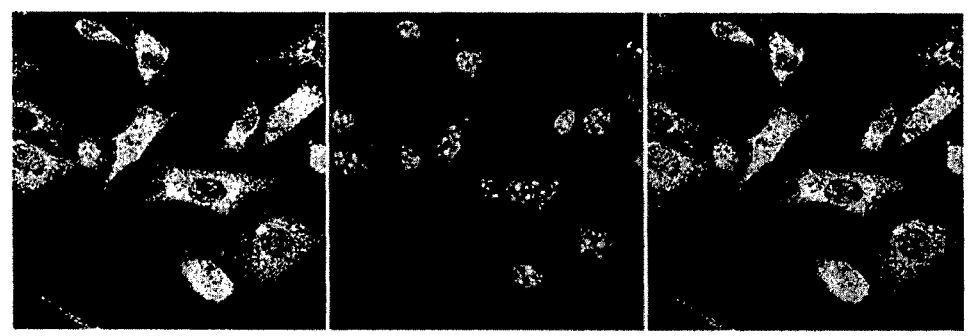
FIG. 22 provides immunofluorescence micrographs of cells induced from HUCF using BIX01294 alone in HIPS media for one day and HIPS media (no small molecules) for two days followed by culturing for 6 days in NSC media, stained with (a) GFAP, (h) DAPI, and (c) GFAP and DAPI combined image, compared to HUCF cells stained for (d) GFAP or (E) DAPI.
Figures 22D, 22E:
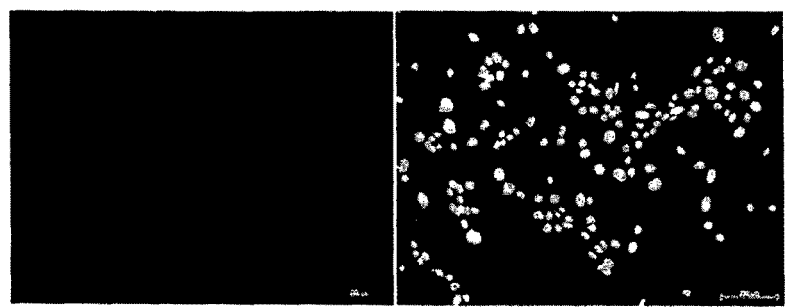
Figures 23A, 23B:
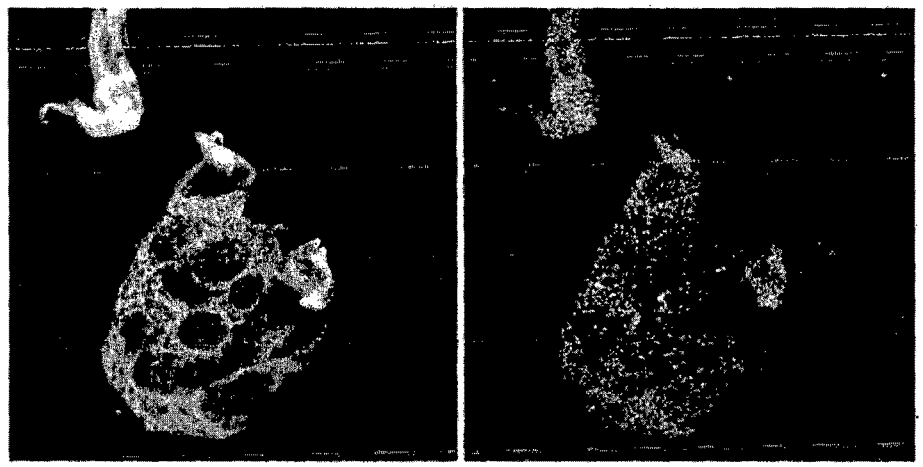
FIG. 23 provides immunofluorescence micrographs of cells induced from HUCF using BIX01294 alone in HIPS media for one day and HIPS media (no small molecules) for two days followed by culturing for 6 days in NSC media, stained with (a) Olig2, (b) Tuj1, (c) DAPI, and (d) combined Olig2, Tuj1, and DAPI image, compared to HUCF cells stained for (e) Tuj1 or (f) GFAP background staining.
Figures 23C, 23D:
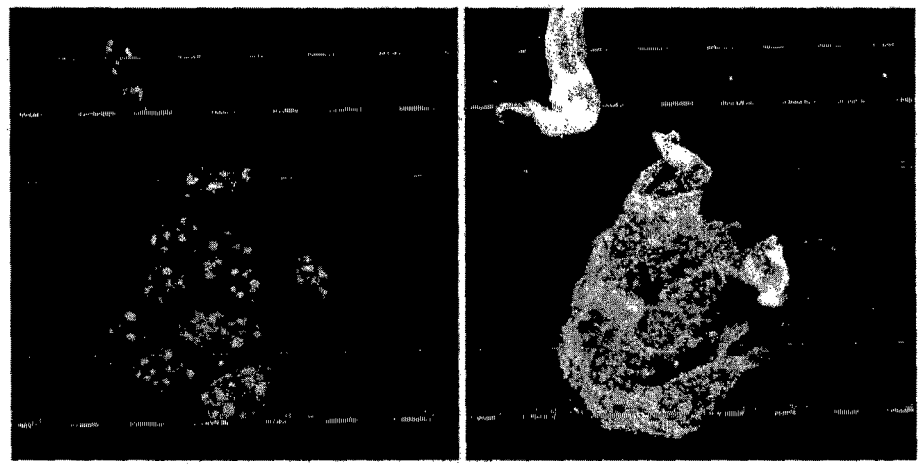
Figures 23E, 23F:
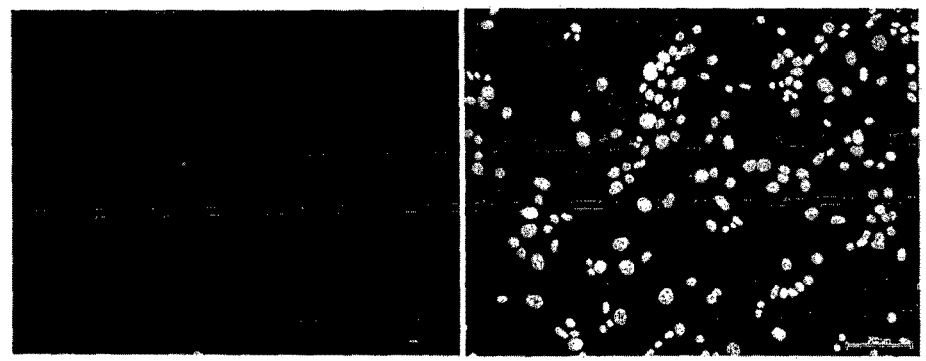

Immediately after neural stem cell induction with BIX01294 and culturing in NSC media, the ability of the induced colonies to express neural lineage markers was examined. FIG. 19 compares p75-NTR staining on cells induced from p75-NTR− HUCF using BIX01294 alone and then incubated for 6 days in NSC media to control p75-NTR− HUCF cells. The results clearly show marked upregulation of the neural crest cell marker p75-NTR− in the BIX01294 induced cells, indicating that at least some of the cells induced with BIX01294 are potential neural crest stem cells. Further, BIX01294 induced cells additionally express the neural stem cell marker nestin, indicating that the cells are neural stem cells (FIG. 20); and some BIX01294 induced cells express the oligodendrocyte progenitor markers NG2 (FIG. 21) and Olig2 (FIG. 23), the astrocyte marker GFAP (FIG. 22) and mature neuronal marker Tuj1 (FIG. 23). These figures indicate that these cells have not fully differentiated, showing their primitive morphology and the simultaneous expression of multiple neural lineage markers. With the increase in time in the NSC differentiation medium, it is expected that these cells will become fully differentiated neural cells in the same manner as shown for SMINS induced from mouse fibroblasts in Example 1.

Figure 24:
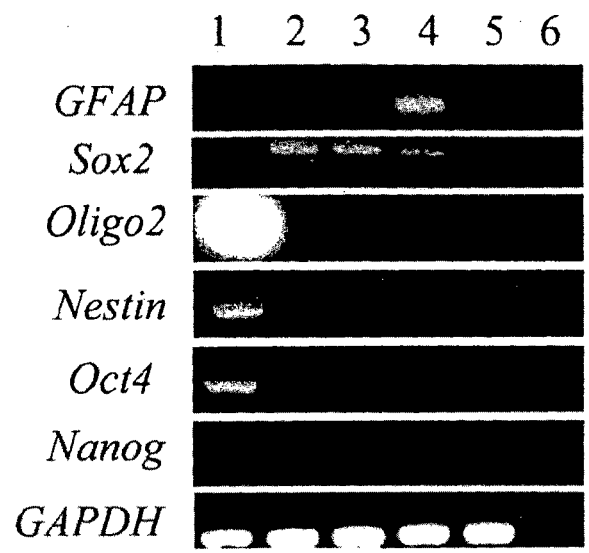
FIG. 24 provides an image showing RT-PCR analysis of expression of typical neural stem cell genes GFAP, Sox2, Olig2, Nestin, and pluripotent stem cell genes Oct4, Nanog and loading control gene GAPDH from (Lane 1) cell lysate of SKSY5Y cells (neuroblastoma cells, positive control), (Lane 2) cells induced from HUCF using BIX01294 and RG108 in combination in HIPS media for one day and HIPS media (no small molecules) for two days, (Lane 3) cells induced from HUCF using BIX01294 alone in HIPS media for one day and HIPS media (no small molecules) for two days, (Lane 4) cells induced from HUCF using BIX01294 alone in HIPS media for one day and HIPS media (no small molecules) for two days followed by culturing for 6 days in NSC media, (Lane 5) HUCF at passage 17 following p75-NTR negative selection (negative control), (Lane 6) blank control without cDNA.

RT-PCR Results Confirm the Successful Induction of Human NSC with Small Molecules RT-PCR for neural stem cell markers and pluripotent stem cell markers was performed on mRNA from colonies induced by the BIX01294 and RG108 or BIX01294 alone. As shown in FIG. 24, clones induced by BIX01294 and RG108 combination, or Bix01294 alone, expressed Sox2 immediately after induction (prior to culture in NSC media), whereas p75-NTR− HUCF (in the absence of small molecule induction) did not. After culture in NSC medium, the small molecule induced cells unregulated the neural lineage markers nestin, olig2 and GFAP. However, none of the small molecule induced cells expressed pluripotent genes Oct4 and Nanog.

Discussion

Example 2 establishes that small molecules, in the absence of polypeptide or polynucleotide reprogramming factors, can be used to induce (or reprogram) somatic cells such as human embryonic fibroblast cells (HUCF) into SMINS cells that express neural stem cell markers. It was demonstrated that a combination of the three small molecules (a G9a HMTase inhibitor, a MEK inhibitor, and a DNA methyltransferase inhibitor), two small molecules (a G9a HMTase inhibitor and a DNA methyltransferase inhibitor; or a G9a HMTase inhibitor and a MEK inhibitor) and a single small molecule (a G9a HMTase inhibitor or a MEK inhibitor) are capable of inducing colonies and cells to express the neural cell marker, ALP. The induction protocol using a combination of a G9a HMTase inhibitor and a DNA methyltransferase inhibitor or a G9a HMTase inhibitor alone was studied in further detail, and found that the resulting cells expressed the neural stem cell genes Sox2 and SSEA-1, indicating the cells are neural stem cells. Additionally, cells induced with the G9a HMTase inhibitor alone following just 6 days in NSC media were found to express the neural crest cell marker p75-NTR, the neural stem marker nestin, the oligodendrocyte progenitor markers NG2 and Olig2, the astrocyte marker GFAP, and neuronal marker Tuj1. These results show that the SMINS cells, following 6 days in NSC, have a primitive morphology and simultaneously express multiple neural lineage markers, indicting the cells have the potential to differentiate into difference cells in the neural lineage. It is expected that these cells would fully differentiate into various neuronal cells in the same manner as shown for the mouse fibroblasts. Moreover, the similarity of the results obtained in the mouse cells as compared to the human cells indicates that the mouse model is a good model for producing human SMINS cells.

Example 3 Characterisation of Neural Stem Cells Induced from Mouse MEF or TTF Using Small Molecules Methods and Materials
Cell Culture Mouse adult tail-tip fibroblasts (TTF), mouse embryonic fibroblasts and native mouse neural stem (NS) cells were isolated and cultured as described in Example 1.

Induction of SMINS Cells

Cells were induced with PD325901 alone; three small molecules (BIX01294, RG108, and PD325901); or seven small molecules (PD325901, valproic acid, BIX01294, RG108, CHIR9901, vitamin C, and A83-01) as follows. MEF or TTF were seeded at $1.4 \times 10^5$ per 35 mm dish coated with feeder cells before induction. The cells were induced in 6 cycles. On the first day, the cells were induced in stem cell culture medium (DMEM supplemented with 15% FBS, 1% non-essential amino acids (Invitrogen), 1% L-glutamine (Invitrogen), 50 units penicillin, 50 µg ml$^{-1}$ streptomycin, 0.1 mM β-mercaptoethanol (Invitrogen), and 1,000 Units ml$^{-1}$ leukaemia inhibitory factor (LIF) (Millipore)) containing small molecules. The cells were cultured in stem cell culture medium (SCM) for the next two days. Then, the cycle was repeated 5 times. Next, the cells were passaged and suspended in a drop of 20 µl SCM containing at least 50 cells for two days. Finally, the cells were cultured in the neural stem cell medium (DMEM/F12 (Invitrogen) supplemented with B-27 [1:50, Gibco], 50 units ml$^{-1}$ penicillin, 50 µg ml$^{-1}$ streptomycin, 8 mM HEPES buffer, 20 ng ml$^{-1}$ EGF, 10 ng ml$^{-1}$ bFGF) for two weeks. Native NS cells were cultured from mouse brain in the neural stem cell medium as positive controls.

In Vitro Differentiation of SMINS Cells

SMINS cells were differentiated as described in Example 1, except that for astrocyte differentiation, cells were cultured in NS cell culture medium containing 1% N2 (Invitrogen) without EGF and bFGF for one week; for neurons, cells were cultured in NS cell culture medium containing 1% N2 (Invitrogen) without EGF and bFGF for three weeks; and for mature neurons, cells were cultured in mature neural solution for one month.

RT-PCR and RT Profiler PCR Array

Total RNA was extracted using the RNeasy Mini. Kit (Qiagen) with on-column DNA digestion. Total RNA (500 ng) was converted to cDNA by Superscript III Direct cDNA Synthesis System (Invitrogen). PCR was performed using the primers described in Supplementary Table 4. The RT profiler PCR array was carried out using the Mouse Neurogenesis and Neural Stem Cells PCR Array (Qiagen).

ALP Staining

ALP staining was performed as described in Examples 1 and 2. Cells were either cultured in suspension culture (ie cultured in a petri dish in the absence of poly-D-lysine or laminin coating), or were cultured in an attachment culture (where the culture dish was coated with a substrate that induces adherence such as poly-D-lysine, laminin or matrigel).

Immunocytochemistry Staining

SCM was added to NS and SMINS cells overnight. For the immunocytochemistry staining, cells were washed with PBS and then fixed with 4% paraformaldehyde for 10 min. After washing twice with PBS, cells were permeabilised with 0.1% Triton X-100 for 20 min. Cells were then washed twice and blocked in a solution of PBS containing 1% FBS and 4% BSA for 1 hour. Primary antibodies were diluted in blocking buffer and applied for 1 hour at room temperature or overnight at 4° C. Primary antibodies were used at the following dilution: Sox2 (Millipore, 1:200, mouse), SSEA-1 (Santa Cruz Biotechnology, 1:200, mouse), GFAP (Dako, 1:400, rabbit), Map2 (Osenses, 1:1000, rabbit), Olig2 (Osenses, 1:1000, rabbit), Vamp2 (Osenses, 1:2000, rabbit), NeuN (Biosensis, 1:500, mouse) Alpha-tubulin (Sigma, 1:1000, mouse) and O4 (Millipore, 1:200, mouse). Cells were washed three times with PBS and then applied with secondary fluorescent antibodies (1:1000, Cy3 or Alexa-488) and 10 µg/ml DAPI for 1 hour at room temperature.

FACS Analysis

TTF cells were dissociated and incubated in 2% FBS-PBS solution with antibody P75 conjugated with FITC (Biosensis, 1:6, mouse) on ice for half hour. The cells were washed three times with ice-cold 2% FBS-PBS before running FACS. The positive fraction was evaluated by FACS (Beckman Coulter Epics Altra HyperSort, using Expo MultiComp Software version 1.2B (Beckman Coulter, Miami, Fla. USA)) comparing with a blank control.

In Vitro Differentiation of SMINS Cells

Cells were seeded at $0.5 \times 10^4$ on a PDL/laminin coated 4-well plate. For spontaneous differentiation, cells were cultured in NS cell culture medium containing 1% N2 (Invitrogen) without EGF and bFGF for one or three weeks. For the differentiation of mature neuron, the single SMINS cells were cultured in neurobasal medium (Invitrogen) containing B27 (2%) (Invitrogen), GlutaMAX (2 mM) (Invitrogen) and dibutyryl cAMP (0.5 mM) (Sigma) for four weeks Results Induction of Mouse TTF Cells with PD0325901 (Ie SMINS-TTF-1 Cells)

Figure 25A:
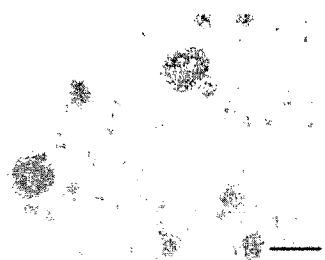
FIG. 25 provides micrographs of cells induced from mouse TTF using PD0325901 alone, (a) ALP stained SMINS-TTF-1 neurospheres cultured under bright field in suspension, (b) ALP stained SMINS-TTF-1 cells (passage 36) cultured on PDL/Latninin coated dish under bright field in attachment culture, SMINS-TTF-1 neurospheres dissociated and stained for typical neural stem cell markers (c) Sox2/DAPI, (d) SSEA-1/DAPI; typical neural stem cell markers (e) GFAP, (f) Tuj1, (g) DAPI, (h) merged staining for GFAP, Tuj1, and DAPI; (i) Olig2, (j) Tuj1, (k) DAPI, (l) merged staining for Olig2, Tuj1, and DAPI.
Figure 25B:
Figure 25C:
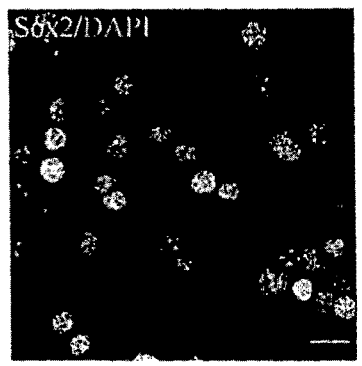
Figure 25D:
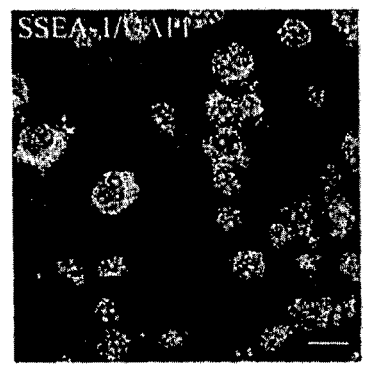
Figure 25E:
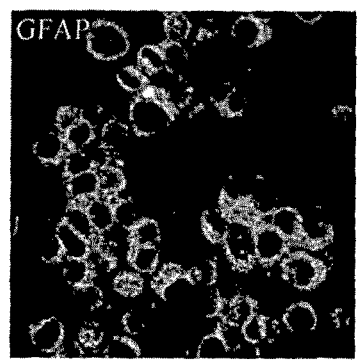
Figure 25F:
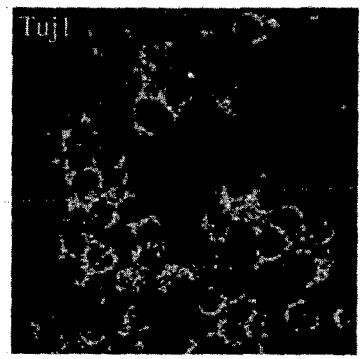
Figure 25G:
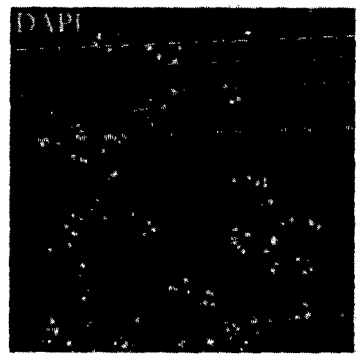
Figure 25H:
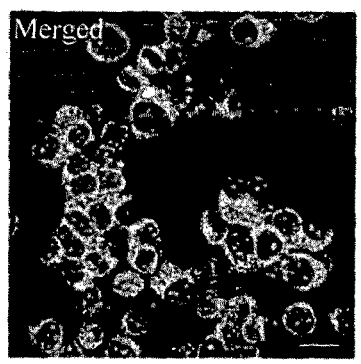
Figure 25I:
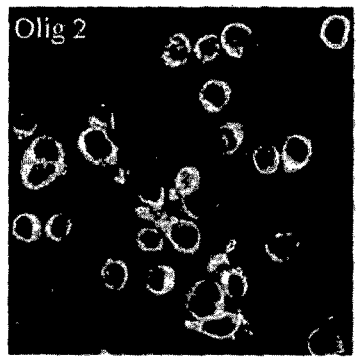
Figure 25J:
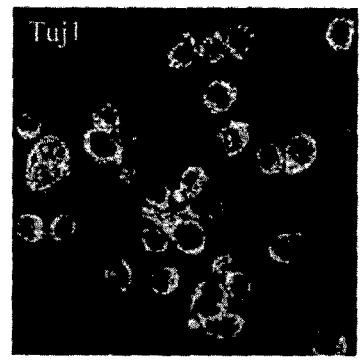
Figure 25K:
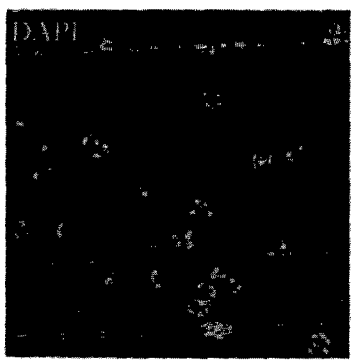
Figure 25L:
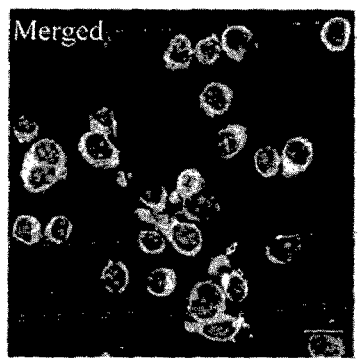
Figure 26A:
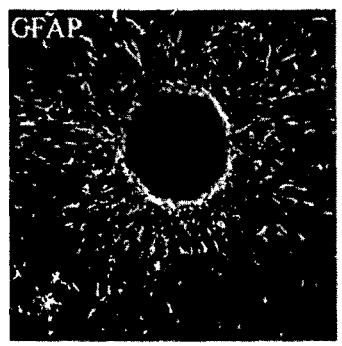
FIG. 26 provides micrographs of cells induced from mouse TTF using PD0325901 alone and then differentiated in vitro, SMINS-TTF-1 cells spontaneously differentiated into (a) astrocytes stained with GFAP, (b) neurons stained with Tuj1, (c) DAPI, (d) merged staining with GFAP, Tuj1, and DAPI following culture in NS medium for one week; and (e) neurons marked by Map2 and oligodendrocytes marked by O4 in NS medium for three weeks; and SMINS-TTF-1 cells cultured in neuralbasal medium for one month and stained for mature neuron markers (f) Vamp2 and (g) NeuN; (h) DAPI and (i) merged staining for Vamp2, NeuN, and DAPI; scale bar: 100 µm (a) and 10 µm (b, c).
Figure 26B:
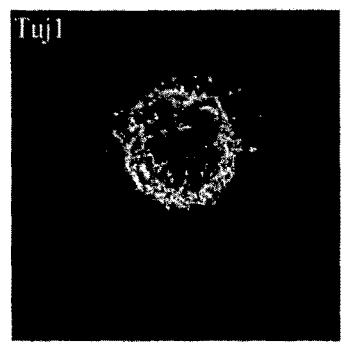
Figure 26C:
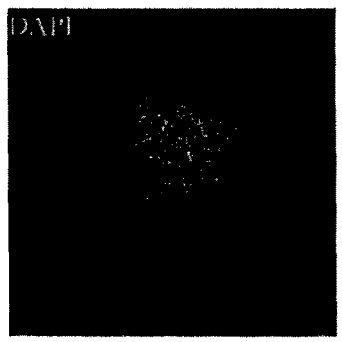
Figure 26D:
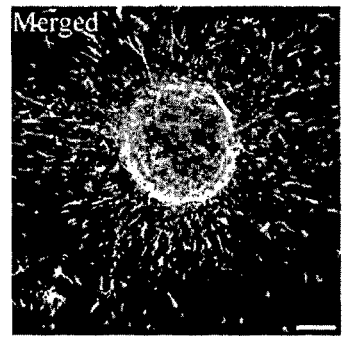
Figure 26E:
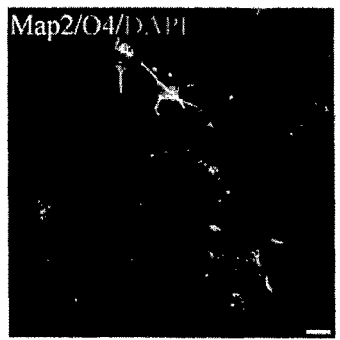
Figure 26F:
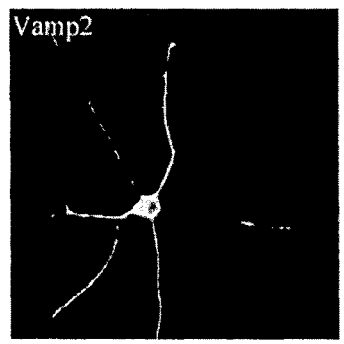
Figure 26G:
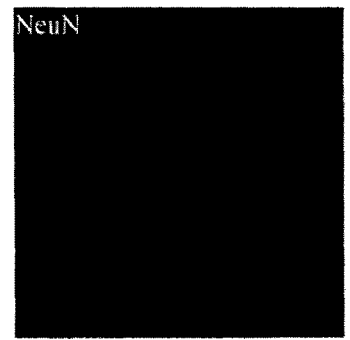
Figure 26H:
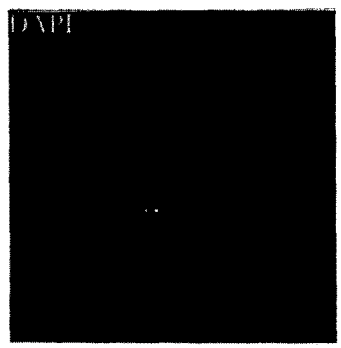
Figure 26I:
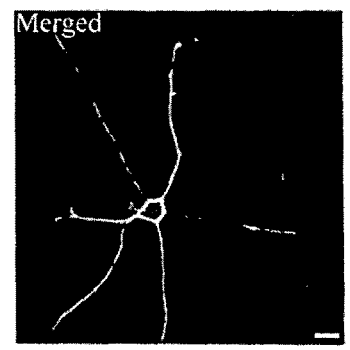
Figure 27A:
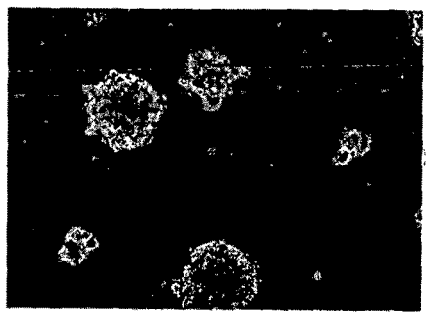
FIG. 27 provides phase contrast micrograph images of colonies induced from HUFC cells using (a) G9a HMTase inhibitor chaetocin, (b) chaetocin and RG108, (c) chaetocin and 5-aza-2'-deoxycytidine, (d) chaetocin, U0216 and 5-aza-2'-deoxycytidine (e) chaetocin, U0216 and RG108, (f) PD0325901, chaetocin and RG108, (g) PD0325901, chaetocin and RG108 following culture in NSC for four days at 10× magnification.
Figure 27B:
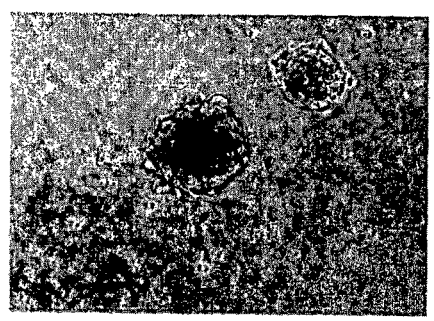
Figure 27C:
Figure 27D:
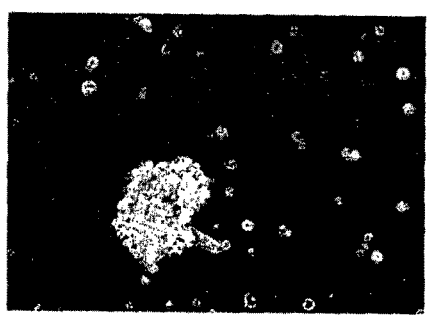
Figure 27E:
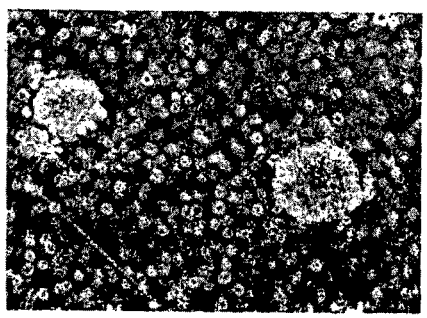
Figure 27F:
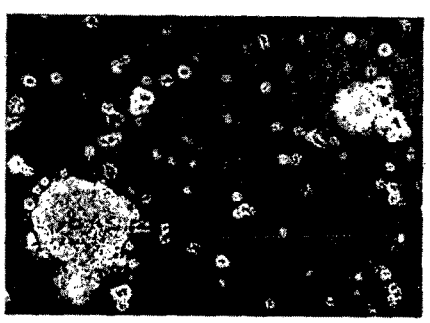
Figure 27G:
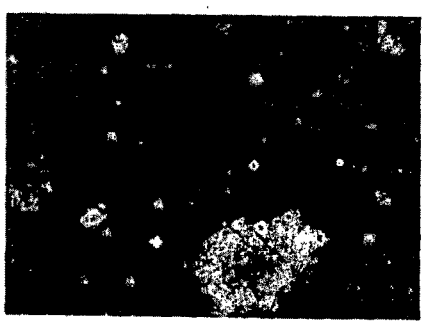
Figure 28A:
FIG. 28 provides micrographs of ALP stained colonies induced from HUFC cells using (a) G9a HMTase inhibitor chaetocin, (b) chaetocin and RG108, (c) chaetocin and 5-aza-2'-deoxycytidine, (d) chaetocin, U0216 and 5-aza-2'-deoxycytidine (e) chaetocin, U0216 and RG108, (f) PD0325901, chaetocin and RG108, and (g) PD0325901, chaetocin and RG108 following culture in NSC for four days at 10× magnification.
Figure 28B:
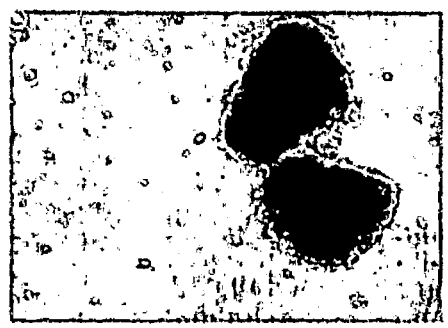
Figure 28C:
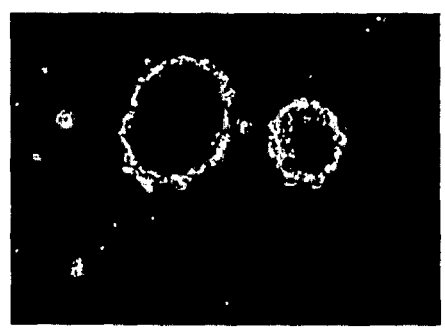
Figure 28D:
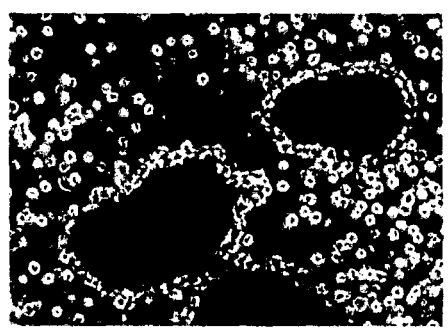
Figure 28E:
Figure 28F:
Figure 28G:

PD0325901 can induce TTF to SMINS (SMINS-TTF-1) cells after induction of 5 cycles. In order to further expel the neural crest contamination in TTF cells, TTF cells were sorted by FACS with p75-NTR. Only p75-NTR negative TTF cells were used for induction (98.7%, data not shown). These SMINS-TTF-1 cells are very similar to the native NS cells in morphology (FIG. 25a, b). In suspension culture, these cells form spheres with similar size and shape to that of neurospheres derived from embryonic mouse brain (FIG. 25a). In the adhering culture (FIG. 25b), these spheres differentiate and cells at the edge of sphere spread out, and were additionally Tuj1 positive, and some cells were GFAP+ positive and O4+. These different types of differentiated cells intermingled with each other. SMINS-TTF-1 cells also express the neural stem cell markers Sox2, SSEA-1, GFAP, Tuj1 and Olig2 (FIG. 25e, f, i, j) and neural stem cell marker genes including Sox2, GFAP, Olig2 and Gli2 (FIG. 4c). Just like neural stem cells, SMINS-TTF-1 cells do not express the pluripotent genes Oct4 and Nanog (FIG. 4c). Furthermore, SMINS-TTF-1 cells were able to differentiate into astrocytes (GFAP-positive cells, 19%; FIG. 26a-d), neurons (Map2-positive cells, 25%; FIG. 26e) or oligodendrocytes (O4-positive cells, 20%; FIG. 26e), mature neurons (Vamp2 positive cells; FIG. 26f). The method has been repeated more than 50 times and similar results were obtained. This indicates small molecules play key roles in the reprogramming process. This data clearly demonstrates that our protocol using small molecules is reliable, reproducible and practical to induce the formation of neurospheres from mouse fibroblasts and that the SMINS cells are unlikely to be derived from skin neural crest stem cells.

Induction of Mouse TTF Cells with BIX01294, RG108, PD0325901 (Ie SMINS-TTF-3 Cells)

Figure 3C:
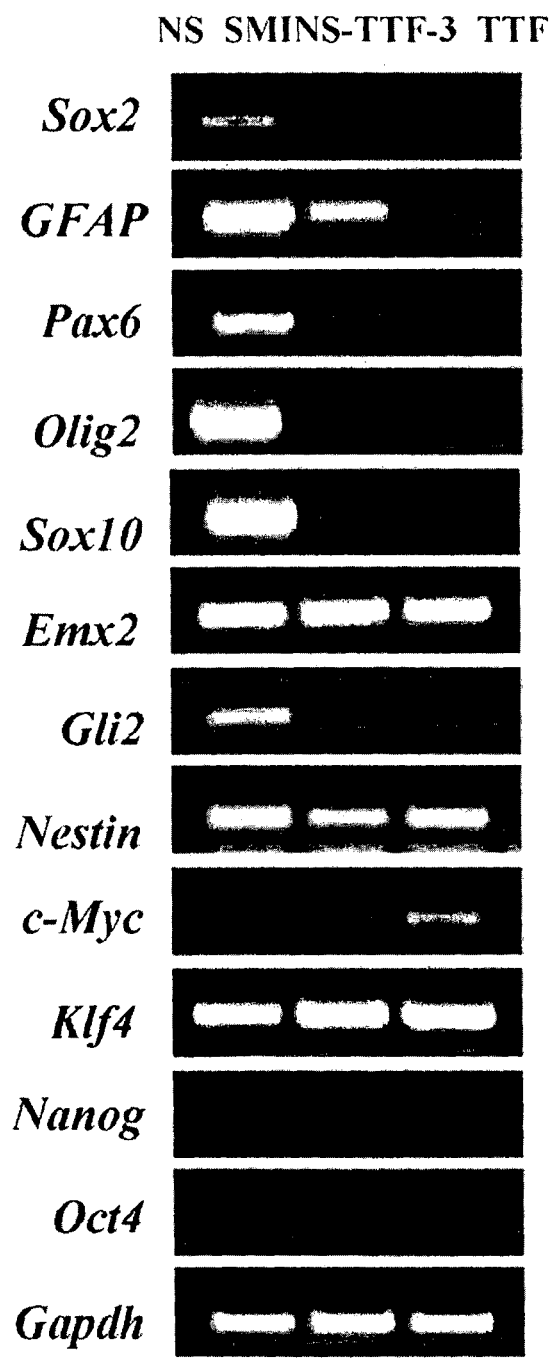

To further confirm the efficacy of the protocol to obtain SMINS cells from fibroblasts and to eliminate potential contamination from skin-derived neural crest stem cells, we isolated tail-tip fibroblasts (TTF) from adult mouse tails which had been stripped of skin. TTF (ie prior to induction) were found to be negative for the neural stem cells and nervous cell markers Sox2, SSEA-1, Map2, GAFP and Olig2 (data not shown). Just like MEF, TTF could also robustly form neurospheres after the 6 cycles induction protocol with these three small molecules BIX01294, RG108 and PD0325901. Similar to the data shown for the SMNS-TTF-1 cells, these SMINS (SMINS-TTF-3) cells resemble native NS cells in morphology (data not shown, but similar to that shown in FIG. 25a, b). SMINS-TTF-3 cells also express the neural stem cell markers Sox2, SSEA-1, GFAP, Tuj1 and Olig2 (data not shown, but similar to that shown in FIG. 25e, f, i, j). Reverse transcription PCR (RT-PCR) showed that SMINS-TTF-3 cells expressed neural stem cell marker genes including Sox2, GFAP, Olig2 and Gli2 (FIG. 3c) compared to TTF which do not show this expression. Similarly to neural stem cells, SMINS-TTF-3 cells do not express the pluripotent genes Oct4 and Nanog (FIG. 3c). Finally, in vitro differentiation assays showed that like SMINS-TTF-1 cells, SMINS-TTF-3 cells were able to differentiate into astrocytes (GFAP-positive cells, 24%), neurons (Map2-positive cells, 36%) or oligodendrocytes (O4-positive cells, 30%) (data not shown, but similar to data shown in FIG. 26 for SMINS-TTF-1 cells). Furthermore, like SMINS-TTF-1 cells, SMINS-TTF-3 cells were able to express mature neural markers Vamp2 and NeuN in mature neuron differentiation solution (data not shown but similar to data shown in FIG. 26 for SMINS-TTF-1 cells). SMINS cells did not express the fibroblast marker Alpha-tubulin (data not shown).

Induction of Mouse MEF Cells with PD325901, Valproic Acid, BIX01294, RG108, CHIR9901, Vitamin C, and A83-01 (Ie SMINS-MEF-7 Cells)

A combination of small molecules (Valproic acid, 1 µM; BIX01294, 1 µM; RG108, 0.04 µM; PD0325901, 1 µM; CHIR9901, 3 µM; Vitamin C, 25 µM; A83-01, 2.5 µM) was found to induce mouse embryonic fibroblasts (MEF) into NS cells. Fibroblasts were cultured alternatively in small molecule-containing stem cell culture medium for 1 day, and in stem cell culture medium (SCM) without small molecules for 2 days as cycle 1 and the cycle was repeated an additional 5 times. After the 6th cycle, the cells were cultured in suspension for 2 days and then in NS cell culture medium for 2 weeks. Like TTF, MEF after several passages (ie in the absence of induction) were negative to Sox2, SSEA-1, Map2, GFAP and Olig2 by immunocytochemistry (data not shown). In order to eliminate neural crest stem cells from mouse skin, only MEF that are negative to Sox2, SSEA-1, Map2, GFAP and Olig2 were used for induction. Following induction with seven small molecules, SMINS (SMINS-MEF-7) cells were able to be stably and homogenously expanded for more than 500 days without a significant reduction in the self-renewal capacity and were morphologically indistinguishable from classic neural stem cells (data not shown but similar to that shown for SMINS-TTF-1 in FIG. 25a, b). SMINS-MEF-7 cells also expressed the neural stem cell markers Sox2, SSEA-1, GFAP, Tuj1 and Olig2 (data not shown, but similar to that shown for SMINS-TTF-1 cells in FIG. 25c, d, e, f, i).

RT-PCR showed that compared to fibroblasts, SMINS-MEF-7 cells expressed neural stem cell marker genes including Sox2, GFAP and Olig 2 (FIG. 2a). Just like neural stem cells, SMINS-MEF-7 cells did not express the pluripotent genes Oct4 and Nanog (FIG. 2a).

To confirm the multipotency of the SMINS cells, in vitro differentiation assays were performed. SMINS-MEF-7 cells were able to spontaneously differentiate into astrocytes (GFAP-positive cells, 20%), neurons (Map2-positive cells, 31%) or oligodendrocytes (O4-positive cells, 36%) (data not shown, but similar to that shown for SMINS-TTF-1 cells in FIG. 26a, e). Moreover, SMINS-MEF-7 cells were able to express mature neural markers Vamp2 and NeuN in mature neuron differentiation solution (data not shown but similar to data shown for SMINS-TTF-1 cells in FIG. 26f, g). These results indicate that, like native NS cells, SMINS cells are multipotent in vitro.

Discussion

This example demonstrates that mouse fibroblasts can be efficiently induced into NS cells using only small molecules without using any exogenous transcription factors. Moreover, as it is difficult to direct the differentiation of pluripotent stem cells into specific cell lineages, these SMINS cells may have an advantage over iPS due to the easy differentiation into astrocytes, neurons or oligodendrocytes in vitro, which also is beneficial for the clinical applications of SMINS cells. Thus, these SMINS cells may have direct potential in clinical treatment of neurological disorders.

Example 4 Induction of Neural Stem Cells from HUCF Using Different Combinations of Small Molecules Using 6 Induction Cycles Method Human umbilical cord fibroblasts as described in Example 2 were seeded at $1.4 \times 10^5$ cells per 35 mm dish coated with feeder cells. The cells were induced in 6 cycles as follows. On the first day of each induction cycle, the cells were induced in stem cell culture medium (DMEM/F12 supplemented with 25% KSR, 1% non-essential amino acids (Invitrogen), 1% L-glutamine (Invitrogen), 50 units ml-1 penicillin, 50 µg ml-1 streptomycin, 0.1 mM β-mercaptoethanol (Invitrogen), and 5 ng ml-1 bFGF containing various small molecules as detailed in Examples 1 and 2. Then on the second day of the induction cycle, the cells were cultured in stem cell culture medium (SCM) for the next two days in the absence of small molecules. The cycle was repeated 5 times.

Finally, the cells were cultured in the neural stem cell medium (DMEM/F12 (Invitrogen) supplemented with B-27 (1:50, Gibco), 50 units ml-1 penicillin, 50 µg ml-1 streptomycin, 20 ng ml-1 EGF, 10 ng ml-1 bFGF) for two weeks. In some experiments, the resulting cells were differentiated in vitro as described in Examples 2 or 3.

Results and Discussion

The cells induced by this method resulted in ALP positive staining colonies in a similar manner to the results shown in Example 2 (data not shown) and stained positive for the following neural stem cell markers by immunocytochemistry: PSA-NCAMP, nestin, MAP2, O4, NeuN (data not shown), indicating that the six cycle induction method induces SMINS cells that express neural stem cell markers from HUCF cells in a similar manner to the single cycle induction method of Example 2.

Example 5 Induction of Neural Stem Cells from HUCF Using Different Combinations of Small Molecules Using 6 Induction Cycles Methods and Materials HUCF were isolated and maintained, and underwent p75-NTR cell sorting as described in Example 2. HUCF p75NTR negative cells were seeded at 1.4×10⁵ per 35 mm dish coated with Poly-D-Lysine (2 h) before induction. On the first day, the cells were induced in stem cell culture medium (DMEM/F12 supplemented with 25% KSR, 1% non-essential amino acids (Invitrogen), 1% L-glutamine (Invitrogen), 50 units ml-1 penicillin, 50 µg ml-1 streptomycin, 10 ng ml-1 bFGF, and 0.1 mM β-mercaptoethanol (Invitrogen) containing various small molecules combinations (0.5 µM PD0325, 0.2 µM chaetocin, 72 nM U0216, 0.4 µM RG108 and 10 mM 5-aza-2'-deoxycytidine. The cells were then cultured in stem cell culture medium (SCM) in the absence of small molecules for the next two days, by which time, colonies were starting to aggregate and float. Then on the fourth day, cells were dissociated using Tryple-E enzyme and seeded on 35 mm petri dish with Neural stem cell (NSC) media (Neurobasal supplemented with 10 ng ml-1 bFGF and EGF with 50 units ml-1 penicillin, 50 µg ml-1 streptomycin). Colonies were cultured in NSC media for 4 days to induce neural stem cells. The colonies were then picked up to perform ALP staining as described in Example 2.

TABLE 13

Small molecule combinations tested

| MEK inhibitor | G9a HMTase inhibitor | DNA methylase inhibitor |
|---|---|---|
|  | Chaetocin |  |
|  | Chaetocin | RG108 |
|  | Chaetocin | 5-aza-2'-deoxycytidine |
| U0216 | Chaetocin | 5-aza-2'-deoxycytidine |
| U0216 | Chaetocin | RG108 |
| PD0325901 | Chaetocin | RG108 |
| PD0325901 | Chaetocin | RG108 |

Results

Each of the combination of small molecules induced colonies from HUCF cells that appeared morphologically similar to those produced in the previous Examples (See FIG. 27). The colonies were positive when stained with ALP, similar to the colonies produced in the previous Examples (see FIG. 28). These results indicate that the tested combination of small molecules, all including the G9a HMTase inhibitor chaetocin, induced neural stem cells similar to those shown in Examples 1, 2 and 3.

Summary of Examples

Example 1 established that small molecules, in the absence of polypeptide or polynucleotide reprogramming factors, can be used to induce (or reprogram) somatic cells such as mouse embryonic fibroblasts (MEF) or adult tail tip fibroblasts (TTF) into neurospheres containing SMINS cells, that is multipotent cells that are morphologically indistinguishable from native neural stem cells and express the neural stem cell markers ALP, Sox2, SSEA1, GFAP, Pax6 and Olig2. Like neural stem cells, the SMINS did not express the pluripotent genes Oct4 and Nanog. A number of genes related to neuronal differentiation, axonal guidance and glial differentiation, such as Cdk5rap2, Pou4f1, S100b, Sema4d, Tnr and Vegfa, appeared to be up-regulated in SMINS cells. In vitro differentiation assays established that the SMINS were able to spontaneously differentiate into astrocytes (GFAP+), neurons (MAP2+) or oligodendrocytes (P25+). In directed differentiation assays, it was demonstrated that SMINS cells could be induced to preferentially differentiate into either astrocytes (GFAP+), neurons (MAP2+ and βIII-tubulin+) or oligodendrocytes (P25+), indicating that, like native NS cells, SMINS cells are multipotent in vitro. Long-term differentiated SMINS cells showed positive mature neuron markers, namely Synaptophysin and Vamp2 and a small subset of long-term differentiated SMINS cells displayed morphologies and unique phenotype similar to that of mature neurons, indicating that the SMINS cells are able to differentiate into functional neurons. These cells can also spontaneously differentiate into dopaminergic neurons (marked by green tyrosine hydroxylase (TH) immunofluorescence), cholinergic neurons (red choline acetyltransferase (ChAT) immunostaining) and peptidergic neurons (red vasoactive intestinal peptide (VIP) immunostaining). Example 1 established a combination of seven types of small molecules (ie a G9a HMTase inhibitor, a MEK inhibitor, a DNA methyltransferase inhibitor, a HDAC inhibitor, a GSK3 inhibitor, Vitamin C; and an ALK receptor inhibitor) could be used to induce mouse fibroblasts in SMINS cells, as could a "core" combination of three small molecules (a G9a HMTase inhibitor, a MEK inhibitor, and a DNA methyltransferase inhibitor), and surprisingly established that just a single small molecule; a MEK inhibitor could induce SMINS cells.

Example 2 establishes that small molecules, in the absence of polypeptide or polynucleotide reprogramming factors, can be used to induce (or reprogram) somatic cells such as human embryonic fibroblast cells (HUCF) into SMINS cells that expressed the neural stem cell markers. It was demonstrated that a combination of the three small molecules (a G9a HMTase inhibitor, a MEK inhibitor, and a DNA methyltransferase inhibitor), two small molecules (a G9a HMTase inhibitor and a DNA methyltransferase inhibitor; or a G9a HMTase inhibitor and a MEK inhibitor) and a single small molecule (a G9a HMTase inhibitor or a MEK inhibitor) are capable of inducing colonies and cells to express the neural cell marker, ALP. The induced SMINS expressed the neural stem cell genes Sox2 and SSEA-1, indicating the cells are neural stem cells. Additionally, cells induced with the G9a HMTase inhibitor alone following just 6 days in NSC media were found to express the neural crest cell marker p75-NTR, the neural stem marker nestin, the oligodendrocyte progenitor markers NG2 and Olig2, the astrocyte marker GFAP, and neuronal marker Tuj1. These results show that the SMINS cells, following 6 days in NSC, have a primitive morphology and simultaneously express multiple neural lineage markers, indicating the cells have the potential to differentiate into different cells in the neural lineage. It is expected that these cells would fully differentiate into various neural lineage cells (eg neurons, oligodendrocytes, astrocytes) in the same manner as shown for the mouse fibroblasts. Moreover, the similarity of the results obtained in the mouse cells as compared to the human cells indicates that the mouse induction model is representative of induction of human SMINS cells.

Example 3 establishes that SMINS cells can be induced from TTF or MEF using small molecules. These SMINS cells are very similar to the native NS cells in morphology and express the neural stem cell markers Sox2, SSEA-1, GFAP, Tuj1 and Olig2 and neural stem cell marker genes including Sox2, GFAP, Olig2 and Gli2, but do not express the pluripotent genes Oct4 and Nanog. Furthermore, SM INS cells were able to differentiate into astrocytes, neurons, oligodendrocytes, or mature neurons. This data clearly demonstrates that our protocol using small molecules is reliable, reproducible and practical to induce the formation of neurospheres from mouse fibroblasts and that the SMINS cells are unlikely to be derived from skin neural crest stem cells.

Example 4 establishes that SMINS can also be induced from HUCF using a multiple induction cycles.

Example 5 indicates that SMINS can be induced from HUFC using a combination of small molecules, all of which include the G9a HMTase inhibitor chaetocin. Colonies induced from HUCF cells were ALP positive and appeared morphologically similar to those produced in the previous Examples. These results indicate that the tested combination of small molecules is capable of induced neural stem cells similar to those of Examples 1, 2, 3 and 4.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by the person skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Han, D W. et al. *Nature Cell Biology* 13:66-U153 (2011).
2. Takahashi, K. & Yamanaka, S. *Cell* 126:663-676 (2006).
3. Okita, K. et al. *Nature* 448:313-U311 (2007).
4. Wernig, M. et al. *Nature* 448:318-U312 (2007).
5. Takahashi, K. et al. *Cell* 131:861-872 (2007).
6. Yu, J Y. et al. *Science* 318:1917-1920 (2007).
7. Park, I H. et al. *Nature* 451:141-U141 (2008).
8. Lowry, W E. et al. *Proc Natl Acad Sci USA* 105:2883-2888 (2008).
9. Dimos, J T. et al. *Science* 321:1218-1221 (2008).
10. Anokye-Danso, F. et al. *Cell Stem Cell* 8:376-388 (2011).
11. Hanna, J. et al. *Proc Natl Acad Sci USA* 107:9222-9227 (2010).
12. Shi, Y. et al. *Cell Stem Cell* 2:525-528 (2008).
13. Huangfu, D. et al. *Nat Biotechnol* 26:795-797 (2008).
14. Lyssiotis, C A. et al. *Proc Natl Acad Sci USA* 106:8912-8917 (2009).
15. Ichida, J K. et al. *Cell Stem Cell* 5:491-503 (2009).
16. Lin, T. et al. *Nat Methods* 6:805-808 (2009).
17. Li, W. et al. *Stem Cells* 27:2992-3000 (2009).
18. Esteban, M A. et al. *Cell Stem Cell* 6:71-79 (2010).
19. Li, Y. et al. *Cell Res* 21:196-204 (2011).
20. Zhu, S. et al. *Cell Stem Cell* 7:651-655 (2010).
21. Xu, Y. et al. *Proc Natl Acad Sci USA* 107:8129-8134 (2010).
22. Goldman, S A. & Windrem, M S. *Philos Trans R Soc Lond B Biol Sci* 361:1463-1475(2006).
23. Lee, J P. et al. *Nature Medicine* 13:439-447 (2007).
24. Toma, J G. et al. *Nature Cell Biology* 3:778-784 (2001).
25. Hitoshi, S. et al. *Genes Dev* 16:846-858 (2002).
26. Mizutani, K. et al. *Nature* 449:351-355 (2007).
27. Aguirre, A. et al. *Nature* 467:323-327 (2010).
28. Lie, D C. et al. *Nature* 437:1370-1375 (2005).
29. Kalani, M Y. et al. *Proc Natl Acad Sci USA* 105:16970-16975 (2008).
30. Lim, D A. et al. *Neuron* 28:713-726 (2000).
31. Mira, H. et al. *Cell Stem Cell* 7:78-89 (2010).
32. Lai, K. et al. *Nat Neurosci* 6:21-27 (2003).
33. Ying, Q L. et al. *Nature* 453:519-523 (2008).
34. Szabo, E. et al. *Nature* 468:521-U191 (2010).
35. Bain, J. et al., *Biochem J*. 408:297-315 (2007).
36. Sebolt-Leopold, J. S. & Herrera, R. *Nature Rev Cancer* 4:937-947 (2004).
37. Jung, G. et al., *BMC Cell Biology* 9(66):1-12 (2008).
38. Huangfu, D. et al., *Nat Biotech* 26:795-797 (2009).
39. Kubicek, S. et al., *Mol Cell* 25:473-481 (2007).
40. Shi, Y. et al, *Cell Stem Cell* 2:525-528 (2008).
41, Brueckner, B. et al., *Cancer Res* 65:6305-6311 (2005).
42. Tsumura, A. et al., *Genes to Cells* 11:805-814 (2006).
43. Ying, Q. et al., *Nature* 453: 519-524 (2008).
44. Esteban, M et al. *Cell Stem Cell* 6:71-79 (2009).
45. Shi, Y. *Nat Rev Genet* 8:829-833 (2007).
46. Tojo, M. et al., *Cancer Sci* 96:791-800 (2005).
47. Li, W. et al., *Cell Stem Cell* 4:16-19 (2009).
48. Vierbuchen, T. et al. *Nature* 463:1035-1041 (2010).
49. Maherali, N. & Hochedlinger, K. *Curr Biol* 19:1718-1723 (2009).
50. Koch, P, et al., *PNAS* 106: 3225-3230 (2009)
51. Watanabe, K. et al. *Nat Neurosci* 8: 288-296 (2005)
52. Kim, D.-S. et al. *PLoS One*, 7(7): e39715 (2012)
53. Liu, H and Zhang, S.-C. *Cell Mol Life Sci* 68(24): 3995-4008 (2011)
54. Yan et al. *Stem Cells* 23:781-790 (2005)

The invention claimed is:

1. A method of producing a multipotent neural stem cell that expresses ALP, Sox2, and SSEA1, said method comprising culturing at least one fibroblast cell in the presence of an effective amount of at least one small molecule reprogramming factor(s) that induces the cell to de-differentiate into a multipotent neural stem cell that expresses ALP, Sox2 and SSEA1, wherein the small molecule reprogramming factor(s) is selected from the group consisting of G9a HMTase inhibitors and MEK inhibitors, and, wherein the method excludes the use of exogenous reprogramming factor(s) that are not small molecules that induce the cell to de-differentiate into a multipotent neural stem cell.

2. The method of claim 1, wherein the small molecule reprogramming factor(s) is a G9a HMTase inhibitor(s).

3. The method of claim 2, wherein the G9a HMTase inhibitor(s) is in combination with an effective amount of at least one further small molecule reprogramming factor(s) selected from the group consisting of a histone deacetylase (HDAC) inhibitor(s), a MEK inhibitor(s), a DNA methyltransferase inhibitor(s), a glycogen synthase kinase 3 (GSK3) inhibitor(s), Vitamin C, and a Activin receptor-like kinase (ALK) receptor inhibitor(s).

4. The method of claim 2, wherein the G9a HMTase inhibitor(s) is in combination with a DNA methyltransferase inhibitor(s).

5. The method of claim 2, wherein the G9a HMTase inhibitor(s) is in combination with a DNA methyltransferase inhibitor(s) and a MEK inhibitor(s).

6. The method of claim 1, wherein the small molecule reprogramming factor(s) is a MEK inhibitor(s).

7. The method of claim 1, wherein the MEK inhibitor(s) is in combination with an effective amount of at least one further small molecule reprogramming factor(s) selected from the group consisting of a HDAC inhibitor(s), a G9a HMTase inhibitor(s), a DNA methyltransferase inhibitor(s) a GSK3 inhibitor(s), Vitamin C, and a ALK receptor inhibitor(s).

8. The method of claim 1, wherein the G9a HMTase inhibitor(s) is 2-(hexahydro-4-methyl-1H-1,4-diazepin-1-yl)-6,7-dimethoxy-N-[1-(phenylmethyl)-4-piperidinyl]-4-quinazolinamine trihydrochloride hydrate (BIX01294).

9. The method of claim 3, wherein the DNA methyltransferase inhibitor(s) is 1H-Indole-3-propanoic acid, α-(1,3-dihydro-1,3-dioxo-2H-isoindol-2-yl)-, (αS)— (RG108).

10. The method of claim 1, wherein the MEK inhibitor(s) is N-(2,3-dihydroxy-propoxy)-3,4-difluoro-2-(2-fluoro-4-iodo-phenylamino)-benzamide (PD325901).

11. The method of claim 1, wherein the multipotent neural stem cell is a human cell.

12. The method of claim 1, wherein the culturing comprises:
(a) performing an at least one induction cycle comprising culturing for approximately one day the at least one fibroblast cell in the presence of an effective amount of at least one small molecule reprogramming factor(s) that induces the cell to de-differentiate into a multipotent neural stem cell, and then culturing for approximately two days the at least one cell in the absence of said effective amount of at least one small molecule reprogramming factor(s), and optionally
(b) culturing the at least one cell of step (a) in media adapted to support multipotent neural stem cell growth for a suitable period.

* * * * *